(12) United States Patent
Lee et al.

(10) Patent No.: US 11,510,999 B2
(45) Date of Patent: Nov. 29, 2022

(54) TREATMENT OF NEUROPATHY WITH DNA CONSTRUCTS EXPRESSING IGF-1 ISOFORMS

(71) Applicant: Helixmith Co., Ltd, Seoul (KR)

(72) Inventors: Junghun Lee, Seoul (KR); Nayeon Lee, Seoul (KR); Kyeong Ryang Ko, Seoul (KR)

(73) Assignee: Helixmith Co., Ltd, Seoul (KR)

( * ) Notice: Subject to any disclaimer, the term of this patent is extended or adjusted under 35 U.S.C. 154(b) by 168 days.

(21) Appl. No.: 16/513,564

(22) Filed: Jul. 16, 2019

(65) Prior Publication Data

US 2020/0023077 A1    Jan. 23, 2020

Related U.S. Application Data

(60) Provisional application No. 62/699,662, filed on Jul. 17, 2018.

(51) Int. Cl.
| | |
|---|---|
| *C12N 15/113* | (2010.01) |
| *C12N 15/18* | (2006.01) |
| *C12N 15/11* | (2006.01) |
| *A61K 48/00* | (2006.01) |
| *C07K 14/65* | (2006.01) |
| *A61P 25/02* | (2006.01) |
| *C12N 15/86* | (2006.01) |

(Continued)

(52) U.S. Cl.
CPC ........ *A61K 48/0066* (2013.01); *A61K 9/0019* (2013.01); *A61K 48/0075* (2013.01); *A61P 25/02* (2018.01); *C07K 14/65* (2013.01); *C12N 15/86* (2013.01); *A61K 38/00* (2013.01); *C12N 2800/107* (2013.01)

(58) Field of Classification Search
None
See application file for complete search history.

(56) References Cited

U.S. PATENT DOCUMENTS

| | | | | |
|---|---|---|---|---|
| 8,338,385 B2 * | 12/2012 | Kim | .......................... | A61P 9/10 |
| | | | | 514/44 R |
| 2005/0153886 A1 * | 7/2005 | Crystal | .................. | A61P 19/02 |
| | | | | 536/23.5 |

(Continued)

FOREIGN PATENT DOCUMENTS

| | | |
|---|---|---|
| RU | 2372941 C2 | 11/2009 |
| WO | WO 98/24922 A1 | 6/1998 |

(Continued)

OTHER PUBLICATIONS

Philippou et al., Evidence for the possible biological significance of the igf-1 gene alternative splicing in prostate cancer. Front Endocrin, 2013, 4:1-11 (Year: 2013).*

(Continued)

*Primary Examiner* — Arthur S Leonard
(74) *Attorney, Agent, or Firm* — Fenwick & West LLP

(57) ABSTRACT

The present invention relates to a DNA construct encoding one or more human IGF-1 isoforms that can be used for treatment of neuropathy. Further provided herein are a pharmaceutical composition including the DNA construct as an active ingredient and a method of administering the DNA construct for treatment of neuropathy. The present invention provides a safe and effective way of treating neuropathic patients.

15 Claims, 7 Drawing Sheets

Specification includes a Sequence Listing.

IGF-1 isoforms

1 Class I, Ec

2 Class II, Ea

3 Class I, Eb

4 Class I, Ea

(51) Int. Cl.
  *A61K 9/00* (2006.01)
  *A61K 38/00* (2006.01)

(56) References Cited

U.S. PATENT DOCUMENTS

| | | | |
|---|---|---|---|
| 2006/0058239 A1 | 3/2006 | Johnson et al. | |
| 2007/0135340 A1* | 6/2007 | Rosenthal | C07K 14/65 435/69.1 |
| 2010/0216709 A1 | 8/2010 | Scheule et al. | |
| 2018/0055889 A1* | 3/2018 | Anversa | C12N 5/0662 |

FOREIGN PATENT DOCUMENTS

| | | | | |
|---|---|---|---|---|
| WO | WO-9824922 A1 * | 6/1998 | | A61P 19/10 |
| WO | WO 99/36103 A1 | 7/1999 | | |
| WO | WO-0040737 A1 * | 7/2000 | | A61P 9/10 |
| WO | WO 2007/142651 A1 | 12/2007 | | |
| WO | WO 2009/093880 A2 | 7/2009 | | |
| WO | WO 2012/118796 A1 | 9/2012 | | |
| WO | WO 2016/064737 A1 | 4/2016 | | |
| WO | WO 2019/156540 A1 | 8/2019 | | |
| WO | WO 2019/156541 A1 | 8/2019 | | |

OTHER PUBLICATIONS

Hill et al. Blackwell Publishing Ltd. Muscle satellite (stem) cell activation during local tissue injury and repair (J. Anat, 2003, 203:89-99) (Year: 2003).*
Rotwein et al. Organization and Sequence of the Human Insulin-like Growth Factor I Gene (JBC, 1986 261:4828-4832) (Year: 1986).*
NCBI, "*Homo sapiens* Human insulin-like growth factor I (IGF1) gene, intron 4," GenBank Accession No. AH003176.2, Aug. 25, 2016, pp. 1-2.
NCBI, "*Homo sapiens* insulin-like growth factor 1 (somatomedin C) (IGF1) gene, complete cds," GenBank Accession No. AY260957. 1, Apr. 3, 2003, pp. 1-33.
NCBI, "insulin-like growth factor I isoform 1 preproprotein [*Homo sapiens*]," GenBank Accession No. NP_001104753.1, Jun. 17, 2018, pp. 1-3.
NCBI, "insulin-like growth factor I isoform 4 preproprotein [*Homo sapiens*]," GenBank Accession No. NP_000609.1, Jun. 17, 2018, pp. 1-3.
Oberbauer, A. M., "The regulation of IGF-1 gene transcription and splicing during development and aging," Frontiers in Endocrinology, vol. 4, Mar. 2013, pp. 1-9.
PCT International Search Report and Written Opinion, PCT Application No. PCT/IB2019/000843, dated Feb. 3, 2020, 15 pages.
Philippou, A. et al., "The Complexity of the IGF1 Gene Splicing, Posttranslational Modification and Bioactivity," Molecular Medicine, vol. 20, Mar. 12, 2014, pp. 202-214.
Ajroud-Driss S, Christiansen M, Allen JA, Kessler JA. Phase 1/2 open-label dose-escalation study of plasmid DNA expressing two isoforms of hepatocyte growth factor in patients with painful diabetic peripheral neuropathy. Mol Ther. 2013;21:1279-1286.
Akita H, Takagi N, Ishihara N, et al. Hepatocyte growth factor improves synaptic localization of the NMDA receptor and intracellular signaling after excitotoxic injury in cultured hippocampal neurons. Exp Neurol. 2008;210:83-94.
Apfel, SC, Schwartz, S, Adornato, BT, Freeman, R, Biton, V, Rendell, M et al. (2000). Efficacy and safety of recombinant human nerve growth factor in patients with diabetic polyneuropathy: A randomized controlled trial. rhNGF Clinical Investigator Group. JAMA 284: 2215-2221.
Bansal et al., "Diabetic neuropathy," Postgrad Med J. 82(964):95-100 (2006).
Bissonette GB, Bae MH, Suresh T, et al. Prefrontal cognitive deficits in mice with altered cerebral cortical GABAergic interneurons. Behav Brain Res. 2014;259:143-151.

Bottaro DP, Rubin JS, Faletto DL, et al. Identification of the hepatocyte growth factor receptor as the c-met proto-oncogene product. Science. 1991;251:802-804.
Bril, V, England, J, Franklin, GM, Backonja, M, Cohen, J, Del Toro, D et al.; American Academy of Neurology; American Association of Neuromuscular and Electrodiagnostic; Medicine; American Academy of Physical Medicine and Rehabilitation. (2011). Evidence-based guideline: Treatment of painful diabetic neuropathy: report of the American Academy of Neurology, the American Association of Neuromuscular and Electrodiagnostic Medicine, and the American Academy of Physical Medicine and Rehabilitation. Neurology 76: 1758-1765.
Bussolino, F, DiRenzo, MF, Ziche, M, Bocchietto, E, Olivero, M, Naldini, L et al. (1992). Hepatocyte growth factor is a potent angiogenic factor which stimulates endothelial cell motility and growth. J Cell Biol 119: 629-641.
Calabrese EJ, Baldwin LA. Hormesis: the dose-response revolution. Annu Rev Pharmacol Toxicol. 2003;43:175-197.
Calabrese EJ. Enhancing and regulating neurite outgrowth. Crit Rev Toxicol. 2008;38:391-418.
Callaghan, BC, Cheng, HT, Stables, CL, Smith, AL and Feldman, EL (2012). Diabetic neuropathy: clinical manifestations and current treatments. Lancet Neurol 11:521-534.
Cameron, NE, Eaton, SE, Cotter, MA and Tesfaye, S (2001). Vascular factors and metabolic interactions in the pathogenesis of diabetic neuropathy. Diabetologia 44:1973-1988.
Canton, A, Burgos, R, Hernandez, C, Mateo, C, Segura, RM, Mesa, J et al. (2000). Hepatocyte growth factor in vitreous and serum from patients with proliferative diabetic retinopathy. Br J Ophthalmol 84: 732-735.
Carlsson, M, Osman, NF, Ursell, PC, Martin, AJ and Saeed, M (2008). Quantitative MR measurements of regional and global left ventricular function and strain after intramyocardial transfer of VM202 into infarcted swine myocardium. Am J Physiol Heart Circ Physiol 295: H522-H532.
Cheng C, Guo GF, Martinez JA, et al. Dynamic plasticity of axons within a cutaneous milieu. J Neurosci. 2010;30:14735-14744.
Cho, KR, Choi, JS, Hahn, W, Kim, DS, Park, JS, Lee, DS et al. (2008). Therapeutic angiogenesis using naked DNA expressing two isoforms of the hepatocyte growth factor in a porcine acute myocardial infarction model. Eur J Cardiothorac Surg 34:857-863.
Cleeland CS, Ryan KM. Pain assessment: global use of the Brief Pain Inventory. Ann Acad Med Singapore. 1994;23:129-138 (abstract only).
Davies, M, Brophy, S, Williams, R and Taylor, A (2006). The prevalence, severity, and impact of painful diabetic peripheral neuropathy in type 2 diabetes. Diabetes Care 29:1518-1522.
Dworkin, RH, Turk, DC, Wyrwich, KW, Beaton, D, Cleeland, CS, Farrar, JT et al. (2008). Interpreting the clinical importance of treatment outcomes in chronic pain clinical trials: IMMPACT recommendations. J Pain 9: 105-121.
Ebens, A, Brose, K, Leonardo, ED, Hanson, MG Jr, Bladt, F, Birchmeier, C et al.(1996). Hepatocyte growth factor/scatter factor is an axonal chemoattractant and a neurotrophic factor for spinal motor neurons. Neuron 17: 1157-1172.
Eck, Goodman & Gilman's the Pharmacological basis of Therapeutics, 1996, McGraw-Hill, New York, NY. pp. 77-101.
Edwards, JL, Vincent, AM, Cheng, HT and Feldman, EL (2008). Diabetic neuropathy: mechanisms to management. Pharmacol Ther 120: 1-34.
Elbaz A, Bower JH, Maraganore DM, et al. Risk tables for parkinsonism and Parkinson's disease. J Clin Epidemiol. 2002;55:25-31.
Funakoshi H, Nakamura T. Identification of HGF-like protein as a novel neurotrophic factor for avian dorsal root ganglion sensory neurons. Biochem Biophys Res Commun. 2001;283:606-612.
Gascon, E, Gaillard, S, Malapert, P, Liu, Y, Rodat-Despoix, L, Samokhvalov, IM et al.(2010). Hepatocyte growth factor-Met signaling is required for Runx1 extinction and peptidergic differentiation in primary nociceptive neurons. J Neurosci 30: 12414-12423.
Gille, J, Khalik, M, Konig, V and Kaufmann, R (1998). Hepatocyte growth factor/scatter factor (HGF/SF) induces vascular permeability factor (VPF/VEGF) expression by cultured keratinocytes. J Invest Dermatol 111: 1160-1165.

(56) References Cited

OTHER PUBLICATIONS

Gore, M, Brandenburg, NA, Dukes, E, Hoffman, DL, Tai, KS and Stacey, B (2005). Pain severity in diabetic peripheral neuropathy is associated with patient functioning, symptom levels of anxiety and depression, and sleep. J Pain Symptom Manage 30:374-385.

Gu, Y, Zhang, J, Guo, L, Cui, S, Li, X, Ding, D et al. (2011). A phase I clinical study of naked DNA expressing two isoforms of hepatocyte growth factor to treat patients with critical limb ischemia. J Gene Med 13:602-610.

Hahn, W, Pyun, WB, Kim, DS, Yoo, WS, Lee, SD, Won, JH et al. (2011). Enhanced cardioprotective effects by coexpression of two isoforms of hepatocyte growth factor from naked plasmid DNA in a rat ischemic heart disease model. J Gene Med 13:549-555.

Hashimoto N, Yamanaka H, Fukuoka T, et al. Expression of hepatocyte growth factor in primary sensory neurons of adult rats. Brain Res Mol Brain Res. 2001;97:83-88.

Hashimoto, N, Yamanaka, H, Fukuoka, T, Dai, Y, Obata, K, Mashimo, T et al. (2001). Expression of HGF and cMet in the peripheral nervous system of adult rats following sciatic nerve injury. Neuroreport 12: 1403-1407.

Hebert LE, Weuve J, Scherr PA, Evans DA. Alzheimer disease in the United States (2010-2050) estimated using the 2010 census. Neurology. 2013;80:1778-1783.

Henry, TD, Hirsch, AT, Goldman, J, Wang, YL, Lips, DL, McMillan, WD et al. (2011). Safety of a non-viral plasmid-encoding dual isoforms of hepatocyte growth factor in critical limb ischemia patients: a phase I study. Gene Ther 18: 788-794.

International Search Report for International Application No. PCT/KR2012/002224, dated Oct. 12, 2012 (6 pages).

Jayasankar, V, Woo, YJ, Pirolli, TJ, Bish, LT, Berry, MF, Burdick, J et al. (2005). Induction of angiogenesis and inhibition of apoptosis by hepatocyte growth factor effectively treats postischemic heart failure. J Card Surg 20: 93-101.

Jensen MP, Chodroff MJ, Dworkin RH. The impact of neuropathic pain on health-related quality of life: review and implications. Neurology 2007;68:1178-1182 (abstract only).

Kaiser, J., "Death Prompts a Review of Gene Therapy Vector," Science, vol. 317, Aug. 3, 2007, pp. 580.

Kato N, Nemoto K, Nakanishi K, et al. Nonviral gene transfer of human hepatocyte growth factor improves streptozotocin-induced diabetic neuropathy in rats. Diabetes. 2005;54:846-854.

Kato N, Nemoto K, Nakanishi K, et al. Nonviral HVJ (hemagglutinating virus of Japan) liposome-mediated retrograde gene transfer of human hepatocyte growth factor into rat nervous system promotes functional and histological recovery of the crushed nerve. Neurosci Res. 2005;52:299-310.

Keizer D, Fael D, Wierda JMKH, van Wijhe M. Quantitative sensory testing with Von Frey monofilaments in patients with allodynia: what are we quantifying? Clin J Pain. 2008;24:463-466.

Kim et al., "Development of innovative biomedicine: A case study on cardiovascular gene medicine using naked DNA expressing two isoforms of hepatocyte growth factor," Second workshop of new medicine developer, ViroMed Co. Ltd., published Jun. 1, 2011 (55 pages).

Kim, JS, Hwang, HY, Cho, KR, Park, EA, Lee, W, Paeng, JC et al. (2013). Intramyocardial transfer of hepatocyte growth factor as an adjunct to CABG: phase I clinical study. Gene Ther (doi:10.1038/gt.2012.87).

Ko, K.R et al., "Hepatocyte Growth Factor (HGF) Promotes Peripheral Nerve Regeneration by Activating Repair Schwann Cells," Scientific Reports, May 29, 2018, pp. 1-14.

Koike H, Ishida A, Shimamura M, et al. Prevention of onset of Parkinson's disease by in vivo gene transfer of human hepatocyte growth factor in rodent model: a model of gene therapy for Parkinson's disease. Gene Ther. 2006;13:1639-1644.

Konstorum A, Sprowl SA, Waterman ML, et al. Predicting mechanism of biphasic growth factor action on tumor growth using a multi-species model with feedback control. J Coupled Syst Multiscale Dyn. 2013;1:459-467.

Lee, Y, Park, EJ, Yu, SS, Kim, DK and Kim, S (2000). Improved expression of vascular endothelial growth factor by naked DNA in mouse skeletal muscles: implication for gene therapy of ischemic diseases. Biochem Biophys Res Commun 272: 230-235.

Lin et al., "VEGF and its receptor-2 involved in neuropathic pain transmission mediated by P2X.sub.2/3 receptor of primary sensory neurons," Brain Res Bull. 83(5):284-91 (2010).

Liu, ML, Mars, WM, Zarnegar, R and Michalopoulos, GK (1994). Uptake and distribution of hepatocyte growth factor in normal and regenerating adult rat liver. Am J Pathol 144: 129-140.

Lokker NA, Mark MR, Luis EA, et al. Structure-function analysis of hepatocyte growth factor: identification of variants that lack mitogenic activity yet retain high affinity receptor binding. EMBO J. 1992;11:2503-2510.

Madiai et al., "Anti-fibroblast growth factor-2 antibodies attenuate mechanical allodynia in a rat model of neuropathic pain," J Mol Neurosci 27(3):315-24 (2005), Abstract Only.

Maina, F, Hilton, MC, Andres, R, Wyatt, S, Klein, R and Davies, AM (1998). Multiple roles for hepatocyte growth factor in sympathetic neuron development. Neuron 20:835-846.

Maina, F, Hilton, MC, Ponzetto, C, Davies, AM and Klein, R (1997). Met receptor signaling is required for sensory nerve development and HGF promotes axonal growth and survival of sensory neurons. Genes Dev 11:3341-3350.

Matsumoto, K and Nakamura, T (1996). Emerging multipotent aspects of hepatocyte growth factor. J Biochem 119: 591-600.

McDowell I. Alzheimer's disease: insights from epidemiology. Aging (Milano) 2001;13:143-162 (abstract only).

Menichella et al., "CXCR4 chemokine receptor signaling mediates pain in diabetic neuropathy," Mol Pain. 10(42):1-13 (2014).

Micheva KD, Taylor CP, Smith SJ. Pregabalin reduces the release of synaptic vesicles from cultured hippocampal neurons. Mol Pharmacol. 2006;70:467-476.

Moghtaderi A, Bakhshipour A, Rashidi H. Validation of Michigan neuropathy screening instrument for diabetic peripheral neuropathy. Clin Neurol Neurosurg. 2006;108:477-481.

Morishita, R, Aoki, M, Yo, Y and Ogihara, T (2002). Hepatocyte growth factor as cardiovascular hormone: role of HGF in the pathogenesis of cardiovascular disease. Endocr J 49: 273-284.

Nakagami, H, Kaneda, Y, Ogihara, T and Morishita, R (2005). Hepatocyte growth factor as potential cardiovascular therapy. Expert Rev Cardiovasc Ther 3: 513-519 (abstract only).

Nho, B. et al., "Effective control of neuropathic pain by transient expression of hepatocyte growth factor in a mouse chronic constriction injury model," The FASEB Journal, Aug. 30, 2018, pp. 1-13.

Nomura M, Oketa Y, Yasui K, et al. Expression of hepatocyte growth factor in the skin of amyotrophic lateral sclerosis. Acta Neurol Scand. 2012;125:389-397.

O'Connor AB. Neuropathic pain: quality-of-life impact, costs and cost effectiveness of therapy. Pharmacoeconomics. 2009;27:95-112 (abstract only).

Perin, EC, Silva, GV, Vela, DC, Zheng, Y, Baimbridge, F, Gahremanpour, A et al. (2011). Human hepatocyte growth factor (VM202) gene therapy via transendocardial injection in a pig model of chronic myocardial ischemia. J Card Fail 17: 601-611.

Pyun, WB, Hahn, W, Kim, DS, Yoo, WS, Lee, SD, Won, JH et al. (2010). Naked DNA expressing two isoforms of hepatocyte growth factor induces collateral artery augmentation in a rabbit model of limb ischemia. Gene Ther 17: 1442-1452.

Ropper, AH, Gorson, KC, Gooch, CL, Weinberg, DH, Pieczek, A, Ware, JH et al. (2009). Vascular endothelial growth factor gene transfer for diabetic polyneuropathy: a randomized, double-blinded trial. Ann Neurol 65: 386-393.

Russo AJ, Krigsman A, Jepson B, Wakefield A. Decreased serum hepatocyte growth factor (HGF) in autistic children with severe gastrointestinal disease. Biomark Insights. 2009;4:181-190.

Russo AJ, Pietsch SC. Decreased hepatocyte growth factor (HGF) and gamma aminobutyric acid (GABA) in individuals with obsessive-compulsive disorder (OCD) Biomark Insights. 2013;8:107-114.

Saeed, M, Martin, A, Ursell, P, Do, L, Bucknor, M, Higgins, CB et al. (2008). MR assessment of myocardial perfusion, viability, and

(56) References Cited

OTHER PUBLICATIONS function after intramyocardial transfer of VM202, a new plasmid human hepatocyte growth factor in ischemic swine myocardium. Radiology 249: 107-118.

Saeed, M, Saloner, D, Do, L, Wilson, M and Martin, A (2011). Cardiovascular magnetic resonance imaging in delivering and evaluating the efficacy of hepatocyte growth factor gene in chronic infarct scar. Cardiovasc Revasc Med 12: 111-122.

Shakher, J and Stevens, MJ (2011). Update on the management of diabetic polyneuropathies. Diabetes Metab Syndr Obes 4: 289-305.

Sharma S. Hepatocyte growth factor in synaptic plasticity and Alzheimer's disease. ScientificWorldJournal. 2010;10:457-461.

Shima N, Tsuda E, Goto M, et al. Hepatocyte growth factor and its variant with a deletion of five amino acids are distinguishable in their biological activity and tertiary structure. Biochem Biophys Res Commun. 1994;200:808-815.

Snedecor SJ, Sudharshan L, Cappelleri JC, et al. Systematic review and meta-analysis of pharmacological therapies for painful diabetic peripheral neuropathy. Pain Pract. 2014;14:167-184.

Taniyama Y, Morishita R, Aoki M, et al. Therapeutic angiogenesis induced by human hepatocyte growth factor gene in rat and rabbit hindlimb ischemia models: preclinical study for treatment of peripheral arterial disease. Gene Ther. 2001;8:181-189.

Taniyama Y, Morishita R, Hiraoka K, et al. Therapeutic angiogenesis induced by human hepatocyte growth factor gene in rat diabetic hind limb ischemia model: molecular mechanisms of delayed angiogenesis in diabetes. Circulation. 2001;104:2344-2350.

Taylor CP, Angelotti T, Fauman E. Pharmacology and mechanism of action of pregabalin: the calcium channel alpha2-delta (alpha2-delta) subunit as a target for antiepileptic drug discovery. Epilepsy Res. 2007;73:137-150.

Tesfaye, S and Selvarajah, D (2012). Advances in the epidemiology, pathogenesis and management of diabetic peripheral neuropathy. Diabetes Metab Res Rev 28 Suppl 1:8-14.

Tesfaye, S, Vileikyte, L, Rayman, G, Sindrup, S, Perkins, B, Baconja, M et al.; on behalf of the Toronto Expert Panel on Diabetic Neuropathy*. (2011). Painful Diabetic Peripheral Neuropathy: Consensus Recommendations on Diagnosis, Assessment and Management. Diabetes Metab Res Rev 27: 629-638.

Thompson J, Dolcet X, Hilton M, et al. HGF promotes survival and growth of maturing sympathetic neurons by PI-3 kinase- and MAP kinase-dependent mechanisms. Mol Cell Neurosci. 2004;27:441-452.

Tsuchihara, T, Ogata, S, Nemoto, K, Okabayashi, T, Nakanishi, K, Kato, N et al. (2009). Nonviral Yetrograde gene transfer of human hepatocyte growth factor improves neuropathic pain-related phenomena in rats. Mol Ther 17:42-50.

United States Office Action, U.S. Appl. No. 14/355,792, dated Oct. 5, 2017, 7 pages.

United States Office Action, U.S. Appl. No. 15/942,440, filed Jun. 1, 2018, 11 pages.

Veves A, Backonja M, Malik RA. Painful diabetic neuropathy: epidemiology, natural history, early diagnosis, and treatment options. Pain Med. 2008;9:660-674.

Vinik AI, Nevoret ML, Casellini C, Parson H. Diabetic neuropathy. Endocrinol Metab Clin North Am. 2013;42:747-787.

Wong, V, Glass, DJ, Arriaga, R, Yancopoulos, GD, Lindsay, RM and Conn, G (1997). Hepatocyte growth factor promotes motor neuron survival and synergizes with ciliary neurotrophic factor. J Biol Chem 272: 5187-5191.

Yang, XM, Toma, JG, Bamji, SX, Belliveau, DJ, Kohn, J, Park, M et al. (1998). Autocrine hepatocyte growth factor provides a local mechanism for promoting axonal growth. J Neurosci 18: 8369-8381.

Zelman, DC, Gore, M, Dukes, E, Tai, KS and Brandenburg, N (2005). Validation of a modified version of the brief pain inventory for painful diabetic peripheral neuropathy. J Pain Symptom Manage 29: 401-410.

Zheng LF, Wang R, Yu QP, et al. Expression of HGF/c-Met is dynamically regulated in the dorsal root ganglions and spinal cord of adult rats following sciatic nerve ligation. Neurosignals. 2010;18:49-56.

De Palma, M. et al., "In Vivo Targeting of Tumor Endothelial Cells by Systemic Delivery of Lentiviral Vectors," Human Gene Therapy, vol. 14, Aug. 10, 2003, pp. 1193-1206.

Gautam, A. et al., "Delivery Systems for Pulmonary Gene Therapy," Am J Respir Med 1(1), Jan. 2002, pp. 35-46.

Kay, M.A. et al., "State-of-the-art gene-based therapies: the road ahead," Nature Reviews Genetics, vol. 12, May 2011, pp. 316-328.

Ngo, J.T. et al., "Computational Complexity, Protein Structure Prediction, and the Levinthal Paradox," in the Protein Folding Problem and Tertiary Structure Prediction, 1994, pp. 491-495.

Romano, G., "Gene Transfer in Experimental Medicine," Drug News Perspect 16(5), Jun. 2003, pp. 267-276.

Said, G. "Diabetic neuropathy—a Review," Nature Clinical Practice Neurology, vol. 3, No. 6, Jun. 2007, pp. 331-340.

Soofiyani, S.R. et al., "Gene Therapy, Early Promises, Subsequent Problems, and Recent Breakthroughs," Advanced Pharmaceutical Bulletin 3(2), Aug. 20, 2013, pp. 249-255.

Tolbert, W.D. et al., "Structural basis for agonism and antagonism of hepatocyte growth factor," PNAS, vol. 170, No. 30, Jul. 27, 2010, pp. 13264-13269.

The Federal Service for Intellectual Property, Office Action, Russian Patent Application No. 2021102481, dated Apr. 20, 2022, 17 pages.

European Patent Office, Extended European Search Report and Opinion, EP Patent Application No. 19837253.4, dated Mar. 4, 2022, 13 pages.

Flint, P.W. et al., "IGF-1 Gene Transfer into Denervated Rat Laryngeal Muscle," Archives of Otolaryngology Head and Neck Surgery, vol. 125, No. 3, Mar. 1999, pp. 274-279.

Gao, T. et al., "Systemic IGF-1 gene delivery by rAAV9 improves spontaneous autoimmune peripheral polyneuropathy (SAPP)," Scientific Reports, vol. 8, Apr. 3, 2018, pp. 1-11.

Kanje, M. et al., "Insulin-like growth factor I (IGF-I) stimulates regeneration of the rat sciatic nerve," Brain Research, vol. 486, Iss. 2, May 8, 1989, pp. 396-398.

Sullivan, K.A. et al., "Minireview: Insulin-Like Growth Factors in the Peripheral Nervous System," Endocrinology, vol. 149, No. 12, Aug. 21, 2008, pp. 5963-5971.

Kaufman, R.J., "Overview of Vector Design for Mammalian Gene Expression," Methods in Molecular Biology, vol. 62 Recombinant Gene Expression Protocols, Mar. 6, 1997, pp. 287-300.

Khan, K.H., "Gene Expression in Mammalian Cells and its Applications," Advanced Pharmaceutical Bulletin 3(2), Aug. 20, 2013, pp. 257-263.

Makrides, S.C., "Vectors for gene expression in mammalian cells," Chapter 2: Gene Transfer and Expression in Mammalian Cells, 2003, pp. 9-26.

Viola, J.R. et al., "Non-viral nanovectors for gene delivery: factors that govern successful therapeutics," Expert Opin Drug Deliv. 7(6), Jun. 2010, pp. 721-735.

\* cited by examiner

Amplicon size
- Isoform 1: 178bp, 259bp
- Isoform 4: 129bp

TREATMENT OF NEUROPATHY WITH DNA CONSTRUCTS EXPRESSING IGF-1 ISOFORMS

1. CROSS REFERENCE TO RELATED APPLICATIONS

This application claims priority to U.S. Provisional Application No. 62/699,662, filed Jul. 17, 2018, which is hereby incorporated by reference in its entirety.

2. SEQUENCE LISTING

The instant application contains a Sequence Listing which has been submitted via EFS-Web and is hereby incorporated by reference in its entirety. Said ASCII copy, created on Jul. 2, 2019, is named 38917US_CRF_sequencelisting.txt, and is 47,265 bytes in size.

3. BACKGROUND

Neuropathy is a chronic pathologic condition resulting from nerve damage. Neuropathy is a common consequence of diabetes, with neuropathy in a diabetic patient specifically referred to as diabetic neuropathy. Neuropathy can also be caused by nerve damage caused by infections (e.g., herpes, with the associated neuropathy arising after infection known as post-herpetic neuralgia; HIV/AIDS; Lyme disease: leprosy; syphilis; and shingles); autoimmune diseases (e.g., rheumatoid arthritis, systemic lupus, and Guillain-Barre syndrome); genetic or inherited disorders (e.g., Friedreich's ataxia and Charcot-Marie-Tooth disease); amyloidosis; uremia; exposure to toxins, poisons or drugs; trauma; or injury. In some cases, the cause is not known, in which case the neuropathy is referred to as idiopathic neuropathy.

Regardless of the cause, neuropathy is associated with characteristic symptoms that depend, in part, on the anatomic site of nerve damage (e.g., peripheral neuropathy, cranial neuropathy, autonomic neuropathy, focal neuropathy), such as pain (neuropathic pain), other sensory defects (e.g., anesthesias, including partial or complete loss of feeling; and paresthesias, including numbness, tingling, etc.), motor defects (e.g., weakness, loss of reflexes, loss of muscle mass, cramping, loss of dexterity, etc.), and autonomic dysfunction (e.g., nausea, vomiting, impotence, dizziness, constipation, diarrhea, etc.).

Neuropathy is routinely treated with measures that manage associated symptoms, and when the etiology is known, by treating the underlying cause of neuropathy. For example, pain medications, or medical treatments for diabetes, autoimmune diseases, infections, or vitamin deficiencies have been used. However, these methods do not treat the nerve damage itself.

There is, therefore, a need for an effective treatment method that can prevent and repair nerve damages associated with neuropathy.

Various growth factors have been suggested as possible agents for treating neuropathy, and Kessler and colleagues recently reported a successful double-blind, placebo-controlled, phase 2 human clinical trial of nonviral hepatocyte growth factor (HGF) gene therapy in diabetic peripheral neuropathy. Kessler et al., *Annals Clin. Transl. Neurology* 2(5):465-478 (2015). See also U.S. Pat. No. 9,963,493, incorporated herein by reference in its entirety.

Given the wide range of etiologies that cause neuropathy and the wide range of neuropathy clinical presentations, despite the clinical success in treating diabetic peripheral neuropathy with HGF-expressing nucleic acid constructs, there remains a need for additional treatments, including treatments based on administering growth factors other than HGF.

4. SUMMARY

The present invention is based on a novel finding that DNA constructs encoding a human IGF-1 isoform are effective in treating a symptom associated with neuropathy. It was further demonstrated that DNA constructs encoding Class I, Ec or Class I, Ea isoforms of IGF-1 are more effective than other DNA constructs encoding Class II, Ea or Class I, Eb isoform. The therapeutic effects become even more significant when the two types of DNA constructs, each encoding Class I, Ec or Class I, Ea isoforms of IGF-1, are administered together. Accordingly, some embodiments of the present invention are directed to a method of treating neuropathy by administering DNA constructs encoding Class I, Ec or Class I, Ea isoform of IGF-1, individually or in combination, to a subject with neuropathy.

The present invention further provides novel DNA constructs specifically designed to encode the two isoforms IGF-1 (i.e., Class I, Ec and Class I, Ea) in a single vector. The DNA constructs were screened and selected based on their capability to induce high-level expression of both Class I, Ec and Class I, Ea isoforms and effectively treat symptoms associated with neuropathy in vivo. Their treatment effects were greater than the effects of DNA constructs encoding only one of the two isoforms, Class I, Ec or Class I, Ea, and similar to the effects demonstrated by co-administration of two types of constructs, each encoding Class I, Ec or Class I, Ea.

Thus, the present invention provides a novel IGF-1 based therapy for treating neuropathy.

Specifically, in one aspect, the present invention provides an IGF-1 encoding DNA construct encoding human IGF-1, comprising: a first polynucleotide that has the same sequence as exons 1, 3 and 4 of the human IGF-1 gene (SEQ ID NO: 1) or a degenerate thereof; a second polynucleotide that has the same sequence as intron 4 of the human IGF-1 gene (SEQ ID NO: 2) or a fragment thereof; a third polynucleotide that has the same sequence as exons 5 and 6-1 of the human IGF-1 gene (SEQ ID NO: 3) or a degenerate thereof; a fourth polynucleotide that has the same sequence as intron 5 of the human IGF-1 gene (SEQ ID NO: 4) or a fragment thereof; and a fifth polynucleotide that has the same sequence as exon 6-2 of the human IGF-1 gene (SEQ ID NO: 5) or a degenerate thereof, wherein the first polynucleotide, the second polynucleotide, the third polynucleotide, the fourth polynucleotide and the fifth polynucleotide are linked in sequential 5' to 3' order.

In some embodiments, the second polynucleotide is a polynucleotide of SEQ ID NO: 6. In some embodiments, the second polynucleotide is a polynucleotide of SEQ ID NO: 7.

In some embodiments, the fourth polynucleotide is a polynucleotide of SEQ ID NO: 8.

In some embodiments, the IGF-1 encoding DNA construct further comprises a plasmid vector.

In some embodiments, the plasmid vector is pCK. In some embodiments, the IGF-1 encoding DNA construct is pCK-IGF-1X6 or pCK-IGF-1X10.

In some embodiments, the plasmid vector is pTx. In some embodiments, the IGF-1 encoding DNA construct is pTx-IGF-1X6 or pTx-IGF-1X10.

In other aspects, the present invention provides a pharmaceutical composition comprising the IGF-1 encoding DNA construct provided herein.

In other aspects, the present invention provides a pharmaceutical composition comprising the IGF-1 encoding DNA construct, wherein the IGF-1 encoding DNA construct encodes Class I IGF-1Ea protein comprising a polypeptide of SEQ ID NO: 14 or Class I IGF-1Ec protein comprising a polypeptide of SEQ ID NO: 16.

In some embodiments, the IGF-1 encoding DNA construct encodes both Class I IGF-1Ea protein comprising a polypeptide of SEQ ID NO: 14 and Class I IGF-1Ec protein comprising a polypeptide of SEQ ID NO: 16.

In some embodiments, the IGF-1 encoding DNA construct does not encode Class II IGF-1 Ea protein comprising a polypeptide of SEQ ID NO: 18 and Class I IGF-1Eb protein comprising a polypeptide of SEQ ID NO: 20.

In some embodiments, the IGF-1 encoding DNA construct encodes neither Class II IGF-1 Ea protein comprising a polypeptide of SEQ ID NO: 18 nor Class I IGF-1Eb protein comprising a polypeptide of SEQ ID NO: 20.

In some embodiments, the pharmaceutical composition comprises a first DNA construct encoding Class I IGF-1Ea protein comprising a polypeptide of SEQ ID NO: 14, and a second DNA construct encoding Class I IGF-1Ec protein comprising a polypeptide of SEQ ID NO: 16.

In some embodiments, the IGF-1 encoding DNA construct is pCK-IGF-1X6 or pCK-IGF-1X10. In some embodiments, the IGF-1 encoding DNA construct is pTx-IGF-1X6 or pTx-IGF-1X10.

Some aspects of the present invention provide a method of treating neuropathy, comprising the step of administering to a subject having neuropathy an effective amount of a first IGF-1 encoding DNA construct, wherein the first IGF-1 encoding DNA construct is capable of expressing at least one human IGF-1 isoform.

In some embodiments, the first IGF-1 encoding DNA construct is capable of expressing Class I IGF-1Ea protein comprising a polypeptide of SEQ ID NO: 14 or Class I IGF-1Ec protein comprising a polypeptide of SEQ ID NO: 16.

In some embodiments, the first IGF-1 encoding DNA construct is not capable of expressing Class II IGF-1 Ea protein comprising a polypeptide of SEQ ID NO: 18 or Class I IGF-1Eb protein comprising a polypeptide of SEQ ID NO: 20.

In some embodiments, the first IGF-1 encoding DNA construct comprises a polynucleotide of SEQ ID NO: 15. In some embodiments, the method further comprises the step of: administering to the subject a second IGF-1 encoding DNA construct, wherein the second IGF-1 encoding DNA construct comprises a polynucleotide of SEQ ID NO: 17.

In some embodiments, the first IGF-1 encoding DNA construct comprises a polynucleotide of SEQ ID NO: 17. In some embodiments, the method further comprises the step of: administering to the subject a second IGF-1 encoding DNA construct, wherein the second IGF-1 encoding DNA construct comprises a polynucleotide of SEQ ID NO: 15.

In some embodiments, the step of administering the first IGF-1 encoding DNA construct and the step of administering the second IGF-1 encoding DNA construct are performed concurrently.

In some embodiments, the step of administering the first IGF-1 encoding DNA construct and the step of administering the second IGF-1 encoding DNA construct are performed sequentially.

In some embodiments, the first IGF-1 encoding DNA construct encodes more than one human IGF-1 isoforms. In some embodiments, the first IGF-1 encoding DNA construct encodes Class I IGF-1Ea protein comprising a polypeptide of SEQ ID NO: 14 and Class I IGF-1 Ec protein comprising a polypeptide of SEQ ID NO: 16.

In some embodiments, the first IGF-1 encoding DNA construct comprises: a first polynucleotide that has the same sequence as exons 1, 3 and 4 of the human IGF-1 gene (SEQ ID NO: 1) or a degenerate thereof; a second polynucleotide that has the same sequence as intron 4 of the human IGF-1 gene (SEQ ID NO: 2) or a fragment thereof; a third polynucleotide that has the same sequence as exons 5 and 6-1 of the human IGF-1 gene (SEQ ID NO: 3) or a degenerate thereof; a fourth polynucleotide that has the same sequence as intron 5 of the human IGF-1 gene (SEQ ID NO: 4) or a fragment thereof; and a fifth polynucleotide that has the same sequence as exon 6-2 of the human IGF-1 gene (SEQ ID NO: 5) or a degenerate thereof, wherein the first polynucleotide, the second polynucleotide, the third polynucleotide, the fourth polynucleotide and the fifth polynucleotide are linked in sequential 5' to 3' order.

In some embodiments, the second polynucleotide is a polynucleotide of SEQ ID NO: 6. In some embodiments, the second polynucleotide is a polynucleotide of SEQ ID NO: 7.

In some embodiments, the fourth polynucleotide is a polynucleotide of SEQ ID NO: 8.

In some embodiments, the first IGF-1 encoding DNA construct comprises a plasmid vector. In some embodiments, the plasmid vector is pCK. In some embodiments, the plasmid vector is pTx.

In some embodiments, the first IGF-1 encoding DNA construct comprises a polynucleotide of SEQ ID NO: 10. In some embodiments, the first IGF-1 encoding DNA construct comprises a polynucleotide of SEQ ID NO: 9. In some embodiments, the first IGF-1 encoding DNA construct comprises a polynucleotide of SEQ ID NO: 27.

In some embodiments, the effective amount is an amount sufficient to reduce pain in the subject.

In some embodiments, the subject has neuropathic pain. In some embodiments, the subject has diabetic neuropathy.

In some embodiments, the step of administering the first IGF-1 encoding DNA construct or the second IGF-1 encoding DNA construct comprises an intramuscular injection.

In yet another aspect, the present disclosure provides an IGF-1 encoding DNA construct for use in a medical method of treating neuropathy, the method comprising the step of administering to a subject having neuropathy an effective amount of the IGF-1 encoding DNA construct, wherein the IGF-1 encoding DNA construct is capable of expressing at least one human IGF-1 isoform.

In some embodiments, the IGF-1 encoding DNA construct is capable of expressing Class I IGF-1Ea protein comprising a polypeptide of SEQ ID NO: 14 or Class I IGF-1Ec protein comprising a polypeptide of SEQ ID NO: 16. In some embodiments, the IGF-1 encoding DNA construct is not capable of expressing both Class II IGF-1 Ea protein comprising a polypeptide of SEQ ID NO: 18 and Class I IGF-1Eb protein comprising a polypeptide of SEQ ID NO: 20.

In some embodiments, the IGF-1 encoding DNA construct comprises a polynucleotide of SEQ ID NO: 15. In some embodiments, the medical method further comprises the step of: administering to the subject a second IGF-1 encoding DNA construct, wherein the second IGF-1 encoding DNA construct comprises a polynucleotide of SEQ ID NO: 17.

In some embodiments, the IGF-1 encoding DNA construct comprises a polynucleotide of SEQ ID NO: 17. In some embodiments, the medical method further comprising the step of: administering to the subject a second IGF-1 encoding DNA construct, wherein the second IGF-1 encoding DNA construct comprises a polynucleotide of SEQ ID NO: 15.

In some embodiments, the step of administering the IGF-1 encoding DNA construct and the step of administering the second IGF-1 encoding DNA construct are performed concurrently. In some embodiments, the step of administering the IGF-1 encoding DNA construct and the step of administering the second IGF-1 encoding DNA construct are performed sequentially.

In some embodiments, the IGF-1 encoding DNA construct encodes more than one human IGF-1 isoforms. In some embodiments, the IGF-1 encoding DNA construct encodes Class I IGF-1Ea protein comprising a polypeptide of SEQ ID NO: 14 and Class I IGF-1 Ec protein comprising a polypeptide of SEQ ID NO: 16.

In some embodiments, the IGF-1 encoding DNA construct comprises: a first polynucleotide that has the same sequence as exons 1, 3 and 4 of the human IGF-1 gene (SEQ ID NO: 1) or a degenerate thereof; a second polynucleotide that has the same sequence as intron 4 of the human IGF-1 gene (SEQ ID NO: 2) or a fragment thereof; a third polynucleotide that has the same sequence as exons 5 and 6-1 of the human IGF-1 gene (SEQ ID NO: 3) or a degenerate thereof; a fourth polynucleotide that has the same sequence as intron 5 of the human IGF-1 gene (SEQ ID NO: 4) or a fragment thereof; and a fifth polynucleotide that has the same sequence as exon 6-2 of the human IGF-1 gene (SEQ ID NO: 5) or a degenerate thereof, wherein the first polynucleotide, the second polynucleotide, the third polynucleotide, the fourth polynucleotide and the fifth polynucleotide are linked in sequential 5' to 3' order.

In some embodiments, the second polynucleotide is a polynucleotide of SEQ ID NO: 6. In some embodiments, the second polynucleotide is a polynucleotide of SEQ ID NO: 7. In some embodiments, the fourth polynucleotide is a polynucleotide of SEQ ID NO: 8.

In some embodiments, the IGF-1 encoding DNA construct comprises a plasmid vector. In some embodiments, the plasmid vector is pCK. In some embodiments, the plasmid vector is pTx.

In some embodiments, the IGF-1 encoding DNA construct comprises a polynucleotide of SEQ ID NO: 10. In some embodiments, the IGF-1 encoding DNA construct comprises a polynucleotide of SEQ ID NO: 9. In some embodiments, the IGF-1 encoding DNA construct comprises a polynucleotide of SEQ ID NO: 27

In some embodiments, the effective amount is an amount sufficient to reduce pain in the subject. In some embodiments, the subject has neuropathic pain. In some embodiments, the subject has diabetic neuropathy. In some embodiments, the step of administering the IGF-1 encoding DNA construct or the second IGF-1 encoding DNA construct comprises an intramuscular injection

5. BRIEF DESCRIPTION OF THE DRAWINGS

FIG. 1 is a schematic representation of the human IGF-1 gene including alternative transcription initiation sites and alternative splicing sites. IGF-1 isoforms that are naturally produced from the IGF-1 gene include Class I Ec (Isoform #1); Class II Ea (Isoform #2); Class I Eb (Isoform #3); and Class I Ea (Isoform #4).

FIG. 2A outlines the experimental protocol for testing therapeutic efficacy of various DNA constructs encoding an IGF-1 isoform in the chronic constriction injury (CCI) model.

FIG. 2B is a histogram showing the frequency of paw withdrawal measured in the Sham mice or CCI mice in the experiment outlined in FIG. 2A. The CCI mice were injected with a DNA construct—(i) pCK vector, (ii) pCK-IGF-1 #1 (a construct expressing Class I Ec isoform), (iii) pCK-IGF-1 #4 (a construct expressing Class I Ea isoform), or (iv) both pCK-IGF-1 #1 and pCK-IGF-1 #4.

FIG. 3A outlines the experimental protocol used in Example 2 to assess in vivo expression of IGF-1 isoforms from various DNA constructs.

FIG. 3B shows results of an ELISA measuring the amount of total human IGF-1 isoforms expressed after injection of a DNA construct encoding no IGF (vector only, "pCK"); a DNA construct encoding isoform #1 (Class I Ec isoform); a DNA construct encoding isoform #4 (Class I Ea isoform); two constructs, each encoding isoforms #1 (Class I Ec isoform) or #4 (Class I Ea isoform); and a dual expression construct pCK-IGF-1X6 or pCK-IGF-1X10.

Figure 4A:
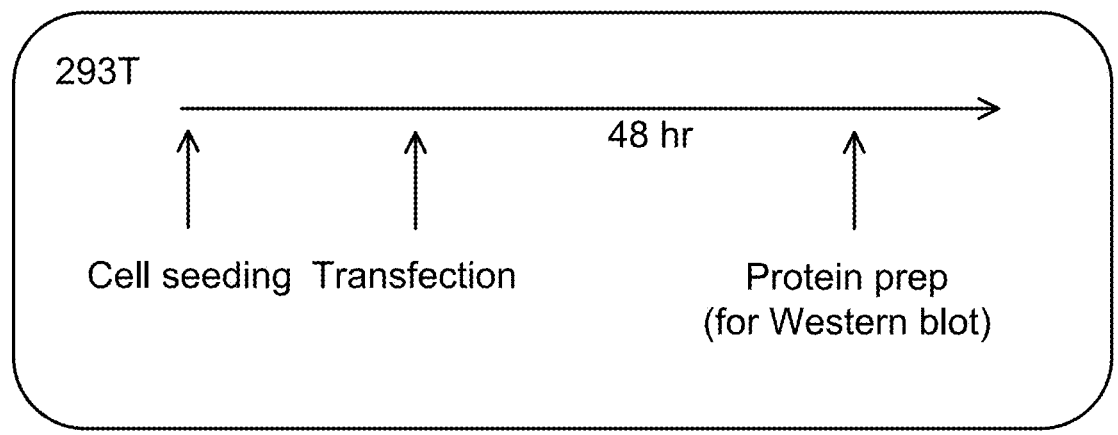

FIG. 4A outlines the protocol used in Example 2 to assess protein expression from the IGF-1 encoding DNA constructs in 293T cells in vitro.

Figure 4B:
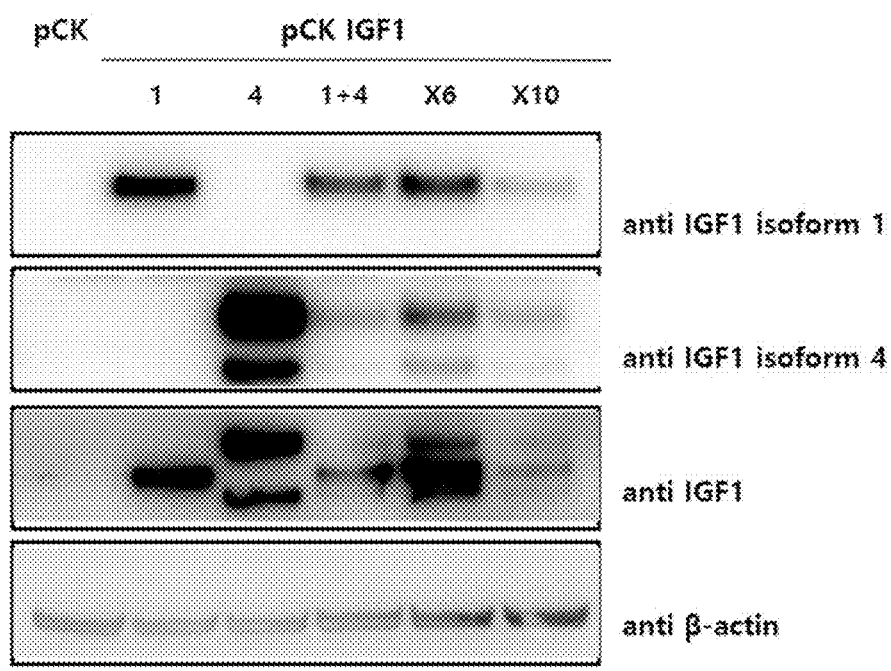

FIG. 4B shows western blotting results demonstrating expression of IGF-1 isoforms #1 and/or #4 after in vitro transfection of (i) a construct encoding isoform #1, (ii) a construct encoding isoform #4, (iii) two constructs, each encoding isoform #1 or #4, (iv) a dual expression vector pCK-IGF-1X6, or (v) a dual expression vector pCK-IGF-1X10.

Figure 5A:
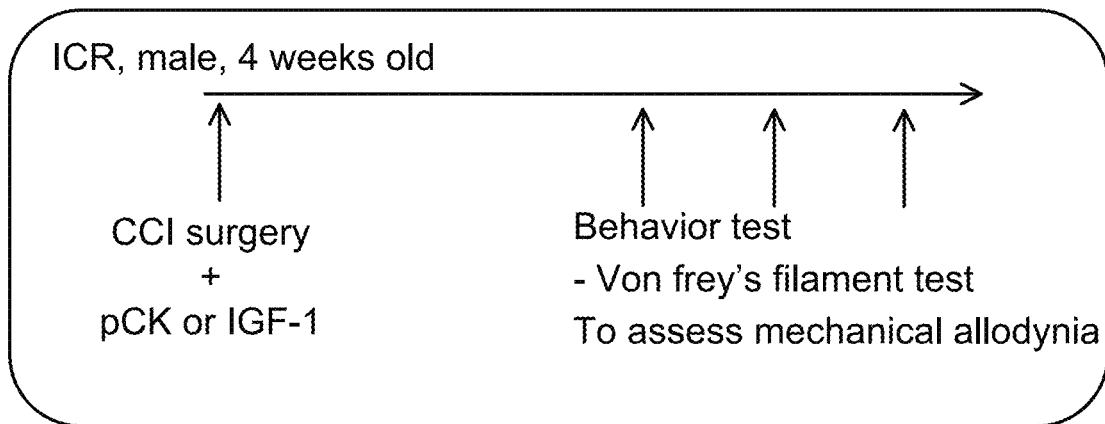

FIG. 5A outlines the experimental protocol used in Example 3 to test efficacy of various IGF-1 encoding DNA constructs in reducing mechanical allodynia in the CCI animal model.

Figure 5B:
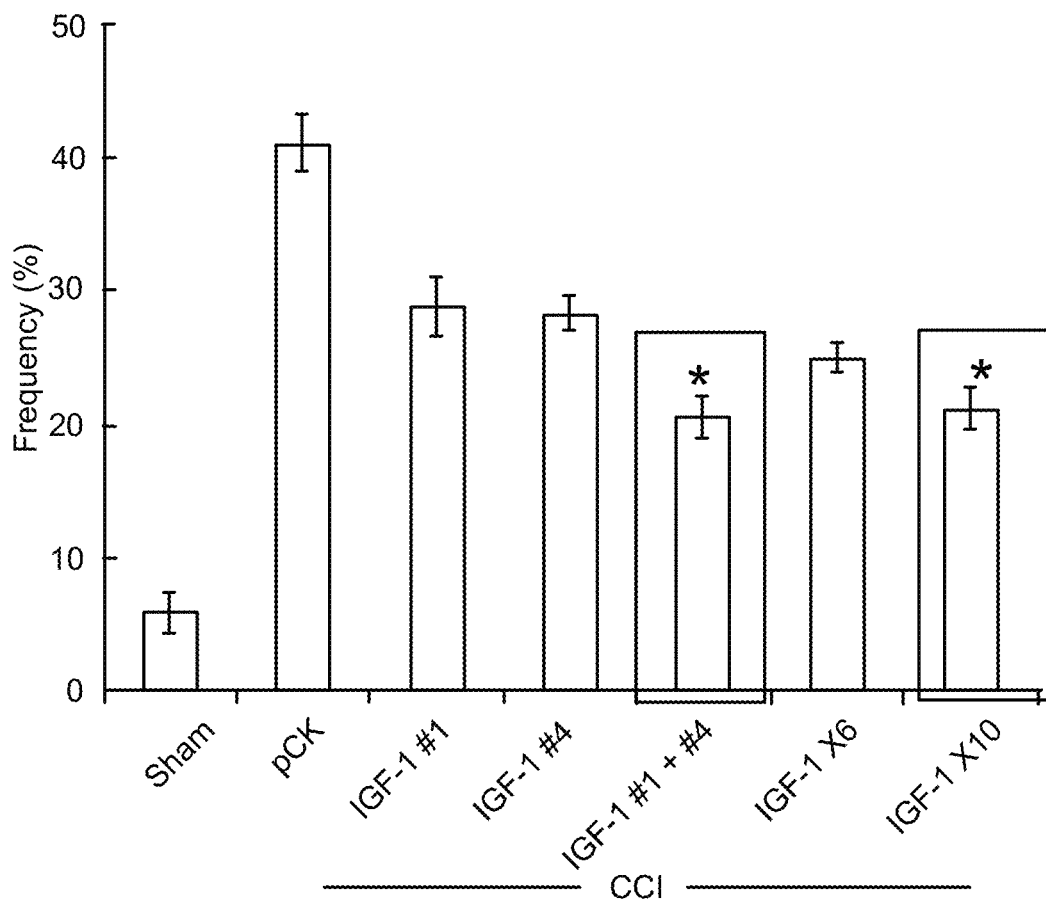

FIG. 5B is a histogram showing the frequency of paw withdrawal measured in the Sham mice or CCI mice in the experiment outlined in FIG. 5A. The CCI mice were injected with a DNA construct—(i) pCK vector, (ii) pCK-IGF-1 #1 (a construct expressing Class I Ec isoform), (iii) pCK-IGF-1 #4 (a construct expressing Class I Ea isoform), (iv) both pCK-IGF-1 #1 and pCK-IGF-1 #4, (v) a dual expression vector pCK-IGF-1X6, or (vi) a dual expression vector pCK-IGF-1X10.

Figure 6A:
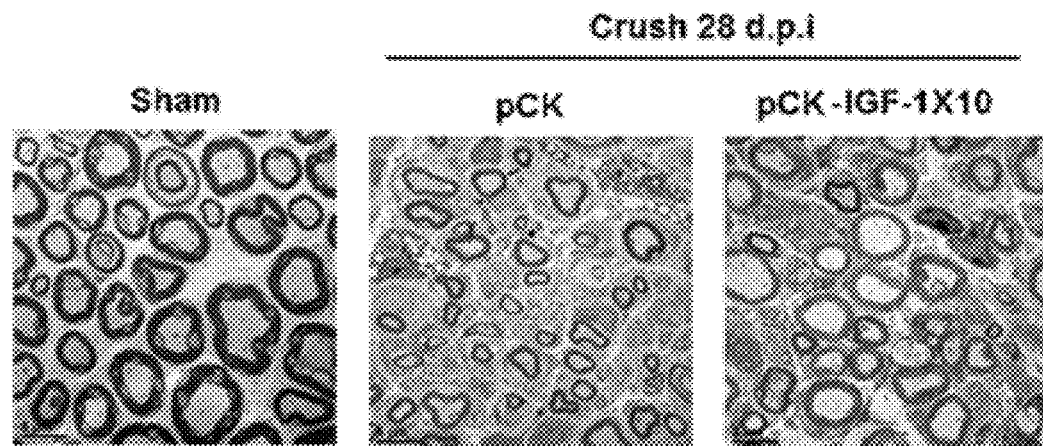

FIG. 6A provides transmission electron microscopic (TEM) images of the right ipsilateral sciatic nerve obtained from the Sham or the nerve crush animal model. The nerve crush animal model was injected with pCK vector or with a dual expression vector pCK-IGF-1X10.

Figure 6B:
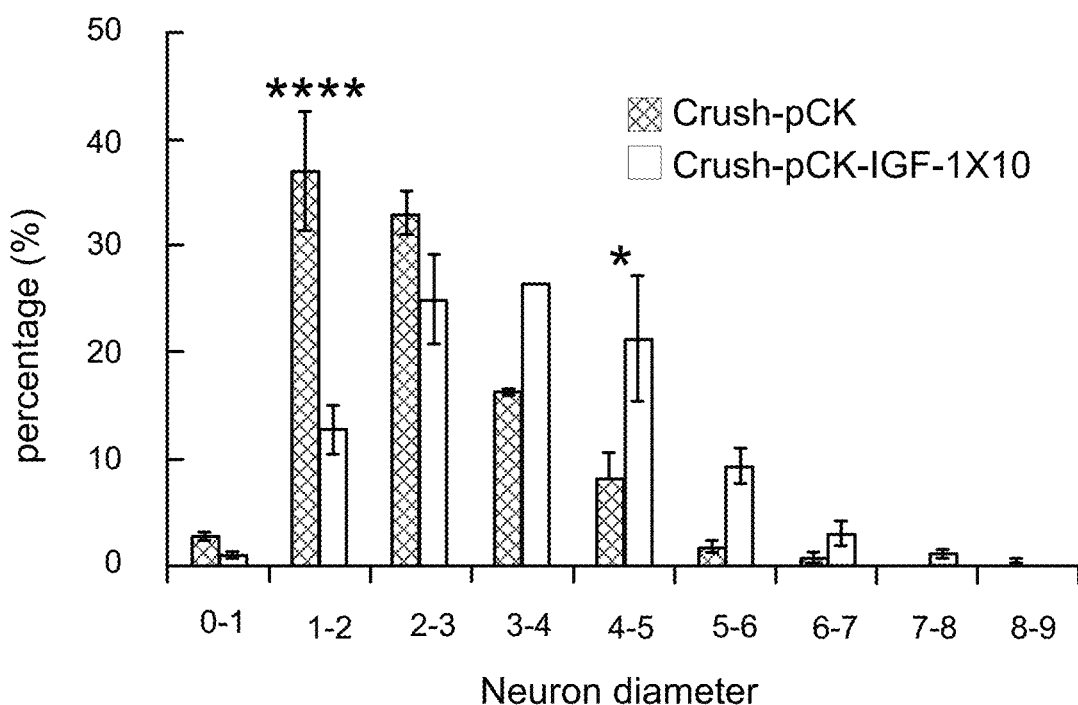

FIG. 6B is a graph showing distributions of neuron diameters in the nerve crush animal treated with pCK ("Crush-pCK") and a nerve crush animal treated with pCK-IGF-1X10 ("Crush-pCK-IGF-1X10").

The figures depict various embodiments of the present invention for purposes of illustration only. One skilled in the art will readily recognize from the following discussion that alternative embodiments of the structures and methods illustrated herein may be employed without departing from the principles of the invention described herein.

6. DETAILED DESCRIPTION

6.1. Definitions

Unless defined otherwise, all technical and scientific terms used herein have the meaning commonly understood by a person skilled in the art to which this invention belongs. As used herein, the following terms have the meanings ascribed to them below.

The terms "isoform of IGF-1," "human IGF-1 isoform" or "IGF-1 isoform" are used interchangeably herein to refer to a polypeptide having an amino acid sequence that is at least 80% identical to the amino acid sequence of one of naturally occurring pre-pro-IGF-1 polypeptides of humans, or their allelic variant, splice variant, or deletion variant. The naturally occurring pre-pro-IGF-1 polypeptides include Class I, Ec (SEQ ID NO: 16); Class II, Ea (SEQ ID NO: 18); Class I, Eb (SEQ ID NO: 20); and Class I, Ea isoforms (SEQ ID NO: 14).

The terms "Isoform #1," "Class I, Ec isoform," "Class I, IGF-1 Ec isoform" or "Class I, IGF-1 Ec" are used interchangeably herein to refer to a polypeptide of SEQ ID NO: 16.

The terms "Isoform #2," "Class II, Ea isoform," "Class II, IGF-1 Ea isoform" or "Class II, IGF-1 Ea" are used interchangeably herein to refer to a polypeptide of SEQ ID NO: 18.

The terms "Isoform #3," "Class I, Eb isoform," "Class I, IGF-1 Eb isoform" or "Class I, IGF-1 Eb" are used interchangeably herein to refer to a polypeptide of SEQ ID NO: 20.

The terms "Isoform #4," "Class I, Ea isoform," "Class I, IGF-1 Ea isoform" or "Class I, IGF-1 Ea" are used interchangeably herein to refer to a polypeptide of SEQ ID NO: 14.

The term "treatment" as used herein refers to all the acts of (a) suppression a symptom of neuropathy; (b) alleviation of a symptom of neuropathy; and (c) removal of a symptom of neuropathy. In some embodiments, the composition of the present invention can treat neuropathy through the growth of neuronal cells or the suppression of neuronal cell death.

The term "therapeutically effective dose" or "effective amount" as used herein refers to a dose or an amount that produces the desired effect for which it is administered. In the context of the present methods, a therapeutically effective amount is an amount effective to treat a symptom of neuropathy.

The term "sufficient amount" as used herein refers to an amount sufficient to produce a desired effect.

The term "degenerate sequence" or "degenerate" as used herein refers to a nucleic acid sequence that can be translated to provide an amino acid sequence identical to that translated from the reference nucleic acid sequence.

6.2. Other Interpretational Conventions

Ranges recited herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50

6.3. DNA Construct Expressing an IGF-1 Isoform

In a first aspect, DNA constructs encoding a human IGF-1 isoform is provided.

6.3.1. IGF-1 Isoforms

Figure 1:
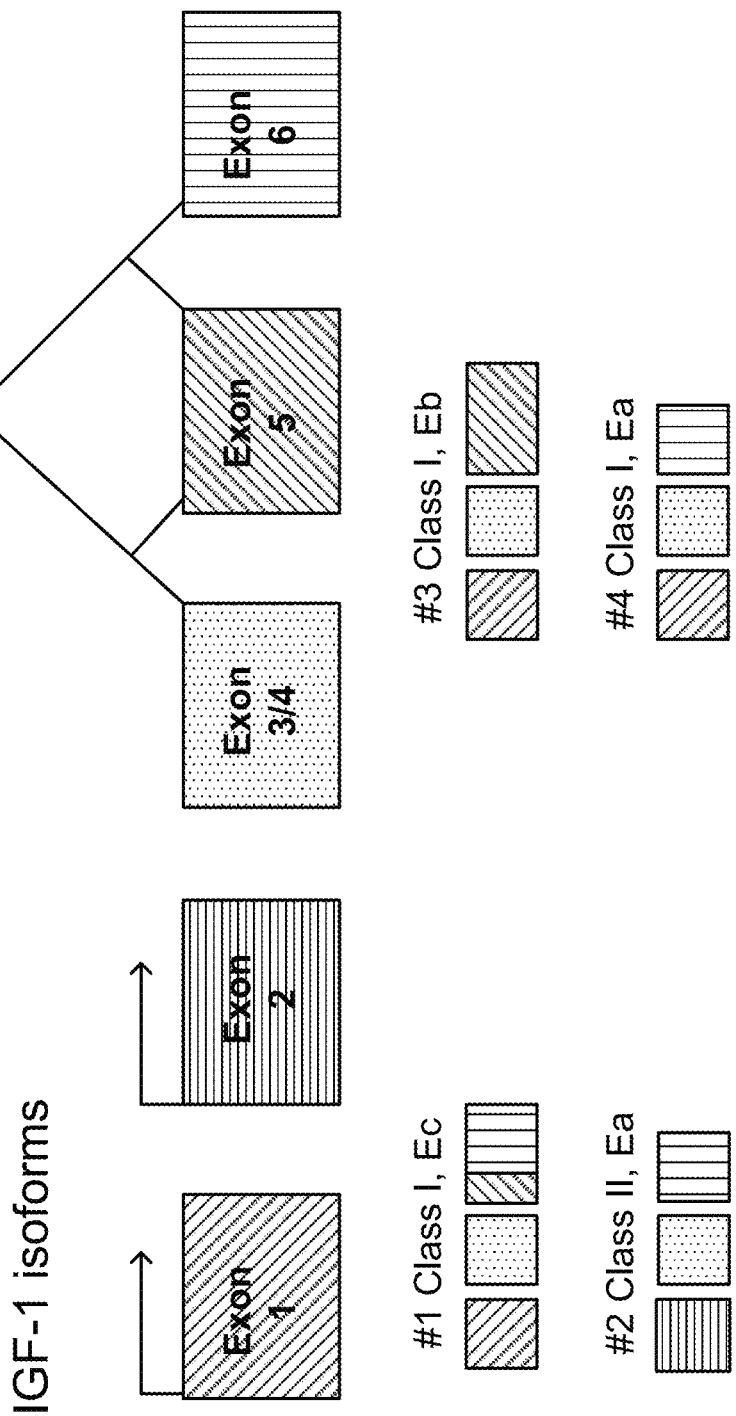

As illustrated in FIG. 1, the human IGF-1 gene contains six exons (exons 1, 2, 3, 4, 5, and 6 (6-1 and 6-2)) spanning nearly 90 kb of genomic DNA. Exons 1 and 2 are mutually exclusive leader exons, each having multiple promoter sites that are variably used. Further, the IGF-1 gene can be differentially spliced to create multiple transcript variants. Each transcript variant encodes a different pre-pro-IGF-1 protein ("IGF-1 isoform") possessing variable signaling peptide leader sequences. Yet all the transcript isoforms give rise to the same mature 70-amino acid IGF-1 peptide that uses the same receptor after processing.

The pre-pro-IGF-1 peptides differ in their leader, or signal, sequences and in their carboxy (C)-terminus. Incorporation of exon 1 or exon 2 is mutually exclusive and one of them serves as a leader sequence of the pre-pro-IGF-1 peptide; the different leader exons create different 5'-UTRs. The pre-pro-IGF-1 polypeptides undergo posttranscriptional proteolytic cleavage to remove the leader and the E-peptide carboxy-terminus giving rise to the mature 70-amino acid IGF-1.

Transcripts containing exon 1 are referred to as Class 1 transcripts (e.g., Class I, Ec; Class I, Eb; and Class I, Ea in FIG. 1) whereas those containing exon 2 are referred to as Class 2 transcripts (e.g., Class II, Ea in FIG. 1). Nearly all pre-pro peptides include 27 amino acids in the signaling peptide derived from exon 3 with the remaining signal sequences derived from the inclusion of exon 1 or 2. A minority of transcripts utilize a different transcription initiation site within exon 3 generating a shorter signaling peptide of 22 amino acids. Exons 3 and 4 are invariant and encode the B, C, A, and D domains of the mature IGF-1 peptide; exon 4 encodes two thirds of the mature IGF-1 peptide. The human Eb peptide is composed of only exons 4 and 5 whereas Ec contains exons 4, 5, and 6.

Alternative splicing and mutually exclusive initiation of transcription are illustrated in FIG. 1 that result in generation of different pre-pro-IGF-1 polypeptides (i.e., IGF-1 isoforms). Specifically, Class I, Ec IGF-1 isoform (SEQ ID NO: 16), comprising at least a fragment of exons 1, 3/4, 5 and 6, is generated from a transcript comprising a sequence of SEQ ID NO: 17. Class II, Ea IGF-1 isoform (SEQ ID NO:18), comprising at least a fragment of exons 2, 3/4 and 6, is generated from a transcript comprising a sequence of SEQ ID NO:19. Class I, Eb IGF-1 isoform (SEQ ID NO:20), comprising at least a fragment of exons 1, 3/4 and 5, is generated from a transcript comprising a sequence of SEQ ID NO:21. Class I, Ea IGF-1 isoform (SEQ ID NO:14), comprising at least a fragment of exons 1, 3/4 and 6 are generated from a transcript comprising a sequence of SEQ ID NO: 15.

Although the mature IGF-1 protein derived from the various transcripts does not differ, the various transcript isoforms have been suggested to have different regulatory roles. The variant forms possess different stabilities, binding partners, and activity indicating a pivotal regulatory role for the isoforms. The biological significance of the isoforms remains unclear, although it has been hypothesized that Class I isoforms with exon 1 are autocrine/paracrine forms while Class II isoforms with exon 2 are secreted endocrine forms. This is based on the finding that Class II transcripts include a typical signal peptide motif associated with efficient secretion, whereas Class I transcripts have a longer signal peptide that can possibly interfere with secretion.

Most tissues are believed to use Class I transcripts, although liver uses both forms and hepatic Class II transcripts are preferentially enhanced during development.

There are many changes in the IGF-1 transcript abundance during development. It was found that Class 1, Ea is the most abundant form during the active growth phase and Class 1, Eb is also expressed uniformly, albeit at lower levels, across the growth plate during early growth phases.

6.3.2. DNA Construct Expressing IGF-1 Isoform

In an aspect, the present invention provides DNA constructs capable of expressing at least one isoform of human IGF-1. In some embodiments, more than one DNA constructs, each encoding a different IGF-1 isoform, are used. For example, a first construct encoding Class I, Ec isoform (Isoform #1) and a second construct encoding Class I, Ea isoform (Isoform #4) are used together. In some embodiments, a DNA construct that expresses two or more isoforms (i.e., "a dual expression construct") is used. For example, a single DNA construct encoding both Class I, Ec isoform and Class I, Ea isoform can be used.

6.3.2.1. IGF-1 Encoding Sequences

In some embodiment, the DNA construct contains a coding sequence of one of the IGF-1 isoforms. For example, the DNA construct can comprise a sequence encoding Class I, Ea (SEQ ID NO: 15); Class I, Eb (SEQ ID NO:21); Class I, Ec (SEQ ID NO:17); or Class II, Ea (SEQ ID NO:19).

In some embodiments, the DNA construct is a dual expression construct, a DNA construct that can express more than one IGF-1 isoforms, by comprising an expression regulatory sequence for each isoform coding sequence (CDS). In some embodiments, the construct comprises an internal ribosomal entry site (IRES) between two coding sequences, for example, in the order of (1) expression regulatory sequence—(2) coding sequence of first isoform—(3) IRES—(4) coding sequence of second isoform—(5) transcription termination sequence. IRES allows translation to start at the IRES sequence, thereby allowing expression of two protein products from a single transcript. In yet further embodiments, a plurality of constructs, each encoding a single isoform of IGF-1, are used together to induce expression of more than one isoforms of IGF-1 in the subject to whom administered.

In preferred embodiments, a DNA construct is capable of expressing two or more IGF-1 isoforms simultaneously—e.g., (i) Class I, Ec isoform (Isoform #1) and Class II, Ea isoform (Isoform #2); (ii) Class I, Ec isoform (Isoform #1) and Class I, Eb isoform (Isoform #3); (iii) Class I, Ec isoform (Isoform #1) and Class I, Ea isoform (Isoform #4); (iv) Class II, Ea isoform (Isoform #2) and Class I, Eb isoform (Isoform #3); (v) Class II, Ea isoform (Isoform #2) and Class I, Ea isoform (Isoform #4); (vi) Class I, Eb isoform (Isoform #3) and Class I, Ea isoform (Isoform #4)—by comprising an alternative splicing site.

For example, the DNA construct can comprise (i) a first sequence comprising exons 1, 3 and 4 of a human IGF-1 gene (SEQ ID NO:1) or a degenerate sequence of the first sequence; (ii) a second sequence comprising intron 4 of the human IGF-1 gene (SEQ ID NO:2) or a fragment of the second sequence; (iii) a third sequence comprising exons 5 and 6-1 of the human IGF-1 gene (SEQ ID NO:3) or a degenerate sequence of the third sequence; (iv) a fourth sequence comprising intron 5 of the human IGF-1 gene (SEQ ID NO:4) or a fragment of the second sequence; and (v) a fifth sequence comprising exon 6-2 of the human IGF-1 gene (SEQ ID NO:5) or a degenerate sequence of the fifth sequence. Introns 4 and 5 can be alternatively spliced, resulting in production of two isoforms of IGF-1 (e.g., Class I, Ec and Class I, Ea).

In some embodiments, the DNA construct is tested in vitro and/or in vivo related to its capability to express one or more IGF-1 isoforms. In preferred embodiments, DNA constructs capable of expressing both Class I, Ec and Class I, Ea IGF-1 isoforms are selected.

In some embodiments, the construct comprises a full sequence of intron 4 (SEQ ID NO:2) or its fragment. In preferred embodiments, the construct comprises a fragment of intron 4 having a sequence of SEQ ID NO: 6 or SEQ ID NO: 7.

In some embodiments, the construct comprises a full sequence of intron 5 (SEQ ID NO: 4), or its fragment. In preferred embodiments, the construct comprises a fragment of intron 5 having a sequence of SEQ ID NO: 8.

Various DNA constructs comprising cDNA corresponding (i) exons 1-6 of the human IGF-1 gene and (ii) introns 4 and 5 of the human IGF-1 gene or various fragments of introns 4 and 5 are named "IGF-1X" followed by a unique number. The IGF-1X constructs tested by Applicant include, but are not limited to, IGF-1X1, IGF-1X2, IGF-1X3, IGF-1X4, IGF-1X5, IGF-1X6, IGF-1X7, IGF-1X8, IGF-1X9 and IGF-1X10. Among the tested constructs, IGF-1X6 and IGF-1X10 were identified to express both Class I, Ec and Class I, Ea IGF-1 isoforms.

In preferred embodiments, IGF-1X6 (SEQ ID NO:9) or IGF-1X10 (SEQ ID NO:10) is used. IGF-1X6 (SEQ ID NO:9) and IGF-1X10 (SEQ ID NO:10) cloned into a pCK vector are named pCK-IGF-1X6 and pCK-IGF-1X10, respectively. E.coli cells transformed with pCK-IGF-1X6 ("DH5α_pCK-IGF1 X6") were deposited under the terms of the Budapest Treaty at the Korea Collection for Type Cultures (KCTC, Korea Research Institute of Bioscience and Biotechnology (KRIBB) 181, Ipsin-gil, Jeongeup-si, Jeollabuk-do, 56212, Republic of Korea) with accession number KCTC 13539BP on May 30, 2018. E. coli cells transformed with pCK-GF-1X10 ("DH5α_pCK-IGF1 X10") were deposited under the terms of the Budapest Treaty at the Korea Collection for Type Cultures (KCTC, Korea Research Institute of Bioscience and Biotechnology (KRIBB) 181, Ipsin-gil, Jeongeup-si, Jeollabuk-do, 56212, Republic of Korea) with accession number KCTC 13540BP on May 30, 2018.

In other preferred embodiments, IGF-1X6 (SEQ ID NO:9) and IGF-1X10 (SEQ ID NO:10) are cloned into a pTx vector. The IGF constructs are named pTx-IGF-1X6 and pTx-IGF-1X10, respectively.

IGF-1 isoforms or DNA constructs encoding IGF-1 isoforms described herein can include modifications from the wild type human IGF-1 isoforms. The modified sequences can include sequences with at least 80% identity, more preferably at least 90% identity and most preferably at least 95% identity when the modified sequences are aligned with the wild type human IGF-1 isoform sequences in the maximal manner. Methods of alignment of sequences for comparison are well-known in the art. Specifically, alignment algorithm disclosed in the NCBI Basic Local Alignment Search Tool (BLAST) of the National Center for Biological Information (NBCl, Bethesda, Md.) website and used in connection with the sequence analysis programs blastp, blasm, blastx, tblastn and tblastx can be used to determine the percent identity.

6.3.2.2. Vector

DNA constructs expressing an IGF-1 isoform of the present invention typically comprise a vector with one or more regulatory sequences (e.g., a promoter or an enhancer) operatively linked to the expressed sequences. The regulatory sequence regulates expression of the isoforms of IGF-1.

It is preferred that the polynucleotide encoding one or more isoforms of IGF-1 isoforms is operatively linked to a promoter in an expression construct. The term "operatively linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

In typical embodiments, the promoter linked to the polynucleotide is operable in, preferably, animal, more preferably, mammalian cells, to control transcription of the polynucleotide, including the promoters derived from the genome of mammalian cells or from mammalian viruses, for example, CMV (cytomegalovirus) promoter, the adenovirus late promoter, the vaccinia virus 7.5 K promoter, SV40 promoter, HSV tk promoter, RSV promoter, EF1 alpha promoter, metallothionein promoter, beta-actin promoter, human IL-2 gene promoter, human IFN gene promoter, human IL-4 gene promoter, human lymphotoxin gene promoter and human GM-CSF gene promoter, but not limited to. More preferably, the promoter useful in this invention is a promoter derived from the IE (immediately early) gene of human CMV (hCMV) or EF1 alpha promoter, most preferably hCMV IE gene-derived promoter/enhancer and 5'-UTR (untranslated region) comprising the overall sequence of exon 1 and exon 2 sequence spanning a sequence immediately before the ATG start codon.

The expression cassette used in this invention can comprise a polyadenylation sequence, for example, including bovine growth hormone terminator (Gimmi, E. R., et al., Nucleic Acids Res. 17:6983-6998 (1989)), SV40-derived polyadenylation sequence (Schek, N, et al., Mol. Cell Biol. 12:5386-5393 (1992)), HIV-1 polyA (Klasens, B. I. F., et al., Nucleic Acids Res. 26:1870-1876 (1998)), β-globin polyA (Gil, A., et al, Cell 49:399-406 (1987)), HSV TK polyA (Cole, C. N. and T. P. Stacy, Mol. Cell. 5 Biol. 5: 2104-2113 (1985)) or polyoma virus polyA (Batt, D. Band G. G. Carmichael, Mol. Cell. Biol. 15:4783-4790 (1995)), but not limited thereto.

6.3.2.3. Non-Viral Vector

In some embodiments, the DNA construct is a non-viral vector capable of expressing one or more isoforms of IGF-1.

In typical embodiments, the non-viral vector is a plasmid. In currently preferred embodiments, the plasmid is pCK, pCP, pVAX1, pTx or pCY. In particularly preferred embodiments, the plasmid is pCK, details of which can be found in WO 2000/040737 and Lee et al., Biochem. Biophys. Res. Comm. 272:230-235 (2000), both of which are incorporated herein by reference in their entireties. E. coli transformed with pCK (Top10-pCK) was deposited at the Korean Culture Center of Microorganisms (KCCM) under the terms of the Budapest Treaty on Mar. 21, 2003 (Accession NO: KCCM-10476). E. coli transformed with pCK-VEGF165 (i.e., pCK vector with VEGF coding sequence—Top10-pCK-NEGF165') was deposited at the Korean Culture Center of Microorganisms (KCCM) under the terms of the Budapest Treaty on Dec. 27, 1999 (Accession NO: KCCM-10179).

The pCK vector is constructed such that the expression of a gene, e.g., an IGF-1 gene, is regulated under enhancer/promoter of the human cytomegalovirus (HCMV), as disclosed in detail in Lee et al., Biochem. Biophys. Res. Commun. 272: 230 (2000); WO 2000/040737, both of which are incorporated by reference in their entirety. pCK vector has been used for clinical trials on human body, and its safety and efficacy were confirmed (Henry et al., Gene Ther. 18:788 (2011)).

In preferred embodiments, the pCK plasmid contains a coding sequence for Class I, Ec IGF-1 isoform and/or Class I, Ea IGF-1 isoform. In particularly preferred embodiments, the pCK plasmid contains IGF-1X6 (i.e., pCK-IGF-1X6) or IGF-1 X10 (i.e., pCK-IGF-1X10).

In other preferred embodiments, the plasmid is pTx (SEQ ID NO: 26), a plasmid vector derived from pCK. pTx was generated by two sequential rounds of mutagenesis of pCK. The first deletion mutagenesis campaign was conducted to remove the unnecessary sequence between Kanamycin resistance gene and ColE1 of pCK. Specifically, deletion mutagenesis PCR was performed using a first primer pair (SEQ ID NOs: 22 and 23). The deletion of 228 base pairs between Kanamycin resistance and ColE1 was confirmed by sequencing the plasmid. The second deletion mutagenesis campaign was then performed using a second primer pair (SEQ ID NOs: 24 and 25), to optimize the size of HCMV intron sequence. HCMV intron sequence (421 base pairs) between IE1 exon 1 and exon 2 was deleted and the deletion was confirmed by sequencing.

In particular embodiments, the pTx plasmid contains IGF-1X6 (i.e., pTx-IGF-1X6) or IGF-1 X10 (i.e., pTx-IGF-1X10). For example, pTx-1X10 (SEQ ID NOs: 27) was generated by ligating IGF-1X10 in pTx digested with ClaI enzyme at 5' and SalI enzyme at 3'.

6.3.2.4. Viral Vector

In other embodiments, various viral vectors known in the art can be used to deliver and express one or more IGF-1 isoforms of the present invention. For example, vectors developed using retroviruses, lentiviruses, adenoviruses, or adeno-associated viruses can be used for some embodiments of the present invention.

(a) Retrovirus

Retroviruses capable of carrying relatively large exogenous genes have been used as viral gene delivery vectors in the senses that they integrate their genome into a host genome and have broad host spectrum.

In order to construct a retroviral vector, the polynucleotide of the invention (e.g., a coding sequence of one or more IGF-1 isoforms) is inserted into the viral genome in the place of certain viral sequences to produce a replication-defective virus. To produce virions, a packaging cell line containing the gag, pol and env genes but without the LTR (long terminal repeat) and W components is constructed (Mann et al., Cell, 33:153-159 (1983)). When a recombinant plasmid containing the polynucleotide of the invention, LTR and W is introduced into this cell line, the W sequence allows the RNA transcript of the recombinant plasmid to be packaged into viral particles, which are then secreted into the culture media (Nicolas and Rubinstein "Retroviral vectors," In: Vectors: A survey of molecular cloning vectors and their uses, Rodriguez and Denhardt (eds.), Stoneham: Butterworth, 494-513(1988)) The media containing the recombinant retroviruses is then collected, optionally concentrated and used for gene delivery.

A successful gene transfer using the second generation retroviral vector has been reported. Kasahara et al. (Science, 266:1373-1376 (1994)) prepared variants of moloney murine leukemia virus in which the EPO (erythropoietin) sequence is inserted in the place of the envelope region, consequently, producing chimeric proteins having novel binding properties. Likely, the present gene delivery system can be constructed in accordance with the construction strategies for the second-generation retroviral vector.

(b) Lentiviruses

Lentiviruses can be also used in some embodiments of the present invention. Lentiviruses are a subclass of Retroviruses. However, Lentivirus can integrate into the genome of non-dividing cells, while Retroviruses can infect only dividing cells.

Lentiviral vectors are usually produced from packaging cell line, commonly HEK293, transformed with several plasmids. The plasmids include (1) packaging plasmids encoding the virion proteins such as capsid and the reverse transcriptase, (2) a plasmid comprising an exogenous gene (e.g., a coding sequence of one or more IGF-1 isoforms) to be delivered to the target.

When the virus enters the cell, the viral genome in the form of RNA is reverse-transcribed to produce DNA, which is then inserted into the genome by the viral integrase enzyme. Thus, the exogenous delivered with the Lentiviral vector can remain in the genome and is passed on to the progeny of the cell when it divides.

(c) Adenovirus

Adenovirus has been usually employed as a gene delivery system because of its mid-sized genome, ease of manipulation, high titer, wide target-cell range, and high infectivity. Both ends of the viral genome contains 100-200 bp ITRs (inverted terminal repeats), which are cis-elements necessary for viral DNA replication and packaging. The E1 region (E1A and E1B) encodes proteins responsible for the regulation of transcription of the viral genome and a few cellular genes. The expression of the E2 region (E2A and E2B) results in the synthesis of the proteins for viral DNA replication.

Of adenoviral vectors developed so far, the replication incompetent adenovirus having the deleted E1 region is usually used. The deleted E3 region in adenoviral vectors may provide an insertion site for transgenes (Thimmappaya, B. et al., Cell, 31:543-551(1982); and Riordan, J. R. et al., Science, 245:1066- 1073 (1989)). Therefore, it is preferred that the decorin-encoding nucleotide sequence is inserted into either the deleted E1 region (E1A region and/or E1B 5 region, preferably, E1B region) or the deleted E3 region. The polynucleotide of the invention may be inserted into the deleted E4 region. The term "deletion" with reference to viral genome sequences encompasses whole deletion and partial deletion as well. In nature, adenovirus can package approximately 105% of the wildtype genome, providing capacity for about 2 extra kb of DNA (Ghosh-Choudhury et al., EMBO J. 6:1733- 1 739 (1987)). In this regard, the foreign sequences described above inserted into adenovirus may be further inserted into adenoviral wild-type genome.

The adenovirus may be of any of the known serotypes or subgroups A-F. Adenovirus type 5 of subgroup C is the most preferred starting material for constructing the adenoviral gene delivery system of this invention. A great deal of biochemical and genetic information about adenovirus type 5 is known. The foreign genes delivered by the adenoviral gene delivery system are episomal, and genotoxicity to host cells. Therefore, gene therapy using the adenoviral gene delivery system may be considerably safe.

(d) Adeno-Associated Virus (AAV)

Adeno-associated viruses are capable of infecting non-dividing cells and various types of cells, making them useful in constructing the gene delivery system of this invention. Detailed descriptions for use and preparation of AAV vectors are found in U.S. Pat. Nos. 10,308,958; 10,301,650; 10,301, 648; 10,266,846; 10,265,417; 10,208,107; 10,167,454; 10,155,931; 10,149,873; 10,144,770; 10,138,295; 10,137, 176; 10,113,182; 10,041,090; 9,890,365; 9,790,472; 9,770, 011; 9,738,688; 9,737,618; 9,719,106; 9,677,089; 9,617, 561; 9,597,363; 9,593,346; 9,587,250; 9,567,607; 9,493, 788; 9,382,551; 9,359,618; 9,217,159; 9,206,238; 9,163, 260; 9,133,483; 8,962,332, the disclosures of which are incorporated herein by reference in their entireties, and 5,139,941 and 4,797,368, the disclosures of which are incorporated herein by reference in their entireties.

Research results for AAV as gene delivery systems are disclosed in LaFace et al., Viology, 162: 483486 (1988), Zhou et al., Exp. Hematol. (NY), 21:928-933(1993), Walsh et al., J. Clin. Invest., 94:1440-1448(1994) and Flotte et al., Gene Therapy, 2:29-37(1995). Typically, a recombinant AAV virus is made by cotransfecting a plasmid containing the gene of interest (i.e., nucleotide sequence of interest to be delivered, e.g., a coding sequence of an IGF-1 isoform) flanked by the two AAV terminal repeats (McLaughlin et al., 1988; Samulski et al., 1989) and an expression plasmid containing the wild type AAV coding sequences without the terminal repeats (McCarty et al., J. Viral., 65:2936-2945 (1991)).

(e) Other Viral Vectors

Other viral vectors may be employed as a gene delivery system in the present invention. Vectors derived from viruses such as vaccinia virus (Puhlmann M. et al., Human Gene Therapy 10:649-657(1999); Ridgeway, "Mammalian expression vectors," In: Vectors: A survey of molecular cloning vectors and their uses. Rodriguez and Denhardt, eds. Stoneham: Butterworth, 467-492 (1988); Baichwal and Sugden, "Vectors for gene transfer derived from animal DNA viruses: Transient and stable expression of transferred genes," In: Kucherlapati R, ed. Gene transfer. New York: Plenum Press, 117-148 (1986) and Coupar et al., Gene, 68:1-10(1988)), lentivirus (Wang G. et al., J. Clin. Invest. 104 (11): RS 5-62 (1999)) and herpes simplex virus (Chamber R., et al., Proc. Natl. 10 15 Acad. Sci USA 92:1411-1415(1995)) may be used in the present delivery systems for transferring the polynucleotide of the invention into cells.

6.4. Pharmaceutical Composition Comprising IGF-1 Encoding DNA Construct

In another aspect, a pharmaceutical composition comprising the IGF-1 encoding DNA construct is provided.

6.4.1. Pharmacological Compositions and Unit Dosage Forms Adapted for Injection

For intravenous, intramuscular, intradermal, or subcutaneous injection, the DNA construct can be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives, as required.

In some embodiments, the pharmaceutical composition comprises a DNA construct encoding one IGF-1 isoform. For example, the DNA construct can express Class I, Ec isoform (Isoform #1); Class II, Ea isoform (Isoform #2); Class I, Eb isoform (Isoform #3); or Class I, Ea isoform (Isoform #4).

In some embodiments, the pharmaceutical composition comprises more than one DNA constructs, each encoding one IGF-1 isoform. For example, the pharmaceutical composition can comprise (i) a first DNA construct encoding Class I, Ec isoform (Isoform #1) and a second DNA construct encoding Class II, Ea isoform (Isoform #2); (ii) a first DNA construct encoding Class I, Ec isoform (Isoform #1) and a second DNA construct encoding Class I, Eb isoform (Isoform #3); (iii) a first DNA construct encoding Class I, Ec isoform (Isoform #1) and a second DNA construct encoding Class I, Ea isoform (Isoform #4); (iv) a first DNA construct encoding Class II, Ea isoform (Isoform #2) and a second DNA construct encoding Class I, Eb isoform (Isoform #3); (v) a first DNA construct encoding Class II, Ea isoform (Isoform #2) and a second DNA construct encoding Class I, Ea isoform (Isoform #4); (vi) a first DNA construct encoding Class I, Eb isoform (Isoform #3) and a second DNA construct encoding Class I, Ea isoform (Isoform #4).

In some embodiments, the pharmaceutical composition comprises a dual expression construct, a DNA construct that can express more than one IGF-1 isoforms. For example, the pharmaceutical composition can comprise a dual expression construct that can express (i) Class I, Ec isoform (Isoform #1) and Class II, Ea isoform (Isoform #2); (ii) Class I, Ec isoform (Isoform #1) and Class I, Eb isoform (Isoform #3); (iii) Class I, Ec isoform (Isoform #1) and Class I, Ea isoform (Isoform #4); (iv) Class II, Ea isoform (Isoform #2) and Class I, Eb isoform (Isoform #3); (v) Class II, Ea isoform (Isoform #2) and Class I, Ea isoform (Isoform #4); (vi) Class I, Eb isoform (Isoform #3) and Class I, Ea isoform (Isoform #4).

In some embodiments, the pharmaceutical composition comprises a dual expression construct, pCK-IGF-1X6 or pCK-IGF-1X10. In some embodiments, the pharmaceutical composition comprises a dual expression construct, pTx-IGF-1X6 or pTx-IGF-1X10. In some embodiments, the pharmaceutical composition comprises two dual expression constructs, for example, including both pCK-IGF-1X6 and pCK-IGF-1X10. In some embodiments, the pharmaceutical composition comprises two dual expression constructs, for example, including both pTx-IGF-1X6 and pTx-IGF-1X10.

In some embodiments, the pharmaceutical composition further comprises another therapeutic agent. For example, the pharmaceutical composition can further comprise another therapeutic agent effective in treating neuropathy.

In various embodiments, the DNA construct is present in the liquid composition at a concentration of 0.01 mg/ml, 0.05 mg/ml, 0.1 mg/ml, 0.25 mg/ml, 0.45 mg/ml, 0.5 mg/ml, or 1 mg/ml. In some embodiments, the unit dosage form is a vial containing 2 ml of the pharmaceutical composition at a concentration of 0.01 mg/ml, 0.1 mg/ml, 0.5 mg/ml, or 1 mg/ml. In some embodiments, the unit dosage form is a vial containing 1 ml of the pharmaceutical composition at a concentration of 0.01 mg/ml, 0.1 mg/ml, 0.5 mg/ml, or 1 mg/ml. In some embodiments, the unit dosage form is a vial containing less than 1 ml of the pharmaceutical composition at a concentration of 0.01 mg/ml, 0.1 mg/ml, 0.5 mg/ml, or 1 mg/ml.

In some embodiments, the unit dosage form is a vial, ampule, bottle, or pre-filled syringe. In some embodiments, the unit dosage form contains 0.01 mg, 0.1 mg, 0.2 mg, 0.25 mg, 0.5 mg, 1 mg, 2.5 mg, 5 mg, 8 mg, 10 mg, 12.5 mg, 16 mg, 24 mg, 25 mg, 50 mg, 75 mg, 100 mg, 150 mg, or 200 mg of the DNA construct of the present invention.

In some embodiments, the pharmaceutical composition in the unit dosage form is in liquid form. In various embodiments, the unit dosage form contains between 0.1 ml and 50 ml of the pharmaceutical composition. In some embodiments, the unit dosage form contains 0.25 ml, 0.5 ml, 1 ml, 2.5 ml, 5 ml, 7.5 ml, 10 ml, 25 ml, or 50 ml of pharmaceutical composition.

In particular embodiments, the unit dosage form is a vial containing 0.5 ml, 1 ml, 1.5 ml or 2 ml of the pharmaceutical composition at unit dosage form embodiments suitable for subcutaneous, intradermal, or intramuscular administration include preloaded syringes, auto-injectors, and auto-inject pens, each containing a predetermined amount of the pharmaceutical composition described hereinabove.

In various embodiments, the unit dosage form is a preloaded syringe, comprising a syringe and a predetermined amount of the pharmaceutical composition. In certain preloaded syringe embodiments, the syringe is adapted for subcutaneous administration. In certain embodiments, the syringe is suitable for self-administration. In particular embodiments, the preloaded syringe is a single-use syringe.

In various embodiments, the preloaded syringe contains about 0.1 mL to about 0.5 mL of the pharmaceutical composition. In certain embodiments, the syringe contains about 0.5 mL of the pharmaceutical composition. In specific embodiments, the syringe contains about 1.0 mL of the pharmaceutical composition. In particular embodiments, the syringe contains about 2.0 mL of the pharmaceutical composition.

In certain embodiments, the unit dosage form is an auto-inject pen. The auto-inject pen comprises an auto-inject pen containing a pharmaceutical composition as described herein. In some embodiments, the auto-inject pen delivers a predetermined volume of pharmaceutical composition. In other embodiments, the auto-inject pen is configured to deliver a volume of pharmaceutical composition set by the user.

In various embodiments, the auto-inject pen contains about 0.1 mL to about 5.0 mL of the pharmaceutical composition. In specific embodiments, the auto-inject pen contains about 0.5 mL of the pharmaceutical composition. In particular embodiments, the auto-inject pen contains about 1.0 mL of the pharmaceutical composition. In other embodiments, the auto-inject pen contains about 5.0 mL of the pharmaceutical composition.

6.4.2. Lyophilized DNA Formulations

In some embodiments, DNA constructs of the present inventions are formulated as a lyophilized composition. In specific embodiments, DNA constructs are lyophilized as disclosed in U.S. Pat. No. 8,389,492, incorporated by reference in its entirety herein.

In some embodiments, DNA constructs are formulated with certain excipients, e.g., a carbohydrate and a salt, prior to lyophilization. Stability of the DNA construct to be utilized as a diagnostic or therapeutic agent can be increased by formulating the DNA construct prior to lyophilization with an aqueous solution comprising a stabilizing amount of carbohydrate.

The carbohydrate can be a mono-, oligo-, or polysaccharide, such as sucrose, glucose, lactose, trehalose, arabinose, pentose, ribose, xylose, galactose, hexose, idose, mannose, talose, heptose, fructose, gluconic acid, sorbitol, mannitol, methyl a-glucopyranoside, maltose, isoascorbic acid, ascorbic acid, lactone, sorbose, glucaric acid, erythrose, threose, allose, altrose, gulose, erythrulose, ribulose, xylulose, psicose, tagatose, glucuronic acid, galacturonic acid, mannuronic acid, glucosamine, galactosamine, neuraminic acid, arabinans, fructans, fucans, galactans, galacturonans, glucans, mannans, xylans, levan, fucoidan, carrageenan, galactocarolose, pectins, pectic acids, amylose, pullulan, glycogen, amylopectin, cellulose, dextran, cyclodextrin, pustulan, chitin, agarose, keratin, chondroitin, dermatan, hyaluronic acid, alginic acid, xantham gum, or starch.

In one series of embodiments, the carbohydrate is mannitol or sucrose.

The carbohydrate solution prior to lyophilization can correspond to carbohydrate in water alone, or a buffer can be included. Examples of such buffers include PBS, HEPES, TRIS or TRIS/EDTA. Typically the carbohydrate solution is combined with the DNA construct to a final concentration of about 0.05% to about 30% sucrose, typically 0.1% to about 15% sucrose, such as 0.2% to about 5%, 10% or 15% sucrose, preferably between about 0.5% to 10% sucrose, 1% to 5% sucrose, 1% to 3% sucrose, and most preferably about 1.1% sucrose.

DNA formulation of the invention can also include a salt, e.g., NaCl or KCl. In some embodiments, the salt is NaCl. In some embodiments, the salt of the DNA formulation is in an amount selected from the group consisting of between about 0.001% to about 10%, between about 0.1% and 5%, between about 0.1% and 4%, between about 0.5% and 2%, between about 0.8% and 1.5%, between about 0.8% and 1.2% w/v. In certain embodiments, the salt of the DNA formulation is in an amount of about 0.9% w/v.

The final concentration of the DNA construct in liquid compositions reconstituted from lyophilized formulations can be from about 1 ng/mL to about 30 mg/mL. For example, the final concentration can be about 1 ng/mL, about 5 ng/mL, about 10 ng/mL, about 50 ng/mL, about 100 ng/mL, about 200 ng/mL, about 500 ng/mL, about 1 μg/mL, about 5 μg/mL, about 10 μg/mL, about 50 μg/mL, about 100 μg/mL, about 200 μg/mL, about 400 μg/mL, about 500 μg/mL, about 600 μg/mL, about 800 μg/mL, about 1 mg/mL, about 2 mg/mL, about 2.5 mg/mL, about 3 mg/mL, about 3.5 mg/mL, about 4 mg/mL, about 4.5 mg/mL, about 5 mg/mL, about 5.5 mg/mL, about 6 mg/mL, about 7 mg/mL, about 8 mg/mL, about 9 mg/mL, about 10 mg/mL, about 20 mg/mL, or about 30 mg mg/mL. In certain embodiments of the invention, the final concentration of the DNA construct is from about 100 μg/mL to about 2.5 mg/mL. In particular embodiments of the invention, the final concentration of the DNA construct is from about 0.5 mg/mL to 1 mg/mL.

The DNA formulation of the invention is lyophilized under standard conditions known in the art. A method for lyophilization of the DNA formulation of the invention may comprise (a) loading a container (e.g., a vial), with a DNA formulation (e.g., a DNA formulation comprising a plasmid DNA), a salt and a carbohydrate, where the plasmid DNA comprises an IGF-1 gene, or variant thereof, into a lyophilizer, wherein the lyophilizer has a starting temperature of about 5° C. to about −50° C.; (b) cooling the DNA formulation to subzero temperatures (e.g., −10° C. to −50° C.); and (c) substantially drying the DNA formulation. The conditions for lyophilization, e.g., temperature and duration, of the DNA formulation of the invention can be adjusted by a person of ordinary skill in the art taking into consideration factors that affect lyophilization parameters, e.g., the type of lyophilization machine used, the amount of DNA used, and the size of the container used.

The container holding the lyophilized DNA formulation may then be sealed and stored for an extended period of time at various temperatures (e.g., room temperature to about −180° C., preferably about 2-8° C. to about −80° C., more preferably about −20° C. to about −80° C., and most preferably about −20° C.). In certain aspects, the lyophilized DNA formulations are preferably stable within a range of from about 2-8° C. to about −80° C. for a period of at least 6 months without losing significant activity. Stable storage plasmid DNA formulation can also correspond to storage of plasmid DNA in a stable form for long periods of time before use as such for research or plasmid-based therapy. Storage time may be as long as several months, 1 year, 5 years, 10 years, 15 years, or up to 20 years. Preferably the preparation is stable for a period of at least about 3 years.

6.5. Methods of treating neuropathy

In another aspect, methods are presented for treating neuropathy by administering the DNA construct encoding a human IGF-1 isoform.

6.5.1. Administration of a DNA construct encoding an IGF-1 isoform

The methods comprise administering a therapeutically effective amount of a DNA construct that expresses a human IGF-1 isoform to a subject. The subject can be a human or an animal with neuropathy.

In some embodiments, the method comprises administration of a DNA construct encoding a single human IGF-1 isoform. In some embodiments, the method comprises administration of a first DNA construct encoding a first human IGF-1 isoform or administration of a second DNA construct encoding a second human IGF-1 isoform. In some embodiments, the method comprises administration of a first DNA construct encoding a first human IGF-1 isoform and administration of a second DNA construct encoding a second human IGF-1 isoform. In some embodiments, the first IGF-1 isoform is Class I, Ec (Isoform #1) and the second IGF-1 isoform is Class I, Ea (Isoform #4). In some embodiments, the first IGF-1 isoform is Class I, Ea (Isoform #4) and the second IGF-1 isoform is Class I, Ec (Isoform #1). The first and second DNA construct can be administrated together or sequentially.

In some embodiments, the method comprises administration of a DNA construct encoding more than one human IGF-1 isoforms, dual expression constructs. In some embodiments, the DNA construct can express both Class I, Ec (Isoform #1) and Class I, Ea isoforms (Isoform #4). In some embodiments, the DNA construct further expresses Class I, Eb or Class II, Ea. In some embodiments, the DNA construct cannot express Class I, Eb or Class II, Ea. In some embodiments, the DNA construct can express Class I, Ec (Isoform #1) and Class I, Ea isoforms (Isoform #4), but cannot express any other IGF-1 isoforms.

In some embodiments, the method comprises administration of a DNA construct encoding human IGF-1, comprising: a first polynucleotide that has the same sequence as exons 1, 3 and 4 of the human IGF-1 gene (SEQ ID NO: 1) or a degenerate thereof; a second polynucleotide that has the same sequence as intron 4 of the human IGF-1 gene (SEQ ID NO: 2) or a fragment thereof; a third polynucleotide that has the same sequence as exons 5 and 6-1 of the human IGF-1 gene (SEQ ID NO: 3) or a degenerate thereof; a fourth polynucleotide that has the same sequence as intron 5 of the human IGF-1 gene (SEQ ID NO: 4) or a fragment thereof; and a fifth polynucleotide that has the same sequence as exon 6-2 of the human IGF-1 gene (SEQ ID NO: 5) or a degenerate thereof, wherein the first polynucleotide, the second polynucleotide, the third polynucleotide, the fourth polynucleotide and the fifth polynucleotide are linked in sequential 5' to 3' order.

In some embodiments, the method comprises administration of pCK-IGF-1X6 or pCK-IGF-1X10. In some embodiments, the method comprises administration of pTx-IGF-1X6 or pTx-IGF-1X10.

In some embodiments, the method comprises administration of more than one of the DNA constructs provided herein.

6.5.1.1. Delivery Methods

Various delivery methods can be used to administer the DNA construct expressing one or more isoforms of IGF-1.

6.5.1.1.1. Injection

In some embodiments, the DNA construct is administered by injection of a liquid pharmaceutical composition.

In currently preferred embodiments, the DNA construct is administered by intramuscular injection. Typically, the DNA construct is administered by intramuscular injection close to the site of nerve damage, site of pain or patient-perceived site of pain, or site of other symptom of the neuropathic disease. In some embodiments, the DNA constructs are administered to the muscles of hands, feet, legs, or arms of the subject.

In some embodiments, the construct is injected subcutaneously or intradermally.

In some embodiments, the DNA construct is administered by intravascular delivery. In certain embodiments, the construct is injected by retrograde intravenous injection.

6.5.1.1.2. Electroporation

Transformation efficiency of plasmid DNA into cells in vivo can in some instances be improved by performing injection followed by electroporation. Thus, in some embodiments, the DNA construct is administered by injection followed by electroporation. In particular embodiments, electroporation is administered using the TriGrid™ Delivery System (Ichor Medical Systems, Inc., San Diego, USA).

6.5.1.1.3. Sonoporation

In some embodiments, sonoporation is used to enhance transformation efficiency of the DNA construct of the present invention. Sonoporation utilizes ultrasound wave to temporarily permeabilize the cell membrane to allow cellular uptake of DNA. DNA constructs can be incorporated within microbubbles and administered into systemic circulation, followed by external application of ultrasound. The ultrasound induces cavitation of the microbubble within the target tissue to result in release and transfection of the constructs.

6.5.1.1.4. Magnetofection

In some embodiments, magnetofection is used to enhance transformation efficiency of a DNA construct of the present invention. The construct is administered after being coupled to a magnetic nanoparticle. Application of high gradient external magnets cause the complex to be captured and held at the target. The DNA construct can be released by enzymatic cleavage of cross linking molecule, charge interaction or degradation of the matrix.

6.5.1.1.5. Liposome

In some embodiments, DNA constructs of the present invention can be delivered by liposomes. Liposomes are formed spontaneously when phospholipids are suspended in an excess of aqueous medium. Liposome-mediated DNA delivery has been successful as described in Dos Santos Rodrigues et al., *Int. J. Pharm.* 566:717-730 (2019); Rasoulianboroujeni et al.,*Mater Sci Eng C Mater Biol Appl.* 75:191-197 (2017); Xiong et al., *Pharmazie* 66(3):158-164 (2011); Nicolau and Sene, *Biochim. Biophys. Acta,* 721:185-190(1982) and Nicolau et al., *Methods Enzymol.,* 149:157-176 (1987). Example of commercially accessible reagents for transfecting animal cells using liposomes includes Lipofectamine (Gibco BRL). Liposomes entrapping DNA constructs of the invention interact with cells by mechanism such as endocytosis, adsorption and fusion and then transfer the sequences into cells.

6.5.1.1.6. Transfection

When a viral vector is used to deliver a DNA construct encoding IGF-1, the construct may be delivered into cells by various viral infection methods known in the art. Infection of host cells using viral vectors are described in the above-mentioned cited documents.

Preferably, the pharmaceutical composition of this invention may be administered parenterally. For non-oral administration, intravenous injection, intraperitoneal injection, intramuscular injection, subcutaneous injection, or local injection may be employed. For example, the pharmaceutical composition may be injected by retrograde intravenous injection.

Preferably, the pharmaceutical composition of the present invention may be administered into the muscle. In some embodiments, the administration is targeted to the muscle affected by neuropathy (e.g., neuropathic pain or other symptoms).

6.5.1.2. Dose

The DNA construct can be administered in a therapeutically effective dose. In the methods described herein, the therapeutically effective dose is a dose effective to treat neuropathy in the subject.

In some embodiments of the methods described herein, the DNA construct is administered at a total dose of 1 µg to 200 mg, 1 mg to 200 mg, 1 mg to 100 mg, 1 mg to 50 mg, 1 mg to 20 mg, 5 mg to 10 mg, 16 mg, 8 mg, or 4 mg.

In typical embodiments, the total dose is divided into a plurality of individual injection doses. In some embodiments, the total dose is divided into a plurality of equal injection doses. In some embodiments, the total dose is divided into unequal injection doses.

In various divided dose embodiments, the total dose is administered to 4, 8, 16, 24, 32 or 64 different injection sites.

In some embodiments, the dose per injection is between 0.1 and 20 mg, between 1 and 10 mg, between 2 and 8 mg, or between 3 and 8 mg. In certain embodiments, the dose per injection is 0.1 mg, 0.15 mg, 0.2 mg, 0.25 mg, 0.3 mg, 0.35 mg, 0.4 mg, 0.45 mg, 0.5 mg, 1 mg, 2 mg, 4 mg, 8 mg, 16 mg, or 32 mg.

The total dose can be administered during one visit or over two or more visits.

In typical divided dose embodiments, all of the plurality of injection doses are administered within 1 hour of one another. In some embodiments, all of the plurality of injection doses are administered within 1.5, 2, 2.5 or 3 hours of one another.

In various embodiments of the methods, a total dose of DNA construct, whether administered as a single unitary dose or divided into plurality of injection doses, is administered only once to the subject.

In some embodiments, administration of a total dose of DNA construct into a plurality of injection sites over one, two, three or four visits can comprise a single cycle. In particular, administration of 64 mg, 32 mg, 16 mg, 8 mg, or 4 mg of DNA construct into a plurality of injection sites over two visits can comprise a single cycle. The two visits can be 3, 5, 7, 14, 21 or 28 days apart.

In some embodiments, the cycle can be repeated. The cycle can be repeated twice, three times, four times, five times, six times, or more.

In some embodiments, the cycle can be repeated 1, 2, 3, 4, 5, 6, 7, 8, 9, 10, 11, 12, or more months after the previous cycle.

In some embodiments, the total dose administered in the subsequent cycle is same as the total dose administered in the prior cycle. In some embodiments, the total dose administered in the subsequent cycle is different from the total dose administered in the prior cycle.

In currently preferred embodiments, the DNA construct is administered at a dose of 8 mg per affected limb, equally divided into a plurality of intramuscular injections and plurality of visits, wherein each of the plurality of injections in any single visit is performed at a separate injection site. In certain embodiments, the DNA construct is administered at a dose of 8 mg per affected limb, equally divided into a first dose of 4 mg per limb on day 0 and a second dose of 4 mg per limb on day 14, wherein each of the first and second dose is equally divided into a plurality of injection doses. In some embodiments, the administration of the DNA construct at a dose of 8 mg per affect limb constitutes one cycle. The cycle can be repeated once, twice, three times or more.

The actual amount administered, and rate and time-course of administration, will depend on the nature and severity of neuropathy being treated. In typical embodiments, the DNA construct is administered in an amount effective to reduce symptoms of neuropathy, for example, neuropathic pain. In some embodiments, the amount is effective to reduce the symptom of neuropathy within 1 week of administration. In some embodiments, the amount is effective to reduce the symptom of neuropathy within 2 weeks, 3 weeks, or 4 weeks of administration.

In some embodiments, two different types of constructs are administered together to induce expression of two isoforms of IGF-1, e.g., a first construct encoding Class I, Ec isoform and a second construct encoding Class I, Ea isoform. In some embodiments, a dual expression construct that encodes both Class I, Ec isoform and Class I, Ea isoform is delivered to induce expression of both isoforms.

According to the conventional techniques known to those skilled in the art, the pharmaceutical composition may be formulated with pharmaceutically acceptable carrier and/or vehicle as described above, finally providing several forms a unit dose form and a multi-dose form. Non-limiting examples of the formulations include, but not limited to, a solution, a suspension or an emulsion in oil or aqueous medium, an extract, an elixir, a powder, a granule, a tablet and a capsule, and may further comprise a dispersion agent or a stabilizer.

6.5.1.3. Variations

In vivo and/or in vitro assays may optionally be employed to help identify optimal dosage ranges. The precise dose to be employed in the formulation will also depend on the route of administration, and the seriousness of the condition, and should be decided according to the judgment of the practitioner and each subject's circumstances. Effective doses may be extrapolated from dose-response curves derived from in vitro or animal model test systems.

The DNA construct can be administered alone or in combination with other treatments, either simultaneously or sequentially.

6.5.2. Patients with Neuropathy

In the methods described herein, the patients selected for treatment have neuropathy. The patients can have peripheral neuropathy, cranial neuropathy, autonomic neuropathy or focal neuropathy. The neuropathy can be caused by diseases, injuries, infections or vitamin deficiency states. For example, the neuropathy can be caused by diabetes, vitamin deficiencies, autoimmune diseases, genetic or inherited disorders, amyloidosis, uremia, toxins or poisons, trauma or injury, tumors, or can be idiopathic. In some embodiments, the patients have diabetic peripheral neuropathy.

The patients can have one or more symptoms associated with neuropathy, such as pain (neuropathic pain), other sensory defects (e.g., loss of feeling, numbness, tingling, etc.), motor defects (e.g., weakness, loss of reflexes, loss of muscle mass, cramping, loss of dexterity, etc.), and autonomic dysfunction (e.g., nausea, vomiting, impotence, dizziness, constipation, diarrhea, etc.).

The patients can be treated by one or more treatment methods known in the art in addition to the treatment method provided herein.

Treatment methods of the present invention can be used to treat a human patient or an animal with neuropathy.

6.6. EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations can be used, e.g., bp, base pair(s); kb, kilobase(s); pl, picoliter(s); s or sec, second(s); min, minute(s); h or hr, hour(s); aa, amino acid(s); nt, nucleotide(s); and the like.

The practice of the present invention will employ, unless otherwise indicated, conventional methods of protein chemistry, biochemistry, recombinant DNA techniques and pharmacology, within the skill of the art.

6.6.1. Example 1

DNA Constructs Encoding an IGF-1 Isoform Reduce Mechanical Allodynia in a Murine CCI Neuropathy Model DNA constructs encoding individual human IGF-1 isoforms were constructed in the expression plasmid pCK using standard molecular cloning techniques.

Specifically, four polynucleotides (SEQ ID NOS: 15, 17, 19 and 21) were obtained by customized DNA synthesis process provides by Bioneer (Korea). These polynucleotides were synthesized with 5' linker, Cla I and 3' linker, Sal I. pCK vector and the polynucleotides were restricted with Cla I and Sal I. Plasmid #1 encoding Class I, Ec (Isoform #1) was generated by inserting a polynucleotide of SEQ ID NO: 17, which is a coding sequence of Class I, Ec isoform and comprises at least a part of exons 1, 3/4, 5 and 6 of IGF-1 gene, into the cloning site in pCK vector. Plasmid #2 encoding Class II, Ea (Isoform #2) was generated by inserting a polynucleotide of SEQ ID NO: 19, which is a coding sequence of Class II, Ea isoform and comprises at least a part of exons 2, 3/4 and 6 of IGF-1 gene, into the cloning site in pCK vector. Plasmid #3 encoding Class I, Eb (Isoform #3) was generated by inserting a polynucleotide of SEQ ID NO: 21, which is a coding sequence of Class I, Eb isoform and comprises at least a part of exons 1, 3/4 and 5 of IGF-1 gene, into the cloning site in pCK vector. Plasmid #4 encoding Class I, Ea (Isoform #4) was generated by inserting a polynucleotide of SEQ ID NO:15 and comprises at least a part of exons 1, 3/4 and 6, into the cloning site in pCK vector.

Expression of each IGF-1 isoform from each plasmid was tested and confirmed both in vitro and in vivo.

Therapeutic effects of the DNA constructs were then tested in the CCI mice, which is a widely accepted model for studying neuropathy. The CCI mouse model generated by the chronic constriction injury (CCI) of the sciatic nerve which is known to initiate several processes that result in chronic nerve injury in the periphery. The CCI mice are also known to have neuropathic pain. CCI surgery was performed on adult male ICR mice (with 24-26 g of body weight), following surgical and experimental procedures approved by the Institutional Animal Care and Use committee at Seoul National University.

Specifically, blunt dissections about 1 cm long were made under anesthesia to expose the right sciatic nerve, which usually lies between the gluteus and biceps femoris muscles.

Once the sciatic nerve proximal to the trifurcation site was exposed, it was given loose ligatures three times with 0.5 mm spacing using 6-0 silk (Ethicon) sutures. The ligatures were slightly tightened until there was a noticeable twitch of the right hind limb. Sham-operated mice were given the same dissections in the right thigh, but did not receive ligatures in the sciatic nerve.

Figure 2A:
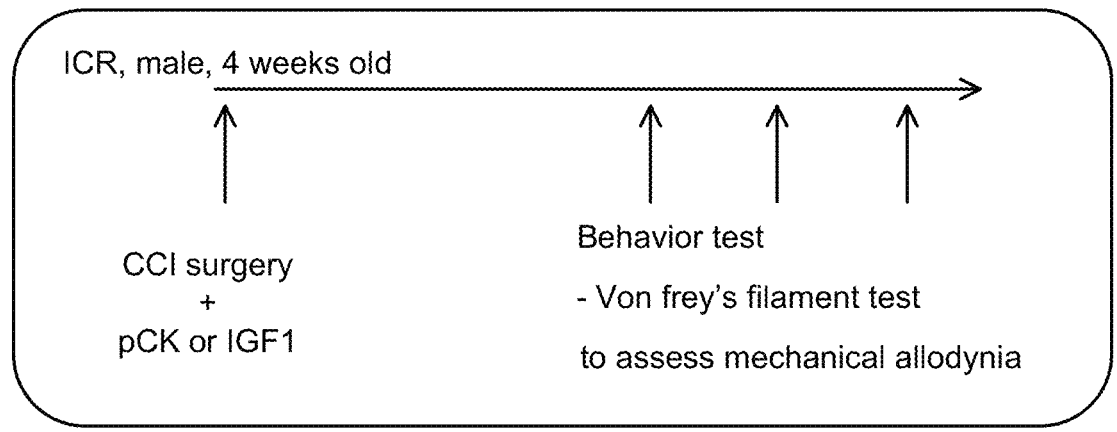

As schematized in FIG. 2A, a total of 200 μg of plasmid DNA was intramuscularly injected on the day of CCI surgery. The injected plasmid DNA was either 200 μg pCK (vector without insert; "pCK") or 200 μg of pCK-IGF-1—(i) 200 μg of plasmid #1 ("IGF-1 #1" encoding Class I, Ec IGF-1); (ii) 200 μg of plasmid #4 ("IGF-1 #4" encoding Class I, Ea IGF-1) or (iii) 100 μg of plasmid #1 ("IGF-1 #1" encoding Class I, Ec IGF-1) and 100 μg of plasmid #4 ("IGF-1 #4" encoding Class I, Ea IGF-1).

One week after CCI surgery, the development of mechanical allodynia was assessed using a Von Frey's filament test. Briefly, animals were placed individually in a cylinder on top of a metal mesh floor for adaptation. The mechanical sensitivity of mice was assessed by stimulating the hind paw using constant thickness of the filament (0.16 g). The test was repeated weekly thereafter.

Figure 2B:
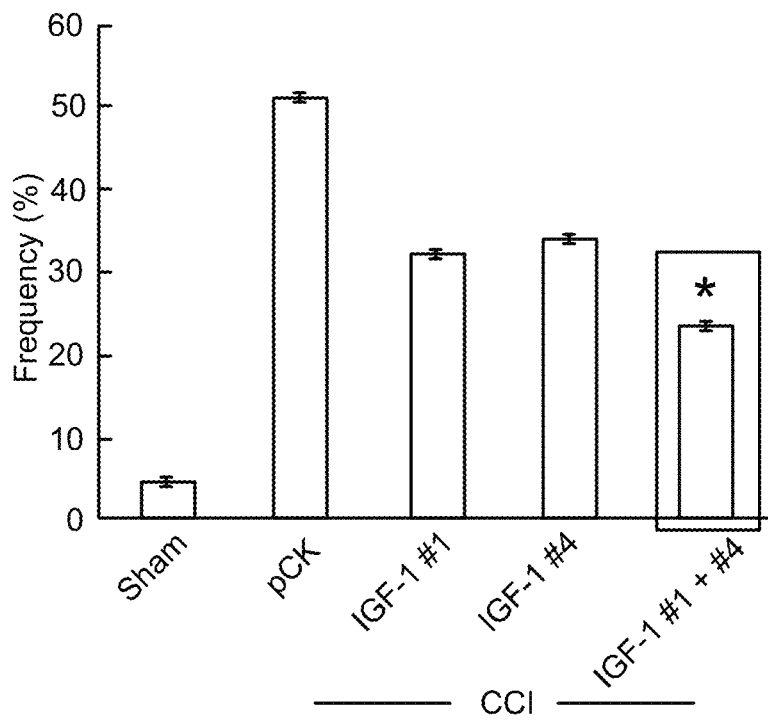

FIG. 2B is a histogram summarizing the frequency (%) of paw withdrawal measured in the CCI experiment described in FIG. 2A. The result demonstrates (i) that injection of IGF-1 #1, expressing IGF-1 Class I Ec provided measurable reduction in paw withdrawal frequency as compared to vector alone (pCK); (ii) that injection of a IGF-1 #4, expressing IGF-1 Class I Ea, also provided measurable reduction in paw withdrawal frequency; and (iii) that injection of DNA constructs expressing IGF-1 Class I Ec (IGF-1 #1) and Class I Ea (IGF-1 #4) together provided greater, statistically significant, decreases in frequency of paw withdrawal frequency as compared to vector alone (pCK).

All values are presented as mean±standard error mean (SEM) from three independent experiments. Differences between values were determined by one-way ANOVA followed by Tukey's post-hoc test or Bonferroni's multiple comparison test.

6.6.2. Example 2

DNA Constructs Capable of Expressing Both IGF-1 Class I Ec and Class I Ea Isoforms Since a DNA construct expressing IGF-1 Class I Ec (IGF-1 #1) and another DNA construct expressing Class I Ea (IGF-1 #4) together had greater, statistically more significant, effects on mechanical allodynia in the behavioral experiments described above, we constructed several plasmids designed to simultaneously express both the IGF-1 Class I Ec (IGF-1 #1) and Class I Ea (IGF-1 #4) through alternative splicing of the RNA transcript. In particular, DNA constructs were generated to comprise sequences for exons 1, 3/4, 5 and 6 and introns of IGF-1 gene or their fragments. Several DNA constructs including different variations were generated and tested for their capability to express both IGF-1 Class I Ec isoform and Class I Ea isoform.

Each plasmid was constructed using pCK as the plasmid backbone to contain an insert operably linked to the pCK expression control sequences. The insert was created by concatenating (1) a first polynucleotide encoding human IGF-1 exons 1, 3, and 4 (SEQ ID NO:1); (2) a second polynucleotide, either the IGF-1 intron 4 (SEQ ID NO: 2) or a fragment thereof; (3) a third polynucleotide encoding exons 5 and 6-1 (SEQ ID NO: 3); (4) a fourth polynucleotide, either intron 5 (SEQ ID NO: 4) or a fragment thereof; and (5) a fifth polynucleotide encoding exon 6-2 (of SEQ ID NO: 5), in which the first polynucleotide, the second polynucleotide, the third polynucleotide, the fourth polynucleotide and the fifth polynucleotide were linked in sequential 5' to 3' order. The plasmids differed in the size of the fragment of intron 4 and/or intron 5. Specifically, SEQ ID NO: 6 provides the nucleotide sequence of the intron 4 fragment used in vector pCK-IGF-1X6, and SEQ ID NO: 7 provides the nucleotide sequence of the intron 4 fragment used in vector pCK-IGF-1-X10. SEQ ID NO: 8 provides the nucleotide sequence of the intron 5 fragment used in vector pCK-IGF-1X6 and pCK-IGF-1X10.

Figure 3A:
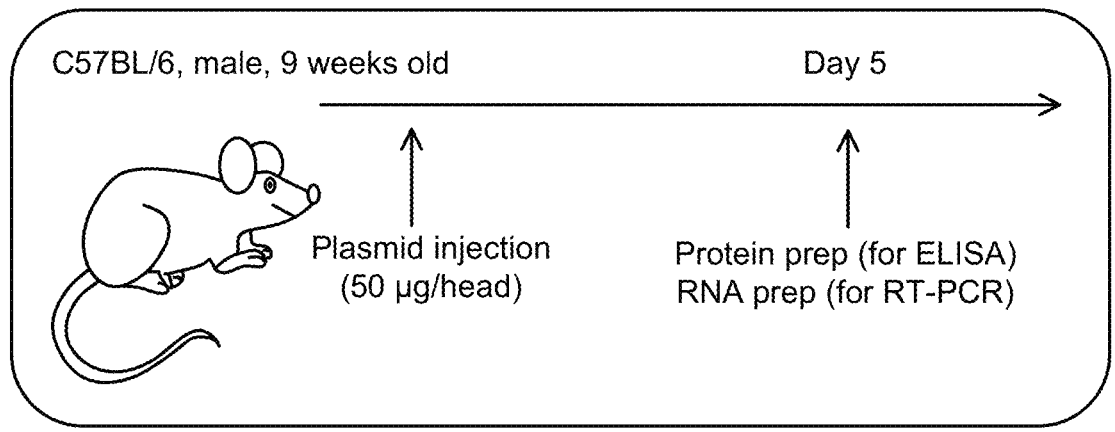
FIG. 3C shows the location of forward/left (L) and reverse/right (R) primers used in RT-PCR for discriminating expressions of IGF-1 isoforms #1 (Class I Ec isoform) and #4 (Class I Ea isoform).
FIG. 3D shows agarose gel electrophoresis of RT-PCR products, showing expression of isoforms #1 and #4 from dual expression constructs pCK-IGF-1X6 and pCK-IGF-1X10. Both pCK-IGF-1X6 and pCK-IGF-1X10 induced high-level expression of both isoforms.

To test expression of Isoform 1 (Class I, Ec) and Isoform 4 (Class I, Ea) from the various constructs in vivo, 9 week old male C57BL/6 male mice were injected with 50 μg plasmid in their T.A. (tibialis anterior) muscle. Their T.A. skeletal muscles were obtained 5 days after the injection. The skeletal muscles were then homogenized in a lysis buffer containing protease inhibitor, phosphatase inhibitor cocktail (Roche Diagnostic Ltd.), and PMSF (Sigma) using polypropylene pestles (Bel-Art Scienceware). The samples were centrifuged at 12,000 rpm for 15 minutes at 4° C., and the supernatants containing total protein were subjected to human IGF-1 ELISA (R&D Systems) as set forth in the manufacturer's protocol. The level of IGF-1 detected was normalized to the total amount of protein extracts from the tissue, as measured by BCA protein assay kit (Thermo, Ill., USA). The experimental procedure is summarized in FIG. 3A.

Figure 3B:
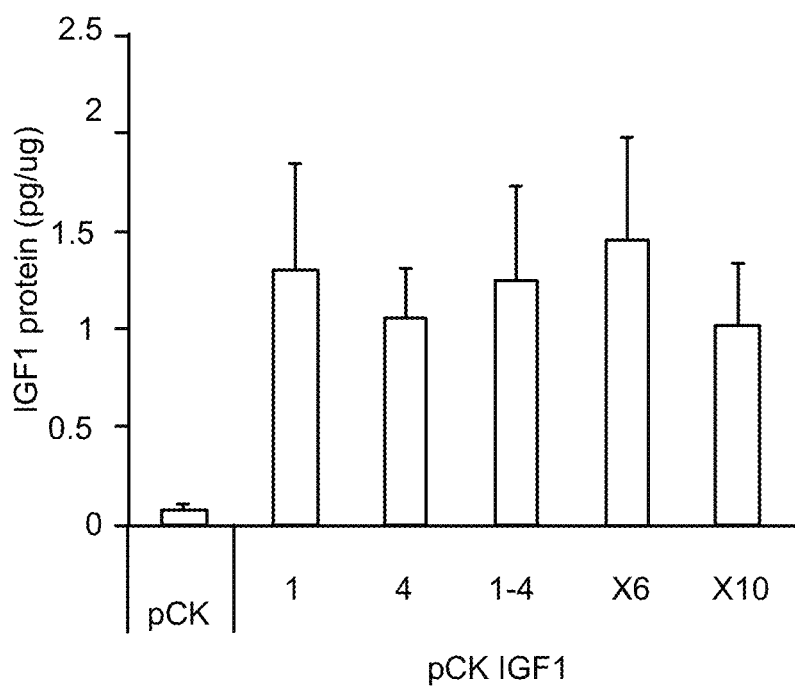

As shown in FIG. 3B, the total expression level of human IGF-1 protein in mouse T.A muscle was determined by ELISA. Regardless of whether the mouse received 50 μg of construct expressing a single isoform ("1" (Class I, Ec) or "4" (Class I, Ea)), 25 μg of a first construct expressing isoform #1 (Class I, Ec) plus 25 μg of a second construct expressing isoform #4 (Class I, Ea) ("1+4"), or 50 μg of either construct expressing both isoforms, pCK-IGF-1X6 ("X6") or pCK-IGF-1X10 ("X10"), the total expression levels of human IGF-1 protein were similar.

Figure 3C:
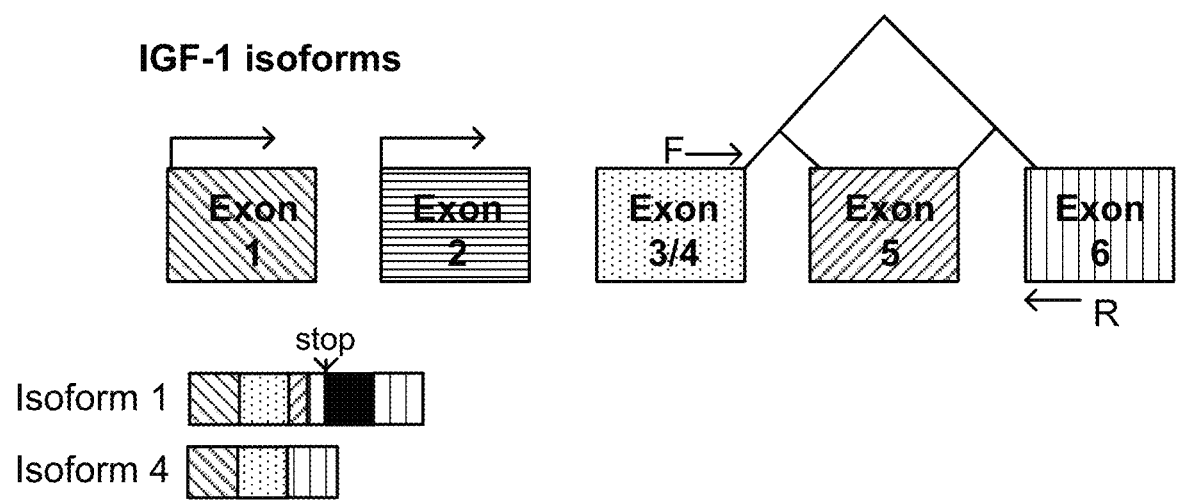

We used RT-PCR to determine whether the constructs expressed mature transcripts for both isoform #1 and isoform #4 simultaneously. RT-PCR reactions were performed with a forward/left primer (L) that binds to exon 3/4 and a reverse/right primer (R) that binds to exon 6. As further explained in FIG. 3C, the RT-PCR of a transcript for Isoform #1 (Class I, Ec) would generate two amplicons—178 bp amplicon and 259 bp amplicon, whereas the RT-PCR of a transcript for Isoform #4 (Class I, Ea) would generate a single amplicon of 129 bp.

For RT-PCR, skeletal muscles were collected, mechanically homogenized using polypropylene pestles (Bel-Art Scienceware), and extracted in RNAiso plus (Takara). Quantification of RNA was done by using a nanodrop instrument. Equal amounts of RNA were used to synthesize cDNA using Reverse Transcriptase XL (AMV) (Takara), and PCR was performed using the forward (TGA TCT AAG GAG GCT GGA (SEQ ID NO: 28)) and reverse (CTA CTT GCG TTC TTC AAA TG (SEQ ID NO: 29)) primers indicated in FIG. 3C.

Figure 3D:
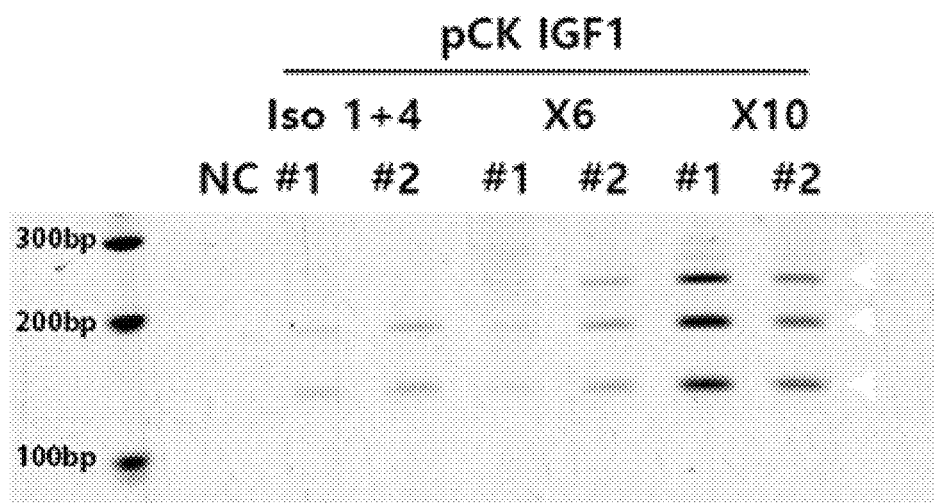

As illustrated in FIG. 3D, pCK-IGF-1X6 and pCK-IGF-1X10 expressed mature transcripts for both isoform #1 (178 bp and 259 bp bands) and isoform #4 (129 bp band). Expression of mature transcripts for both isoform #1 and isoform #4 were not detected from constructs other than the pCK-IGF-1X6 and pCK-IGF-1X10, which data are not provided herein.

In order to confirm that the two isoform transcripts were both effectively translated into protein, we transfected 293 T cells with pCK-IGF-1-X6 or pCK-IGF-1-X10, as illustrated in FIG. 4A. For immunoblotting, cells were prepared 2 days (48 hours) after the transfection of plasmid DNA, followed by lysis using RIPA buffer with protease and phosphatase inhibitor cocktail (Roche Diagnostic Ltd.). Equal amounts of protein were separated on 10% SDS-polyacrylamide gel, and transferred to a western membrane (PVDF). The membrane were blocked with 1% BSA (Invitrogen-Gibco) in TBST (20 mM Tris-HCl, pH 7.4, 0.9% NaCl, and 0.1% Tween20) for 1 hour and probed with primary antibodies diluted in blocking solution at 4° C. overnight. Primary antibodies used to examine the level of IGF-1 isoform 1 and isoform 4 were provided by Abclon (Korea), and those for IGF-1 and β-actin were purchased from Abcam (UK) and Sigma-Aldrich (US). After washing with TBST, membranes were incubated with HRP-conjugated goat anti-mouse or rabbit IgG secondary antibody (Sigma) at room temperature for 1 hour. The blots were then washed three times with TBST, and the protein bands were visualized with the enhanced chemiluminescence system (Millipore). β-actin was used as a loading control.

Western blotting data shown in FIG. 4B confirm that pCK-IGF-1X6 and pCK-IGF-1X10 plasmids express both isoforms of IGF-1 at the protein level.

6.6.3. Example 3

DNA Constructs that Simultaneously Express IGF-1 Class I Ec Isoform and Class I Ea Isoform Reduce Mechanical Allodynia in a Murine CCI Neuropathy Model Using the protocol described in Example 1 and schematized in FIG. 5A, we tested the ability of our DNA constructs to reduce mechanical allodynia in a mouse CCI model of neuropathy.

FIG. 5B is a histogram showing the frequency of paw withdrawal, demonstrating statistically significant reductions in mechanical allodynia after simultaneous intramuscular injection of constructs encoding IGF-1 isoform (IGF-1 #1, IGF-1 #4, IGF-1 #1+ #4, IGF-1X6, and IGF-1X10). In particular, the effects on mechanical allodynia was even better when the mice were administered constructs separately encoding IGF-1 isoforms #1 and #4, or injected with the dual expression construct pCK-IGF-1X10.

6.6.4. Example 4

DNA Constructs that Simultaneously Express IGF-1 Class I Ec Isoform and Class I Ea Isoform Induce Axon Growth in a Mouse Nerve Crush Model Therapeutic effects of the DNA constructs were further tested in a nerve crush model. The nerve crush model was generated with adult male C57BL/6 mice (with 24-26 g of body weight) following surgical and experimental procedures approved by the Institutional Animal Care and Use committee at Seoul National University. To induce sciatic nerve crush, the right sciatic nerve of each mice was exposed by an incision and the nerve was crushed with fine hemostatic forceps for 15 seconds. The incision was then sutured using 5-0 black silk suture. Total amounts of 200 µg plasmid DNA (200 µg of pCK, or 200 µg of pCK-IGF-1X10) were intramuscularly administered on the day of nerve crush to the muscles nearby the sciatic nerve.

Four weeks (28 days) after nerve crush and plasmid DNA injection, mice were fixed by perfusion with 2% paraformaldehyde +2% glutaraldehyde in 0.1M PBS. Right ipsilateral sciatic nerve was then prepared and further incubated with fixation solution for 4 hours. Fixed tissues were treated with 1% osmium tetroxide in 0.1 M PBS, followed by en bloc staining using 2% aqueous uranyl acetate overnight. The next day, tissues were then dehydrated by a serial passage in 30% to 100% ethanol for 10 minutes, and dehydrated tissues were then embedded in resin compound. After the embedding process, samples were polymerized with Spurr resin and incubated in dry oven. Samples were then sectioned and visualized using transmission electron microscopy (TEM).

TEM images of the samples from a Sham animal, pCK-treated animal, and pCK-IGF-1X10 treated animal are provided in FIG. 6A. The images clearly demonstrate that nerve crush animals have significant nerve damages compared to Sham animals, with significantly smaller axon diameters. The reduction in axon diameters was inhibited by administration of pCK-IGF-1X10, but not by administration of pCK.

pCK-IGF-1X10's effects on axon growth were quantified by measuring neuron diameters. Distributions of neuron diameters in the nerve crush animal treated with pCK ("Crush-pCK") and a nerve crush animal treated with pCK-IGF-1X10 ("Crush-X10") are provided in the graph of FIG. 6B. The graph clarifies that the animal treated with pCK-IGF-1X10 had neurons having larger diameters. This again confirms that pCK-IGF-1X10 can treat nerve damages by inducing axon growth.

7. INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

8. EQUIVALENTS

While various specific embodiments have been illustrated and described, the above specification is not restrictive. It will be appreciated that various changes can be made without departing from the spirit and scope of the invention(s). Many variations will become apparent to those skilled in the art upon review of this specification.

Sequence Listing

| SEQ ID NO | Description | Sequence |
|---|---|---|
| SEQ ID NO. 1 | IGF-1 (exon 1, 3, and 4) | ATGGGAAAAATCAGCAGTCTTCCAACCCAATTATTTAAGTGCTGCT<br>TTTGTGATTTCTTGAAGGTGAAGATGCACACCATGTCCTCCTCGCA<br>TCTCTTCTACCTGGCGCTGTGCCTGCTCACCTTCACCAGCTCTGCCA<br>CGGCTGGACCGGAGACGCTCTGCGGGGCTGAGCTGGTGGATGCTC<br>TTCAGTTCGTGTGTGGAGACAGGGGCTTTTATTTCAACAAGCCCAC<br>AGGGTATGGCTCCAGCAGTCGGAGGGCGCCTCAGACAGGCATCGT<br>GGATGAGTGCTGCTTCCGGAGCTGTGATCTAAGGAGGCTGGAGAT<br>GTATTGCGCACCCCTCAAGCCTGCCAAGTCAGCTCGCTCTGTCCGT<br>GCCCAGCGCCACACCGACATGCCCAAGACCCAGAAG |
| SEQ ID NO. 2 | IGF-1 (intron 4) | GTAAGCCCACCTGGGTGGGATCCAGCCATCCTCAAGTGGTCTCTCT<br>CTTGTGCATGTGGGTGGGCCAAGCAGAAATCCTGCCCCATAGTCTC<br>CTGGCTTACAAGTCAGAAAAAGCTCCTTTGCACCAAAGGGATGGAT<br>TACATCCCCATCTCTTTGGTCACTCTGCATTGCAAATTTCCCCTCCC<br>ACCGCTATGGACGATGTGATGATTGGAAGATGTTACAAAACAGTG<br>GCTAAACAAACATGGGCTTTGGTGTCAGACAAAAGTGAAGTCCTG<br>GCTTTCTCACACACCAGCTTAGAGCCCTTGGCAAATAATGTGATGT<br>ACCCAAGCCTCAGTTTCATCAGTAACATTGGGATAATAATAATATC<br>TACCACATCAGTTTGTTGTCAAAATTAAGTAGCTCATGCATATACT<br>TTGAGATGCTTTTCACATGCCTGCATAAAGTAATTGTTGGACCATC<br>GTTAATGTCTGCCATAATTGCACTTAATAACAAAGCTTGTAACCTT<br>TCAAGTTCTGAGATTCTACAATCTTCCAAAGAAAATAAAAGGCTA<br>ATGGGAACTATTCAAAATTCATATTCAGTAGCAAGCATAATTAAA<br>CATGAAACATTAAAAATAGAAATTTCTGTTTGGCTATAAGAATGC<br>CTAGACATTTGTAATGATCAAAATCTGCAGGCATCATTTTCTAAGA<br>GCTAGACTGTAAACAAACCTCAGAGGTACCAACTATGCCATCAGT<br>AGTACATAAAACATCTGATGCACATTTAGTCACTTGATCGATTTCT<br>CTTGAATGAGTGAACGAATGAACAAATGAATATAAGAGATTAAAA<br>TTTTAGCCATTAAGTAGAAAGAATAAGAACTAAAGAGAAGGTAAA<br>GGAGGAAAAAGAGAAGGCAAGGAAGTTGAGTAAGGGAAGAAATA<br>GCTCTCGTTTAAGTATTTTGGGGACTCTGTTGAAAAAAGAAATGCC<br>AACATGTGGTTTTAATCTTTGGAGCTAGAACTAATAATATTGTGCA<br>AAAGCACAAGATGAGAGATCAAGAAGTTCACCATGACACCTTCGC<br>TGCTTCCTGGTCTTAAACCTCAGCTGAGGCTGGAAGAGGACCATG<br>GTGGCTTATTGGAGATGTGACCCCAGGGAGCCCCTCTGAAGGATG<br>GAAGGGGACTGGGCAAGACCCAACACACACAGAACACAGTAGCC<br>ACTGGCCAGGCAGGAAGCAAGGATCTCAGAAAAGACTTTTAGGTG<br>AATGTGGCAGGAAAAGCGTGCTTGCTGGGGCAAAGGCAGATTCATT<br>CTTTCTCTTCCCAGGTGACCCAGCGCCTCTTGGTTTCTAACTGGGG<br>AGGGGGTAGGTGTCAAGAGATGAGTCCCAAAGTTCTGGAATGGTG<br>GGTCTTGTGACTGAGGTCTAGACCCCTCTCCAGCATGAGTGCTGTC<br>TCCTGCATCATATGGAGCCTGGGCATTCTGAGCTCATTCAAAGGGA<br>CACCATGGGAACCACTTGTTCTCAATGCAATTATTTTTGTGATGTT<br>TACAG |
| SEQ ID NO. 3 | IGF-1 (exon 5 and 6-1) | TATCAGCCCCCATCTACCAACAAGAACACGAAGTCTCAGAGAAGG<br>AAAGGAAGTACATTTGAAGAACGCAAGTAG |
| SEQ ID NO. 4 | IGF-1 (intron 5) | AGGACAGGAGGATTAAACAGACAGAGGCAAGGATGATGAGAGAG<br>GAGCAGACAGCAAGAATGAAAAGCAGAAAATACAATAGAGGAAA<br>TGAAGAAAAGTAGGCCTGCTGGAGCTAGATGATGATGTGATGGAA<br>ATAGAAGTAACCTTTTAGAGAATCTCGCTAAGAAACATGGAGAAA<br>ACGGAAAAGAAAAATGTAATGCCCTAGAAAGCGCAAAGAAAGAC<br>AGTGGCAAAAATGAAAAAAAAAAATAAAAATTATAAAAGAGGCA<br>AAAAAAGACACACTATTCTCTGCCTCTAAAACACAATTAAATAAA<br>AGAATTTAAATAAAAATTAAGGCTTCTATATGCATTTTTAAATTTT<br>GTATGAATCTGTTATGGAAGAATTGCCTATGTCAATATATGTTCAG<br>AGTTAAATATTAGCCCCAAATGCTCAGCAAGACTGAATTGTGTCAT<br>AGAAGTTCCCAGATTCCCTTTTCCCGCAATGTCATTGGAGGCTGCA<br>TTTCTTAGTCAAGTCCAGGGTTTAGGCCAAAGGGCATCCGGTATTG<br>CCTAAAACCCTGTGAGGTCTGTGAGGTAACTTTTGAGAAGAGGTC<br>ACTGCACTCTTCATCTTTTTTGCACTTTGGAATCAGATATAAAAGA<br>TGTATAAGTTTGCTAGGGCTGCCATAACAAAGTATCATAGGCTAG<br>GTAGTTTAAACCACAGAAATTGATTTTTTCATAGTTCTGGGAGTTG<br>AAAGTCCAAATCAAAGTATCAGCCCTTGCAAGGGCCTTAGAGAA<br>GGCTCTGTCATGGGCTCCTCCCCTCGGCTTGTAGGTGGCCTCCTTC<br>TTCTCCCCCTGTGTCTTCACTTCATCTTCCCTCCATACATATCTCTG<br>TGTCCTAAACATCCTCTGTGTGAAACAACACCAGCCAGGTTGGATTT<br>GGGCCCACCCCACTGACCTCATTTTAACTTAATTATCTCTGTAAAG<br>ACTCTGTCTCCAAATACAGTCATATTTTGACGTACTGGGAGTTAGG<br>GCTTCAACACATGAATTTGGACACAATTCAGCCAGTGACAGAAGA<br>CTTCTGATCTCTGATGATAACCACTGCATTTTGATTACAGCTCCTA<br>GAAAACACTCCCCTCCACCACCCCACCACAGATCTATTTTTATATC<br>TGAAACCCTGAGTTTCTGCTCCATGAGAACCCCAGGAACATACTAT<br>GTTAGATCTGGAAGAAGCCTCAGAAATCCCCTTATTTTGAAGACTA |

| SEQ ID NO | Description | Sequence |
|---|---|---|
| | | GGACACTGAGATCCAGAAGTGGGTAAAGATGTGCTTGGGTTCTAA |
| | | GCTGCTCTTCTTTTGGCCAGGAGACAACAGCACATAATCAAAGTG |
| | | GGTCAACTAAGAAAGAATTCCAGAAGGAAAAGAGAGGGCAGAAA |
| | | TGAAGGGAGAGAATGAGAGCAAAAGTGCTGGATTTCCCTGAGGGT |
| | | GAAGAAAAGTTAAATAGAATCACAGAATTCAGATTTTAGAGATCT |
| | | TCTCCTTCAGATCCCTTGGTTTAATCAGTAGGATTGGGGTCTTCAT |
| | | AGATAATAAAGCAAAAACTCTCGCCATCCTCCAAGTTGTGAATTA |
| | | GAAGAGCTGAGAAAGGGTACAAGACGGAAGTTCTCTACCAAACA |
| | | AATGGTGACATTTTGGGGTAAGAATATGACTAACCCAGAAGTGAA |
| | | GCATTTCATCCAAGTAGTCTATTTTGAAGATGTCATGGTATAAAGG |
| | | AACCTCCTTTCTGCCTGGTCCTCCATGCCTCTGCCATGCTTTTTACT |
| | | CCAGGATCACCCTTTCTAGTGGTTCACTGAAAACCCAGGATTACTT |
| | | AAATATGATGGACATGTTCACGGCTCAATCCAGGAGGAAAAGGTC |
| | | GAACTGAAAGCATGCCAAAGCCCCACATGGGAGCCAAGCCACTGC |
| | | TGCTGTGGTTGCAAAGTGGATCCTGGCTTATCAGAGCAGAGAGAA |
| | | GCCAGGCTCGTGCCTTAGCCCAAGTGGCCAGTCACCTTATTCAGGA |
| | | GATACTAAGTTCTCCAGCTAAGACATCCATGCTTTGGGACCAGCTG |
| | | CAGACAGAAGCCAATTCCTACTACAACCATCACCTTAGAGTAGCA |
| | | TATAGACACAGATGGCTCTTCAAAGGACCACAGTTCCATGGAATA |
| | | ACTAAGAATTCATGTCCTGTGGAAAGGTTTGAATAAACTATAATTA |
| | | TACCCAATCATAAATTTCATTCAAGAAGAACTAAAGCAAAGGCAA |
| | | AGACAGAGAGAAGAAGGAAGGAAGGAGGGAGGGAGGGAGGGAA |
| | | GGAAGGAAGGAAGGAAGGAAGGAAGGAAGGAAGGAAGGAAGGA |
| | | AGGAAGGAAAGGGAAGGAAGAACAAAAAGACTTTCTAGTTAAAG |
| | | AATGCTTAACTAGCAAACTATGTACTATAAGACAGTTCTTTTCGGA |
| | | ATGAGTTTTATCAACTCTAAAGCAATTATCTTGAATGCCTACATGT |
| | | GATTACTGAATAATATGAACCAAGAAAACAGAAAGAATCTATATT |
| | | ATCTTTCCATTTCCTTCTTTCCAGTATCAATACCCAAGCCTCTAGTG |
| | | ATACATGGCATATAATGTTGGATGGATGGATGGATGGATGGATGG |
| | | ATGGATGGATGGATGGATGGATGAATGGATGGTTGGATGGACAAA |
| | | TGAGTAACATAGGCTGATGAATAGTGGTAGAAAGACACACCATAA |
| | | AAACAAGTGGCACTTCTGAGATGAAATGATTCCTATTCTCCTACAC |
| | | AAGACAGTGAGGCAAGTACAGAGTAAAAAAGGAAAGGCATAGGA |
| | | GCTATGCTTATACAAGTATTGTATGTTTGGAATTTCCTTCGCTGGC |
| | | CAAATTGAAATTGTTCAAGGACCTATTGCTACAGGTGGCAACTGG |
| | | CTAAGAATTTCATAGTGAATATTATACACCTATTACTCCCCTTAAT |
| | | GTTTCTTTGAAGTAAGCAGAATATTAATAATCATTTAAAATTCCAG |
| | | TGTTTCAACTTCAATTGTTTCCTAGGGCAAATTGATAATTGTGTGT |
| | | AAAACTAATTGGAATATGTATGGAATAATCATCCTGAAATAAAAT |
| | | TGGTGAAAAGTATTTGTTATTGGGCATCTACAATGTGCAAACCTCT |
| | | GTACTAGGCATGAACAAGAGTTATAAGCATTGGAGAGGCTAAAAT |
| | | ATAGTCCTTAAGGCTGGGCACAGTGGCTCATGCCTGTAATCCTAGC |
| | | ACTTTGGGAGGCCAAGGCGGGCAGATTGCCTGAGCTCAGGAGTTC |
| | | AAGACCAGCCTGGGCAACATAGCGAAACCCCATCTCTACTAAAAA |
| | | TACAAAAAAATTACCTGGGCATGGTGGCACGCACCTGTAATCCCA |
| | | GCTACTCAGGAGGCTGAGGCATGAGAATTCCTTGAACCTGGGAGG |
| | | CAGAGGTTGCAGCGAGCCGAGATCCTGCCGCTGCATCCCAGCTTG |
| | | GGTGACAGAGTGAGACTCTGTCTCAAAAAAAAATTAAATAATAAA |
| | | TAAATAGTAAAATACAGTCATTAAGAGTACAAAATGTAGATTCAG |
| | | ACTACCTGGGTTCAAATCTTGGCTCTTACTTGCATTGTGGCTTTGG |
| | | GCAGATCATGTAACTTATGTGTGCCTCAGTTTCCTCATCTGTTAAA |
| | | TAGGGGCAACAACTGAATCTACCTTATTCAGTTGTTGTGAGGGTTT |
| | | ATTGAGATTGTGTGTGTATGTGTGTGAGTGTAGTGTGTGCATGT |
| | | GTGTGTCTGTGCAAGGAGTGGGAGGTGTATATTCAGAGACACATA |
| | | TTACAGCACTTAAAATGGTATCTAGCACTTAGTAAGCATTATTCAA |
| | | GTTTTAGTTAACATTATTTTACTTACCTCTGAAAATTGGAGCTATGT |
| | | GAAAAAGAAGTTGGTCTCCTGAAGTAGAAGCCAGTCTTGTGTCAC |
| | | CAAAAACTTCAAGCCCAAGCTTGCCAACGCTTTTCCATGATGTGGT |
| | | AGTAGAGTTTCAAGCATGTGGTAGGATAAGAGAACTCAATGACCT |
| | | AAGAACCATTCCAACCCAGAGAACCCTGTTCTATGAATAATTC |
| | | CAACTTAAATAGGTAGCTTGGCTCTCCAAGTGAGAGCCATTGCTT |
| | | CTGTTTCCGGGTCATATAATGAACTTTCAGAAAACCACCATTTTTC |
| | | TCAACCAGTTAAAATTAAGTGTAATACGTGCTTTCATTTCATGGTG |
| | | CCTGGGGAAAATTTAATTGTAGTATGAACTCCAGTTATTGGTAGTC |
| | | TTAAGTAAAATTGCCAAAATAAATAGAAATGCAGGATATTTCTGG |
| | | GCTCACACAGCTTCCGGGACACTTTAGTTTCTTGGGCTGCCAATCC |
| | | AGTGCCTTTCACAAGCATTTGATCTTTTTTCAAACATCTCTTGAAA |
| | | ACAAACAAAACCTCACACAGCTTCTAATGTGTGCACTGTTCGAAT |
| | | GTAAGGGTGGAAAAGGAGGCAAAGAAATGAGCTCCCAAAGAGCA |
| | | ATTCCCCTTCTCTCGCCTCCATCCCTTGACGACCTCCCTCCCACTAA |
| | | AGGGAAACATTGTTTCTTAGGTAATAAATTCTGCAATTTCTCAAG |
| | | TCCATTAACATCCACTGGGCAAGATGAGATCTATTCTTTTTATTTG |
| | | CCCATAGGAAAAGAATAGTGCTTTTTGCAATATTCACTAGATAAC |
| | | ACAGAGTTGACTTTTAATCCAAGGGCAACATTGATAGTCTCTAGTT |

Sequence Listing

| SEQ ID NO | Description | Sequence |
|---|---|---|
| | | AAAGGGGAAGCCTTCAGGAGCAATGAAAAGATTAATAGTTTTAGA |
| | | TGAAGCAGAATCCAAATCCCTTTTTATGAGTTTTGAAATATCCAGT |
| | | TTGTATGCTCACCTCAATACTTAAAGCCCAGTTACTGATTCCTTTG |
| | | GCCTAAGCAAGACAGGTCAATTTTTAAAGAGGGAGTAGCTGAGGT |
| | | TAGCAAAAATTCTCCAGGTCCACAAAACTTCCAGACCTGCAAGGT |
| | | GAAAATCAGCTTTTCTGTCATCCCTAAAGGCCTAACTGGAATCAGA |
| | | ACTTTTCCCTGATGCCCACATATTTGGAGGTCCTTTTTTAATGGGA |
| | | CTCCTTAATGCCTTTAGTGCCATCCCATTTTCATCCAGTGTCCAAA |
| | | AGAAATGATTTAAAAATATAAACGTATGTTTAAATTCCAGAAGAG |
| | | AGAAATGGAGATTGAGAACAATAGGGAAATGATGAGAGCTATGG |
| | | GAAAAGAGGTTTATGAGTCCATGTCTGATTCTTCCAGAGAGCCCCT |
| | | AAGAAAGTTCTTATCATACCAGGAACTCAATTATAACTTTCATTGC |
| | | CTATTGTTAGATGAGTAACAGGAGCTAGAAAACATTTTGGAAATT |
| | | CCCATCTTTATTTTTTTAACTAATATGATTATAGTTTTAAGAACCAT |
| | | TGGTCAAGAAGCTAACTTTTTAAAAAGTGGAAGTATGATGGTTAG |
| | | AAATAAGAATGCTAAAGGTGCATCAAGCTGATTTTAATTCTAAAT |
| | | GTCCTTGGCAGCAATTTAGAATCTGTAATAAACTACACCAAACAG |
| | | TTTTGAGGGGAAGGGGATTAGTTTCTCCCCTTCCTTCGTGTGTGTG |
| | | TGTGCGCGTGTGTGTGTGCACCTTTGTGTTCTAGCATTGTTGCA |
| | | CCCATTACAGAGCTGGGGGGAACTATTTTCCAAAATTATAGGTGA |
| | | GAACAGTTTCTTGGATTGTCTTTCAGTGAAGGTAAATTCCTCTGTA |
| | | AAAACTAACCATCATTCAGTAAAAACTGCAGGATTCCTTTGTCTTC |
| | | TCAAAAGCCTGTTTCTCATCCTAAATTAAAAATTATTCAGGAAATA |
| | | GAGAGGACATTATTGGAGGGGTGGAAATAAGTTGGTTTTCTTTTTA |
| | | TTGTATCTTTTGAGGATCCAGGGACTTCTACCATTTCCCATCTAAC |
| | | ATACAGAGAAGGATTCTCTAGGTCCCTGTCTATAGACTGCAGTAA |
| | | CTTTCCTATAGAACCAATTTGCAATTTTAGAAATTTCTAGGTCTAA |
| | | TTATTGACCCATTACAACCAAAGGTCAATGCATCCAGCCAATCTTC |
| | | CTTCTATCATCCCCTGCCCTTACTTCTATTAGGGACTGGGATTACA |
| | | GGCAAAACCCATCAAATGCCTCTTCTACCACTTTCCCATTTCTTAA |
| | | CCATTAGCCTCTAACTTCCTCTATTCAGTTTCTCATATGCTTTCATG |
| | | CCCATTGGGTCAGATAAAGGAACATTCATTTATTTGAGTAGGCATC |
| | | TGTTATGATCACTCCGGAAAAAAGATGACAATGGGTTACCTTGTCC |
| | | TCCTGGGCTTCTCTAACTGACATGGTCAAAATGCCCATATGAAGAT |
| | | AAGATGTTAAGAGCAAGATTTATGAAAAGCTGAGTATGATGGCAG |
| | | CTCTTGTCTCATAAAATAACTCGAAAGTTCCCAGTGAAAGACCAA |
| | | GAAATTTTACATCAAACCCAAACCGGCCAAATGGTCCAAGCTTCC |
| | | AAGCTGGGATCCATGGCTAAAGTTTCTACAAAATTCTGGGTACAA |
| | | TGTATAAACATTCACTTGGGGCTTTCTGTCTAGCCAGCACCAAGAG |
| | | GTCAAGTAATCAAGGACCAACTAGCCCTGCCATCTGTGAAAATAT |
| | | GTGCTATTTTCACGGCTTTAGTTCACAATTATGGCAAGACAAAAGT |
| | | TCCAAATAATTAGGAGCAAGACCATGGCAGGTTGACGGTTGAGTA |
| | | AGGTTCTCAATCAGCCGACAATTGTAGAGTTGGGGATGTGCAATG |
| | | TTTATGTCATGGTGTAAGTATGTGGCATGCTTGACTAGCTTGTGAG |
| | | GCACTGGAAGACTAGAAGGAATGAAAAATATGAATGAATCAATA |
| | | AATGCATAGTATAATTACTGTTATTTTGTCAGTATTGTTTTACCTAG |
| | | GTCACTATTGAATGCTCTGATTTGTCTCTTTATAAATAATAATATGT |
| | | TTTCTTCTTCAAAAGAACACTAGGATGAAGGTAGAGGTGCTTTTGG |
| | | CACAATGCCACAATTCTGATTTTTTTAAAACTGTATGCATGCATAA |
| | | AATGTTCTTGAGCCATTCTCTGCCTTGGAATAGCACTGGCTGGCAT |
| | | TCTGCATGTTTACTTTTATATGCTGAAGGCCCCCATCAACCTCAAA |
| | | CAGAGGCAAATCAATTTAACTTCTCATAGTGTTATTTTGTTCATCC |
| | | TAAAAGTTCAAGAGAGCCTTCCAAACTTCCAAAATTTCTCTCAATT |
| | | CAGTGAGGAGGAAAATTCAGAACACAGCATTTGAATGTTCTGCCC |
| | | AGATTTGTCACACACACAAGGAATGAGTGAAAGAGGGCAACACCC |
| | | TTTCCTCCTAACCCTGTGAACTCATCACTATTGCATTGAAATGACA |
| | | CCAAAAGGTAAAAACCCTAGGCCTCACATCTCCCAAGAACACTGC |
| | | AATAGGAGTTACTGCATACACCAGTTTAAGTAACTCTAGCATAAA |
| | | TTGTATGTCAGATGAAACAATGGCATTTTGGAGGCTTAAGAGAAA |
| | | AAGAATAATCAAATCCAGTTTTTAGGTACTAATGTGCTGAATCTTT |
| | | AGCACATAGCAGCAAAATTGCTAGAATCTGGTGTTTCACTTTTTAA |
| | | AATACCACATTTGAACCTTTCAGCAATTCCAAAATCAACTCCCTCT |
| | | GCGAAAGATAATAAGCTTAAACATTTTTTAAATTTAAAAATGTAA |
| | | CACAAACAAACAGCTAAGCAAACAAGCTGCCCATAAAATCAACA |
| | | GTCTGGGGAGCCCTGATCCTGAAGTATTTTACAACATCCTTCATGA |
| | | CTATTAAAGGCAACATAAACACCTCTTGTCAGCAAGGGAAACTAC |
| | | CCTTGGCATTTTTTTTCTTTGTTCCCCAGGCTTTTAAACCATTTTG |
| | | ATAGAGATTTTTTACATCACAGGCAGAAATATTTGAAATAGAGTC |
| | | AGGTGGTAGTCTTTAAAAGAGTAAGAAAGTTGCTAAGTCAAGATA |
| | | ATCTTGGAATAAAGTCCTCTGATTCCTGGGGATTCCTAGGGATGCC |
| | | CCAGTCACTAGAAAACAGAGCTGTAAGTCCACTCTCCCAGCACTC |
| | | AACGGGAGCTCCGGAAACCAAGGAGCTAGCTACTGTTTCCCCACAT |
| | | TCAGCCAGAGAAAGGGCAGCACTCTAGCATGCAAACTGCTTTGAC |
| | | AATAGTAACAATTAAAAAGTAAATTAAAAAGAATCATAAATAGCTG |

| SEQ ID NO | Description | Sequence |
|---|---|---|
| | | ATATTGATTAGGTACTTGCCCTGTGGCAAGAGCTATAGGGAATCA |
| | | CCTCATTTAATCTTCACATGAAGCTTGCAGAGTGAGTACCACAATT |
| | | ATCACTATTGTATAGACAGGAAAACTCAGGCTGAGTATGGCTAAG |
| | | TGTCTTGCCAACGTCTTGGGCTAACAAGCGGTCAAGCAGAATCCA |
| | | AACCCGAGATAGATAGACCACAGTGTGCTAATCAAGCACTGCACT |
| | | CTCTCCTGCATTTCTTAGTTGATATTTACCATATACAATCTGTCACT |
| | | TGTATGAGATGGCAGGGGGTTCTGTGCTATTTGTCCTTGTAGAGAA |
| | | TACCACAGGAAGAAAGTAAGCAGCCATGCAATATTTGCTGTTGAC |
| | | CTGAACTCCATTCCATCATTCCTGCAGGAAATTCGCATCCATTAAA |
| | | TGAGCATTTCCTGGTTTGCCACTTTGCTCAAACACTTTGCTTGGATC |
| | | TGGAGAGGATATAGAAGTGAAGGAAATATGCTACCTGCTCTCAAG |
| | | GAACTTATGTTTTAGTGGAGAGACAAACATGCAGAATTTACTCTAC |
| | | AGAACATCAATGCTTGAGCAAATGTAGACCCAGAGAGGGCTCTTA |
| | | CAGCACACAAGCCAGAACAGACTGATGGTGCTAACAATTAGGTTC |
| | | AAGGTTTTTCTAAACAGTAGACTCTCCTGCATACAACTATACCGCA |
| | | TGCCAGGTAAATGACTGAGGGTTATTACATCCAATTATAACACCA |
| | | CTGTGATGTAGGTGCTCTTACCCCACACTTTCATTTTACAGAAGAG |
| | | GAAATTGAGGACAGCACAATGTAGTGATTATCAAAGGTCACACGA |
| | | CTACTGTGTGGGAGAGCTAGGATTTAAACCAGATGCATAAGATGA |
| | | GGTCCTCCAAGAAACAGAAGATGAGAAGGTGTTAAATGAGCAGG |
| | | GGTTTTATTAGGGGGAATTAATGTGTGAACAGAAATAGGGGAGGA |
| | | TAGGCAAAGCCATCAGATTGCAAGGCAAGCCTAACCCCAAGGGAA |
| | | GGAGAGAGAGAGTAGATTGGTTGGAAACATTTTTGGTGGGTCT |
| | | ATGGTCTAAGGAAAGTTCAGCAAAGTCATCATGGAGTTTTTGAGC |
| | | CAAAGTTGGGCAATACAGTTGCCCAACAAATTTCTGTGTTTCTCAG |
| | | AAATAGGTCTGCCTCAATGTCCCCACCATACTTGGTCACTGGCTCT |
| | | TGGGAGGGGCCTGCCCTGTTCCAATCCACTAGAGCCAAAGAAGAG |
| | | CCGTTGTACTGGCAGGGGGTGGGGAATTCCTACAACCACATAAA |
| | | AAGTGGGGTGAGGTTTCCAGAAAAAAACGTGATGCTGGGCTAACC |
| | | AAAACTGTGTCCAGTAAGTACATATCCCTCACTCTGTTAAAGAAGC |
| | | AGCCACATAAACAAGGAGTACACGTTTCTCAAAATGTGCACCTTG |
| | | TTCTTTGGTTTTGAAGTCACATCCCAAAGTGCTGAGTAGATCGCAT |
| | | GACCCTCGCTTTGCCTGGCTGCCAGAGAGGAAAGGCTGATCCAAC |
| | | TCTCCTGGAATTTGAACTTGTGATTCCCTGAAGTAAAGAGATATCA |
| | | AAGTTGATACTGAGACATCTAAATCATCCTCCACCATTTCACATGT |
| | | CCCCAGGCCAAGCCAGCAAAATTGCTATAGCACATCCCTTTCAAC |
| | | AGGTAAAGGGCTGATATCTGAGCCCTCTTTCCAATCATCCACTGCT |
| | | CTTTTCTTCTCATTTTGCCCTTTTTGGGAGCAGGTCAATGCTGAGTT |
| | | AGTACTTTATGCTGTACAATAAGCTGCTGATATTCCATGCTGGACA |
| | | GAATTTTCCCAGTATTTTTTATAGAGTGCCAGGCTTTTCCTAGACTT |
| | | CATGTCATACAATACTTAACTTGTTTGGAGTGGGTGGAGATGGAA |
| | | ACATAGTCTATTGAAAACATCACTGCTTCCTCCCTGAAGTTTAAAG |
| | | AGCCTATTTTTATCCTTTTAGATTCTATCTCTCAGGCAAAATCTCAT |
| | | AAAGATAAGTGGGGAGGAAAAAAAGGGGGTTATAATACCTAGGG |
| | | AGTTTGCTTTTGCTAATTGAATACTGTGCTCCTAGACTTCTATAAAT |
| | | ACCATTACAAATGGGTCCCAGCTTGGTAATACTCACCCTCCTCA |
| | | TTGAGTCTTCTGTCCCATGGCACAGCCTTTCCCTCCAAACTAGCAT |
| | | CTACCCCCATCTGGAAGCATGGGCAGCTCATGATATTATCAACTAT |
| | | TGCTATTGGAAAGTGATTTGGACTTGAAAGCACTAGATATTTTTA |
| | | CCTCTTGGGGAGGCAGTTTAGCAGAGTGGTTAACTGGTGAGCTCC |
| | | AGAATCAGAAGGAATAGGTCCAAATTCCAACCACTATTACATCTC |
| | | CATCATAAGAAATTAGGCAAGTTGTTTATCCTAAGTTTCAGATTCC |
| | | TTAAAGATAAAACAGTCAAGACAGTAGTACTTATCCCTGAGAGAA |
| | | GTATAGGAAACAAGAAAATATATGCAATTTACATACATACTACAA |
| | | TCCCCAGCACATGACAAATGTTCAAGTAATGGGAACTGTTATTATT |
| | | TTAGCCCTTTGTCTATCAGTTTGTTCCTCTGTGACCTCAAGCACATT |
| | | ACTAAATGTTAGCGAGCTTCAGCTTGTACGTGGGACTGACAGGAA |
| | | TAACACCGCATCACCTCATGTGGTGATTGTAAGGATTCAGTGATAT |
| | | TATTTTGTAAACTGTAAAGCCTTTGCAAATGTTAAGCAAGATTATT |
| | | ATTATTGCCGTTGTTATTAGTCCTCAGTGATCTTTTTTTTTTTTTTT |
| | | TTTTTTTTTTTTTTTTTTTTTGGAGACAGAGTTTTACTCTGTCGCC |
| | | AAGGCTGGAATGCAGTGGCACAATCTCAGCTCACTGCAACCTCCG |
| | | CCTCCTGGGTTCAAGCAATTTTCCTGCCTCAGCCTCCTGAGTAGCT |
| | | GAAACTACAGGCACACGCCACCACACCAGGCTAATTTTTTGTATTT |
| | | TTAGTAGAGACGGGGTTTCACCATGTTGGCCAGGCTGGTCTCCAGC |
| | | TCCTGACCTCAAGTGATCTGCCCACCTCGGCCTCCAAAGTGCTGG |
| | | GATTACAGGTGTGAGCCACCACACCTGGCACAGTAATCTTAATTG |
| | | AAAAGTCTGTGGATAGCTTTCCAAAGGAAAGCTTGGAGCTTGGAT |
| | | AAGAACCAAGAGATAATGGGAGAAGGTGAATGGCCTCTTCAGGG |
| | | CCTTTTCTAGCACCCTAAATATGCGTGTCTGTCCATAATGGGTAAT |
| | | CATATATATCACAAATCAAACCCTCCACAAACTTATTTCCTAATGT |
| | | GTTTGTTAACCTTTCCTTCTAAAGGGTAAACTTCTTTAACCAACCC |
| | | CAGTGAGCTGGAGGATCAATGTTTTCTTAATAGTCTTACCTTCGTT |
| | | GGTGTCAATAGGAAACAGTATTTACTCACTACTGTTTTCCTTTTAA |

| SEQ ID NO | Description | Sequence |
|---|---|---|
| | | AAATCTGTCTAGTTGCATACTAGAAACAGTTTCAGCTGGTTTGTTT |
| | | GTATTGGACAAGCTGCTGAAGTGAAAAGTTTTTGCTTGACTGAATG |
| | | TGAGACAGTTTCATAACTCTTCAAGAAGTGCACCAAAGGTGGGTG |
| | | CCAGCTCTGATGACGGCTGCTTCTAACATGCCTCCACTTGCCGCCC |
| | | ATTGTCAAGGGTGGCTGGCGTAATTAAGTTAAGACAATGAGCAAA |
| | | GCAACAGATGCAACTGAGACCTAGTCCCTGAGTGCTTTTGTTTTGT |
| | | CACTGTCATTGTCTGCAACAAAGAAGTCACATGTGACAGCCTGGG |
| | | AAGAGAGCCAAATGCAAACCAGACGATATCCCAGCTGGTTTGAAT |
| | | GGCCTCCACCGTGCACGTGTGTGCATGGGAATCATGCTACTTGGTA |
| | | CAGCATCTGCTTCACTCAAGTGAGTTTCAGCCCATGGCTTTGCTGT |
| | | GATGCTGAGACAGACCCAGAAGAAACAGACCAGGGAATCCCTCC |
| | | GCTCAGACTTTACACTTTATACCTTGTGCTTTGAGAGAAAAGAAAA |
| | | AGAATCTCTCTATTGGAGACAAAAAATAGGATGTATGTGGTTGGT |
| | | CAATCTAACCTCAATTCTTTTTGCTATAGCCCCCCGCTAATTTAAA |
| | | GAGTGAAGCATAGATGGTATCTTAATGTTTTCTTGTAGAAATTTGG |
| | | GATTAATTTGGCTTGAGAGGAAGAATGGAGATTAAACGCTTTATG |
| | | AGGCTTTCTTTTAATTTGTTCCCATTTCATTCCTGAATATTTTCTTA |
| | | GTTTGGGCATTGCAGATGTTTAAAGAACTTCTTATTTTGAGCTGGT |
| | | ATGCCTCTTAAACAGAAAACAAAAGGTAAAATTCAAATTAGTGT |
| | | GTTTCTCCGCCTGTTAATTAATTTGGTTAGTAGTTAGGCAGAGAGA |
| | | TGGCATCCTTAATAATATCTATTTTGCGGGTTTGATCAGCTACAGA |
| | | CCATCAACAGTGTTGATTGAGAATTGAACAAAAACATTTCAAGGA |
| | | GTTTGGGAACATTAGGGATGCTATTCTGTGGCCCCATGTGTCCTTC |
| | | TCTCATTTTTCTAGAGAACTCCTATAAGAAAGCAGAACACGGCCA |
| | | GGCATGATGGCTCATGCCTGTAATCCCAGCACTTCAGGAGGCTGA |
| | | GGCAGGCAGATCACCTGAGGTCAGGAGTTCAAGACCAGCCTGGCC |
| | | AACATGGTGAAACCCTATCTCTATTAAAAATACAAAAAATTAGCT |
| | | GGGCATGATGGCGCGTGCCTGTAATCCCAGCTACTTGGGAGGCTG |
| | | AGGCAGGAGAATCACTTGAACTGGGAGGCAAAGGTTGCAGTGAG |
| | | CCTAGATCACACCACTGCACTCCAGCCTGGGTGACAGAGTGAGAC |
| | | TCCAACTCAAAAAAAAGAAAGAAAGAAAGAAAGCAGAACC |
| | | CAATGGAAGATTAAGAACACACATTTAGCTTACGCCTGTAATACC |
| | | AGCACTTTGGGAGGCCAAGGCGGGTGGATCACAAGGTCAGAAGTT |
| | | CGAGACCAACCTGGCCAATATGGTGAAACCCCATCTCTACTAAAA |
| | | AGTACAAAAATTAGCCATGCATGGTGGCAGGCGTCTGTAATCCCA |
| | | GCTACTACAGAGGCTGAGGCAGGAGAATCACTTGAACCCGGGAGG |
| | | CAGAGGTTGCAGTGAGCTGAGAACGCGCCACTGCACTCCAGCCTG |
| | | GGTGACAGAGCGAGACTCCATCTCAAAAAAAAAAAACAACAAA |
| | | AAAAACAAAACACAAGTTTACTGGGAACTTAGCAGTAGATGCTTT |
| | | GCACCACAACAAATGTATCTTAAGTGGTCTTTTGTGATATTTGAGG |
| | | GAAAGTGCCAGAATTTAAAACAAATGGCATTTCAAGTTATTCTAT |
| | | ACAAATGCCCAGTTTCTTTCTACCATCTTTTTTTCCTTTTTGCAGTG |
| | | GTCACTGAGCTATTTTAGTGAATGTTTTTACACAATGATGCCATCT |
| | | TCCTTCTACTCAGTCAGTACAAGATGTTGACCATCGACTCATAAAA |
| | | CACTAGCTACCTTTCATGAAGGACTTGGTGATAACTCTCATGTTCC |
| | | AAGTAGAACCGGAAAACATGTGTAAGAAAACCTGCCGATCCCTAT |
| | | GGGCCTTGGCCAATAGGTATTATTCCCAAGGGGTGGCAGTTTATCT |
| | | TTTTCCCCAGCCTTCATATTAAAACCTCTCACCTTCTCCAGGTCTCA |
| | | GGTCTGTGTAATCTCAAATGTGCTTTAGCTCCTCACAATATTGTAA |
| | | CTGTGTGGGTGTTCATTACCTTAGCCAGAAGACAGTTTACAGATTC |
| | | CAGGTCTCATGGAGAGAACTTTTGTTTTTGGTTATGAACCTCACTG |
| | | TATACCAATAATTATCCATTACATCCTTCTGTAGAGGGCTCTCTGG |
| | | CTAGAGATAAAACCAAAAAAAGAAGTACCTCAGGTTTATGCATAT |
| | | AAATGCCAGTTCCTCCTTGATTTTATTTCAAAACTCCTGTCTACATA |
| | | CTTTGCAATTTAAATACATTCAAGGATAAAGTAATAACTGTAGGA |
| | | AAAGTATTATAATATAATGACTTAGTTCTGCACATCACAAGGGGG |
| | | TCCCTCATACTCATTCATTCATTTCACTCATTTTACAGATATTTATT |
| | | GAGCACCTGCAATAACCTGCACACTGCTCTAGACACTGGGACTAT |
| | | AACAGTAAACAGACAGATACATCTCTGGTCTCACAGGGCTTCTATT |
| | | CTAAGCAAAACTCAATATCCAGGCCGGGTGCAGTGGCTCATGCCT |
| | | GGAATGCCAGCACTTTGGGAGACCAAGGCCAGGCAGATCACCTGA |
| | | GCCCACTAGTTGAAGACCAGCCTGGGCAATATAGCAAAACCCCGT |
| | | CTCTACAAAAAAAAAAAAAAAAAAAAAAAAATTGTCAAGGC |
| | | ATGGTGGCATGCGCCTGTGGTCCCAGCTACTTAGGAGGCTGAGGC |
| | | AGGAGGATTGTGTAAGCCTGGGAGGCAGAGGTTGCAGTGACCTGA |
| | | GATGGCACCACCACACTCCAGCCTGGGCAACAGAGTGAGACCCTG |
| | | TCCAAAAAAAAAAAACCCTCACTATCCTTAAGATAACATCATTGC |
| | | TTGTTGATGAGTGAATGTTAACACCCAAATTAGGAACCCAGGACTTT |
| | | TAGTCTTGGCATGGTTACTTTCCAATAAAGATGACAATACTAAGAA |
| | | GAGAAAAATGATTTAATAATGATAATAGTGGCTAATACTTATGTA |
| | | GTGCTTACCATGTGCCAGGTCTATTGTAAGTACTTTTATATATATT |
| | | AATTATTTAATCTTTGATCCTATAAGGTAGATATTATTGTTACCCTA |
| | | GTTTATAGATGAAGAAACGGAAACACAAGAGATTGCCACTCATAC |
| | | AAGTTTACACAGCCAGAAAATAGAAAAGCTACGAGTTGAGCTCAG |

| Sequence Listing | | |
|---|---|---|
| SEQ ID NO | Description | Sequence |
| | | CCCAGTATGTCTATGATTTTACAGACTCAAAATTAATTATAAGATT TCCTAATCTTCGATTTCTGAAACTCTGCCTTGCTCTAGAGGAAAAC AAGAAAAACAATGAAAAATAAATGTCTCTTTTTTACAAAAATTAA AACAGAACAAACTGCAATAAAACAACAGAGGATGAATCCAGAAT GTGATTGATTTTTTTTCTTACTAGGAAAGGATCTAGAGGCCAGAAG GCTGGATTTTTCAGGATCTCCTTTCAATCAATGAATCTGTGATAGA AGCAGATGAATCAAATCTCATCTTTGTGTGATTATAAAGCTGTCTG TGGTATTCACGCCACCAGGGGTACATAGAAGATGCCTGAGTGAGG TTTGGCAAAAGTACTAAGGGCCTGTCCACCTATACATGCCCTTCTC AGGAAAACCAAGGTTCAAGCTCTCTATTAGCTCAACTGGTAAGGC GTAAGACATGGAAGGTTGAGGCCCAATGTTAGAAATAGATGGATA CATAAAACTTCATCAAGTTAATGTCACTTTTTCTCCTTTATTTATAG |
| SEQ ID NO. 5 | IGF-1 (exon 6-2) | GAAGTACATTTGAAGAACGCAAGTAGAGGGAGTGCAGGAAACAA GAACTACAGGATGTAG |
| SEQ ID NO. 6 | IGF-1 (intron 4 used in IGF-1X6) | GTAAGCCCACCTGGGTGGGATCCAGCCATCCTCAAGTGGTCTCTCT CTTGTGCATGTGGGTGGGCCAAGCAGAAATCCTGCCCCATAGTCTC CTGGCTTACAAGTCAGAAAAGCTCCTTTGCACCAAAGGGATGGAT TACATCCCCATCTCTTTGGTCACTCTGCATTGCAAATTTCCCCTCCC ACCGCTATGGACGATGTGATGATTGGAAGATGTTACAAAACAGTG GCTAAACAAACATGGGCTTTGGTGTCAGACAAAAGTGAAGTCCTG GCTTTCTCACACACCAGCTTAGAGAGAAAAGACTTTTAGGTGAAT GTGGCAGGAAAGCGTGCTTGCTGGGGCAAAGGCAGATTCATTCTT TCTCTTCCCAG |
| SEQ ID NO. 7 | IGF-1 (intron 4 used in IGF-1X10) | GTAAGCCCACCTGGGTGGGATCCAGCCATCCTCAAGTGGTCTCTCT CTTGTGCATGTGGGTGGGCCAAGCAGAAATCCTGCCCCATAGTCTC CTGGCTTACAAGTCAGAAAAGCTCCTTTGCACCAAAGGGATGGAT TACATCCCCATCTCTTTGCTAAACAAACATGGGCTTTGGTGTCAGA CAAAAGTGAAGTCCTGGCTTTCTCACACACCAGCTTAGAGAGAAA AGACTTTTAGGTGAATGTGGCAGGAAAGCGTGCTTGCTGGGGCAA AGGCAGATTCATTCTTTCTCTTCCCAG |
| SEQ ID NO. 8 | IGF-1 (intron 5 used in IGF-1X6 and IGF-1X10) | CTTTTTCTCCTTTATTTATAG |
| SEQ ID NO. 9 | IGF-1X6 | ATGGGAAAAATCAGCAGTCTTCCAACCCAATTATTTAAGTGCTGCT TTTGTGATTTCTTGAAGGTGAAGATGCACACCATGTCCTCCTCGCA TCTCTTCTACCTGGCGCTGTGCCTGCTCACCTTCACCAGCTCTGCCA CGGCTGGACCGGAGACGCTCTGCGGGGCTGAGCTGGTGGATGCTC TTCAGTTCGTGTGTGGAGACAGGGGCTTTTATTTCAACAAGCCCAC AGGGTATGGCTCCAGCAGTCGGAGGGCGCCTCAGACAGGCATCGT GGATGAGTGCTGCTTCCGGAGCTGTGATCTAAGGAGGCTGGAGAT GTATTGCGCACCCCTCAAGCCTGCCAAGTCAGCTCGCTCTGTCCGT GCCCAGCGCCACACCGACATGCCCAAGACCCAGAAGGTAAGCCCA CCTGGGTGGGATCCAGCCATCCTCAAGTGGTCTCTCTCTTGTGCAT GTGGGTGGGCCAAGCAGAAATCCTGCCCCATAGTCTCCTGGCTTA CAAGTCAGAAAAGCTCCTTTGCACCAAAGGGATGGATTACATCCC CATCTCTTTGGTCACTCTGCATTGCAAATTTCCCCTCCCACCGCTAT GGACGATGTGATGATTGGAAGATGTTACAAAACAGTGGCTAAACA AACATGGGCTTTGGTGTCAGACAAAAGTGAAGTCCTGGCTTTCTCA CACACCAGCTTAGAGAGAAAAGACTTTTAGGTGAATGTGGCAGGA AAGCGTGCTTGCTGGGGCAAAGGCAGATTCATTCTTTCTCTTCCCA GTATCAGCCCCCATCTACCAACAAGAACACGAAGTCTCAGAGAAG GAAAGGAAGTACATTTGAAGAACGCAAGTAGCTTTTTCTCCTTTAT TTATAGGAAGTACATTTGAAGAACGCAAGTAGAGGGAGTGCAGGA AACAAGAACTACAGGATGTAG |
| SEQ ID NO. 10 | IGF-1X10 | ATGGGAAAAATCAGCAGTCTTCCAACCCAATTATTTAAGTGCTGCT TTTGTGATTTCTTGAAGGTGAAGATGCACACCATGTCCTCCTCGCA TCTCTTCTACCTGGCGCTGTGCCTGCTCACCTTCACCAGCTCTGCCA CGGCTGGACCGGAGACGCTCTGCGGGGCTGAGCTGGTGGATGCTC TTCAGTTCGTGTGTGGAGACAGGGGCTTTTATTTCAACAAGCCCAC AGGGTATGGCTCCAGCAGTCGGAGGGCGCCTCAGACAGGCATCGT GGATGAGTGCTGCTTCCGGAGCTGTGATCTAAGGAGGCTGGAGAT GTATTGCGCACCCCTCAAGCCTGCCAAGTCAGCTCGCTCTGTCCGT GCCCAGCGCCACACCGACATGCCCAAGACCCAGAAGGTAAGCCCA CCTGGGTGGGATCCAGCCATCCTCAAGTGGTCTCTCTCTTGTGCAT GTGGGTGGGCCAAGCAGAAATCCTGCCCCATAGTCTCCTGGCTTA |

| SEQ ID NO | Description | Sequence |
|---|---|---|
| | | CAAGTCAGAAAAGCTCCTTTGCACCAAAGGGATGGATTACATCCC<br>CATCTCTTTGCTAAACAAACATGGGCTTTGGTGTCAGACAAAAGTG<br>AAGTCCTGGCTTTCTCACACACCAGCTTAGAGAGAAAAGACTTTTA<br>GGTGAATGTGGCAGGAAAGCGTGCTTGCTGGGGCAAAGGCAGATT<br>CATTCTTTCTCTTCCCAGTATCAGCCCCCATCTACCAACAAGAACA<br>CGAAGTCTCAGAGAAGGAAAGGAAGTACATTTGAAGAACGCAAG<br>TAGCTTTTTCTCCTTTATTTATAGGAAGTACATTTGAAGAACGCAA<br>GTAGAGGGAGTGCAGGAAACAAGAACTACAGGATGTAG |
| SEQ ID NO. 14 | aa sequence of Class I IGF-1Ea | MGKISSLPTQLFKCCFCDFLKVKMHTMSSSHLFYLALCLLTFTSSATA<br>GPETLCGAELVDALQFVCGDRGFYFNKPTGYGSSSRRAPQTGIVDEC<br>CFRSCDLRRLEMYCAPLKPAKSARSVRAQRHTDMPKTQKEVHLKNA<br>SRGSAGNKNYRM |
| SEQ ID NO. 15 | nucleotide sequence of Class I IGF-1Ea | ATGGGAAAAATCAGCAGTCTTCCAACCCAATTATTTAAGTGCTGCT<br>TTTGTGATTTCTTGAAGGTGAAGATGCACACCATGTCCTCCTCGCA<br>TCTCTTCTACCTGGCGCTGTGCCTGCTCACCTTCACCAGCTCTGCCA<br>CGGCTGGACCGGAGACGCTCTGCGGGGCTGAGCTGGTGGATGCTC<br>TTCAGTTCGTGTGTGGAGACAGGGGCTTTTATTTCAACAAGCCCAC<br>AGGGTATGGCTCCAGCAGTCGGAGGGCGCCTCAGACAGGCATCGT<br>GGATGAGTGCTGCTTCCGGAGCTGTGATCTAAGGAGGCTGGAGAT<br>GTATTGCGCACCCCTCAAGCCTGCCAAGTCAGCTCGCTCTGTCCGT<br>GCCCAGCGCCACACCGACATGCCCAAGACCCAGAAGGAAGTACAT<br>TTGAAGAACGCAAGTAGAGGGAGTGCAGGAAACAAGAACTACAG<br>GATGTAG |
| SEQ ID NO. 16 | aa sequence of Class I IGF-1 Ec | MGKISSLPTQLFKCCFCDFLKVKMHTMSSSHLFYLALCLLTFTSSATA<br>GPETLCGAELVDALQFVCGDRGFYFNKPTGYGSSSRRAPQTGIVDEC<br>CFRSCDLRRLEMYCAPLKPAKSARSVRAQRHTDMPKTQKYQPPSTN<br>KNTKSQRRKGSTFEERK |
| SEQ ID NO. 17 | nucleotide sequence of Class I IGF-1Ec | ATGGGAAAAATCAGCAGTCTTCCAACCCAATTATTTAAGTGCTGCT<br>TTTGTGATTTCTTGAAGGTGAAGATGCACACCATGTCCTCCTCGCA<br>TCTCTTCTACCTGGCGCTGTGCCTGCTCACCTTCACCAGCTCTGCCA<br>CGGCTGGACCGGAGACGCTCTGCGGGGCTGAGCTGGTGGATGCTC<br>TTCAGTTCGTGTGTGGAGACAGGGGCTTTTATTTCAACAAGCCCAC<br>AGGGTATGGCTCCAGCAGTCGGAGGGCGCCTCAGACAGGCATCGT<br>GGATGAGTGCTGCTTCCGGAGCTGTGATCTAAGGAGGCTGGAGAT<br>GTATTGCGCACCCCTCAAGCCTGCCAAGTCAGCTCGCTCTGTCCGT<br>GCCCAGCGCCACACCGACATGCCCAAGACCCAGAAGTATCAGCCC<br>CCATCTACCAACAAGAACACGAAGTCTCAGAGAAGGAAAGGAAG<br>TACATTTGAAGAACGCAAGTAG |
| SEQ ID NO. 18 | aa sequence of Class II IGF-1 Ea | MITPTVKMHTMSSSHLFYLALCLLTFTSSATAGPETLCGAELVDALQF<br>VCGDRGFYFNKPTGYGSSSRRAPQTGIVDECCFRSCDLRRLEMYCAP<br>LKPAKSARSVRAQRHTDMPKTQKEVHLKNASRGSAGNKNYRM |
| SEQ ID NO. 19 | nucleotide sequence of Class II IGF-1Ea | ATGATTACACCTACAGTGAAGATGCACACCATGTCCTCCTCGCATC<br>TCTTCTACCTGGCGCTGTGCCTGCTCACCTTCACCAGCTCTGCCAC<br>GGCTGGACCGGAGACGCTCTGCGGGGCTGAGCTGGTGGATGCTCT<br>TCAGTTCGTGTGTGGAGACAGGGGCTTTTATTTCAACAAGCCCACA<br>GGGTATGGCTCCAGCAGTCGGAGGGCGCCTCAGACAGGCATCGTG<br>GATGAGTGCTGCTTCCGGAGCTGTGATCTAAGGAGGCTGGAGATG<br>TATTGCGCACCCCTCAAGCCTGCCAAGTCAGCTCGCTCTGTCCGTG<br>CCCAGCGCCACACCGACATGCCCAAGACCCAGAAGGAAGTACATT<br>TGAAGAACGCAAGTAGAGGGAGTGCAGGAAACAAGAACTACAGG<br>ATGTAG |
| SEQ ID NO. 20 | aa sequence of Class I IGF- 1 Eb | MGKISSLPTQLFKCCFCDFLKVKMHTMSSSHLFYLALCLLTFTSSATA<br>GPETLCGAELVDALQFVCGDRGFYFNKPTGYGSSSRRAPQTGIVDEC<br>CFRSCDLRRLEMYCAPLKPAKSARSVRAQRHTDMPKTQKYQPPSTN<br>KNTKSQRRKGWPKTHPGGEQKEGTEASLQIRGKKKEQRREIGSRNAE<br>CRGKKGK |
| SEQ ID NO. 21 | nucleotide sequence of Class I IGF-1Eb | ATGGGAAAAATCAGCAGTCTTCCAACCCAATTATTTAAGTGCTGCT<br>TTTGTGATTTCTTGAAGGTGAAGATGCACACCATGTCCTCCTCGCA<br>TCTCTTCTACCTGGCGCTGTGCCTGCTCACCTTCACCAGCTCTGCCA<br>CGGCTGGACCGGAGACGCTCTGCGGGGCTGAGCTGGTGGATGCTC<br>TTCAGTTCGTGTGTGGAGACAGGGGCTTTTATTTCAACAAGCCCAC<br>AGGGTATGGCTCCAGCAGTCGGAGGGCGCCTCAGACAGGCATCGT<br>GGATGAGTGCTGCTTCCGGAGCTGTGATCTAAGGAGGCTGGAGAT<br>GTATTGCGCACCCCTCAAGCCTGCCAAGTCAGCTCGCTCTGTCCGT<br>GCCCAGCGCCACACCGACATGCCCAAGACCCAGAAGTATCAGCCC |

| SEQ ID NO | Description | Sequence |
|---|---|---|
| | | CCATCTACCAACAAGAACACGAAGTCTCAGAGAAGGAAAGGTTGG CCAAAGACACATCCAGGAGGGGAACAGAAGGAGGGGACAGAAGC AAGTCTGCAGATCAGAGGAAAGAAGAAAGAGCAGAGGAGGGAGA TTGGAAGTAGAAATGCTGAATGCAGAGGCAAAAAAGGAAAATGA |
| SEQ ID NO. 22 | F primer of the first primer pair (pTx) | AGCTGGCAATTCCGGTTCGCTTGCTGCGTCAGACCCCGTA |
| SEQ ID NO. 23 | R primer of the first primer pair (pTx) | TACGGGGTCTGACGCAGCAAGCGAACCGGAATTGCCAGCT |
| SEQ ID NO. 24 | F primer of the second primer pair (pTx) | CTAATCCATAACATGGCTCTAGACTTAAGGCAGCGGCAGA |
| SEQ ID NO. 25 | R primer of the second primer pair (pTx) | TCTGCCGCTGCCTTAAGTCTAGAGCCATGTTATGGATTAG |
| SEQ ID NO. 26 | pTx | CAGGGTCGGAACAGGAGAGCGCACGAGGGAGCTTCCAGGGGGAA ACGCCTGGTATCTTTATAGTCCTGTCGGGTTTCGCCACCTCTGACTT GAGCGTCGATTTTTGTGATGCTCGTCAGGGGGGCGGAGCCTATGG AAAAACGCCAGCAACGCGGCCTTTTTACGGTTCCTGGCCTTTTGCT GGCCTTTTGCTCACATGCGCGTTGACATTGATTATTGACTAGTTAT TAATAGTAATCAATTACGGGGTCATTAGTTCATAGCCCATATATGG AGTTCCGCGTTACATAACTTACGGTAAATGGCCCGCCTGGCTGACC GCCCAACGACCCCCGCCCATTGACGTCAATAATGACGTATGTTCCC ATAGTAACGCCAATAGGGACTTTCCATTGACGTCAATGGGTGGAG TATTTACGGTAAACTGCCCACTTGGCAGTACATCAAGTGTATCATA TGCCAAGTCCGCCCCCTATTGACGTCAATGACGGTAAATGGCCCG CCTGGCATTATGCCCAGTACATGACCTTACGGGACTTTCCTACTTG GCAGTACATCTACGTATTAGTCATCGCTATTACCATGGTGATGCGG TTTTGGCAGTACACCAATGGGCGTGGATAGCGGTTTGACTCACGG GGATTTCCAAGTCTCCACCCCATTGACGTCAATGGGAGTTTGTTTT GGCACCAAAATCAACGGGACTTTCCAAAATGTCGTAATAACCCCG CCCCGTTGACGCAAATGGGCGGTAGGCGTGTACGGTGGGAGGTCT ATATAAGCAGAGCTCGTTTAGTGAACCGTCAGATCGCCTGGAGAC GCCATCCACGCTGTTTTGACCTCCATAGAAGACACCGGGACCGAT CCAGCCTCCGCGGCCGGGAACGGTGCATTGGAACGCGGATTCCCC GTGCCAAGAGTGACGTAAGTACCGCCTATAGACTCTATAGGCACA CCCCTTTGGCTCTTATGCATGCTATACTGTTTTTGGCTTGGGGCCTA TACACCCCCGCTTCCTTATGCTATAGGTGATGGTATAGCTTAGCCT ATAGGTGTGGGTTATTGACCATTATTGACCACTCCCTATTGGTGA CGATACTTTCCATTACTAATCCATAACATGGCTCTAGACTTAAGGC AGCGGCAGAAGAAGATGTAGGCAGCTGAGTTGTTGTATTCTGATA AGAGTCAGAGGTAACTCCCGTTGCGGTGCTGTTAACGGTGGAGGG CAGTGTAGTCTGAGCAGTACTCGTTGCTGCCGCGCGCGCCACCAG ACATAATAGCTGACAGACTAACAGACTGTTCCTTTCCATGGGTCTT TTCTGCAGTCACCGTCCTTGACACGAAGCTTATCGATGTCGACCTC GAGTCTAGAGGGCCCGTTTAAACCCGCTGATCAGCCTCGACTGTG CCTTCTAGTTGCCAGCCATCTGTTGTTTGCCCCTCCCCCGTGCCTTC CTTGACCCTGGAAGGTGCCACTCCCACTGTCCTTTCCTAATAAAAT GAGGAAATTGCATCGCATTGTCTGAGTAGGTGTCATTCTATTCTGG GGGGTGGGGTGGGCAGGACAGCAAGGGGGAGGATTGGGAAGAC AATAGCAGGCATGCTGGGGAGTCGAAATTCAGAAGAACTCGTCAA GAAGGCGATAGAAGGCGATGCGCTGCGAATCGGGAGCGGCGATA CCGTAAAGCACGAGGAAGCGGTCAGCCCATTCGCCGCCAAGCTCT TCAGCAATATCACGGGTAGCCAACGCTATGTCCTGATAGCGGTCC GCCACACCCAGCCGGCCACAGTCGATGAATCCAGAAAAGCGGCCA TTTTCCACCATGATATTCGGCAAGCAGGCATCGCCATGGGTCACGA CGAGATCCTCGCCGTCGGGCATGCTCGCCTTGAGCCTGGCGAACA GTTCGGCTGGCGCGAGCCCCTGATGCTCTTCGTCCAGATCATCCTG ATCGACAAGACCGGCTTCCATCCGAGTACGTGCTCGCTCGATGCG ATGTTTCGCTTGGTGGTCGAATGGGCAGGTAGCCGGATCAAGCGT ATGCAGCCGCCGCATTGCATCAGCCATGATGGATACTTTCTCGGCA GGAGCAAGGTGAGATGACAGGAGATCCTGCCCCGGCACTTCGCCC |

| SEQ ID NO | Description | Sequence |
|---|---|---|
| | | AATAGCAGCCAGTCCCTTCCCGCTTCAGTGACAACGTCGAGCACA
GCTGCGCAAGGAACGCCCGTCGTGGCCAGCCACGATAGCCGCGCT
GCCTCGTCTTGCAGTTCATTCAGGGCACCGGACAGGTCGGTCTTGA
CAAAAAGAACCGGGCGCCCCTGCGCTGACAGCCGGAACACGGCG
GCATCAGAGCAGCCGATTGTCTGTTGTGCCCAGTCATAGCCGAAT
AGCCTCTCCACCCAAGCGGCCGGAGAACCTGCGTGCAATCCATCT
TGTTCAATCATGCGAAACGATCCTCATCCTGTCTCTTGATCAGATC
TTGATCCCCTGCGCCATCAGATCCTTGGCGGCAAGAAAGCCATCC
AGTTTACTTTGCAGGGCTTCCCAACCTTACCAGAGGGCGCCCCAGC
TGGCAATTCCGGTTCGCTTGCTGCGTCAGACCCCGTAGAAAAGATC
AAAGGATCTTCTTGAGATCCTTTTTTTCTGCGCGTAATCTGCTGCTT
GCAAACAAAAAAACCACCGCTACCAGCGGTGGTTTGTTTGCCGGA
TCAAGAGCTACCAACTCTTTTTCCGAAGGTAACTGGCTTCAGCAGA
GCGCAGATACCAAATACTGTTCTTCTAGTGTAGCCGTAGTTAGGCC
ACCACTTCAAGAACTCTGTAGCACCGCCTACATACCTCGCTCTGCT
AATCCTGTTACCAGTGGCTGCTGCCAGTGGCGATAAGTCGTGTCTT
ACCGGGTTGGACTCAAGACGATAGTTACCGGATAAGGCGCAGCGG
TCGGGCTGAACGGGGGGTTCGTGCACACAGCCCAGCTTGGAGCGA
ACGACCTACACCGAACTGAGATACCTACAGCGTGAGCTATGAGAA
AGCGCCACGCTTCCCGAAGGGAGAAAGGCGGACAGGTATCCGGTA
AGCGGCAGGGTCGGAACAGGAGAGCGCACGAGGGAGCTTCCAGG
GGGAAACGCCTGGTATCTTTATAGTCCTGTCGGGTTTCGCCACCTC
TGACTTGAGCGTCGATTTTTGTGATGCTCGTCAGGGGGCGGAGCC
TATGGAAAAACGCCAGCAACGCGGCCTTTTTACGGTTCCTGGCCTT
TTGCTGGCCTTTTGCTCACATG |
| SEQ ID NO. 27 | pTx-IGF-1X10 | CAGGGTCGGAACAGGAGAGCGCACGAGGGAGCTTCCAGGGGGAA
ACGCCTGGTATCTTTATAGTCCTGTCGGGTTTCGCCACCTCTGACTT
GAGCGTCGATTTTTGTGATGCTCGTCAGGGGGCGGAGCCTATGGA
AAAACGCCAGCAACGCGGCCTTTTTACGGTTCCTGGCCTTTTGCT
GGCCTTTTGCTCACATGCGCGTTGACATTGATTATTGACTAGTTAT
TAATAGTAATCAATTACGGGGTCATTAGTTCATAGCCCATATATGG
AGTTCCGCGTTACATAACTTACGGTAAATGGCCCGCCTGGCTGACC
GCCCAACGACCCCCGCCCATTGACGTCAATAATGACGTATGTTCCC
ATAGTAACGCCAATAGGGACTTTCCATTGACGTCAATGGGTGGAG
TATTTACGGTAAACTGCCCACTTGGCAGTACATCAAGTGTATCATA
TGCCAAGTCCGCCCCCTATTGACGTCAATGACGGTAAATGGCCCG
CCTGGCATTATGCCCAGTACATGACCTTACGGGACTTTCCTACTTG
GCAGTACATCTACGTATTAGTCATCGCTATTACCATGGTGATGCGG
TTTTGGCAGTACACCAATGGGCGTGGATAGCGGTTTGACTCACGG
GGATTTCCAAGTCTCCACCCCATTGACGTCAATGGGAGTTTGTTTT
GGCACCAAAATCAACGGGACTTTCCAAAATGTCGTAATAACCCCG
CCCCGTTGACGCAAATGGGCGGTAGGCGTGTACGGTGGGAGGTCT
ATATAAGCAGAGCTCGTTTAGTGAACCGTCAGATCGCCTGGAGAC
GCCATCCACGCTGTTTTGACCTCCATAGAAGACACCGGGACCGAT
CCAGCCTCCGCGGCCGGGAACGGTGCATTGGAACGCGGATTCCCC
GTGCCAAGAGTGACGTAAGTACCGCCTATAGACTCTATAGGCACA
CCCCTTTGGCTCTTATGCATGCTATACTGTTTTTGGCTTGGGGCCTA
TACACCCCGCTTCCTTATGCTATAGGTGATGGTATAGCTTAGCCT
ATAGGTGTGGGTTATTGACCATTATTGACCACTCCCCTATTGGTGA
CGATACTTTCCATTACTAATCCATAACATGGCTCTAGACTTAAGGC
AGCGGCAGAAGAAGATGTAGGCAGCTGAGTTGTTGTATTCTGATA
AGAGTCAGAGGTAACTCCCGTTGCGGTGCTGTTAACGGTGGAGGG
CAGTGTAGTCTGAGCAGTACTCGTTGCTGCCGCGCGCGCCACCAG
ACATAATAGCTGACAGACTAACAGACTGTTCCTTTCCATGGGTCTT
TTCTGCAGTCACCGTCCTTGACACGAAGCTTATCGATATGGGAAA
ATCAGCAGTCTTCCAACCCAATTATTTAAGTGCTGCTTTTGTGATTT
CTTGAAGGTGAAGATGCACACCATGTCCTCCTCGCATCTCTTCTAC
CTGGCGCTGTGCCTGCTCACCTTCACCAGCTCTGCCACGGCTGGAC
CGGAGACGCTCTGCGGGGCTGAGCTGGTGGATGCTCTTCAGTTCGT
GTGTGGAGACAGGGGCTTTTATTTCAACAAGCCCACAGGGTATGG
CTCCAGCAGTCGGAGGGCGCCTCAGACAGGCATCGTGGATGAGTG
CTGCTTCCGGAGCTGTGATCTAAGGAGGCTGGAGATGTATTGCGC
ACCCCTCAAGCCTGCCAAGTCAGCTCGCTCTGTCCGTGCCCAGCGC
CACACCGACATGCCCAAGACCCAGAAGGTAAGCCCACCTGGGTGG
GATCCAGCCATCCTCAAGTGGTCTCTCTCTTGTGCATGTGGGTGGG
CCAAGCAGAAATCCTGCCCCATAGTCTCCTGGCTTACAAGTCAGA
AAAGCTCCTTTGCACCAAAGGGATGGATTACATCCCCATCTCTTTG
CTAAACAAACATGGGCTTTGGTGTCAGACAAAAGTGAAGTCCTGG
CTTTCTCACACACCAGCTTAGAGAGAAAAGACTTTTAGGTGAATGT
GGCAGGAAAGCGTGCTTGCTGGGCAAAGGCAGATTCATTCTTTC
TCTTCCCAGTATCAGCCCCCATCTACCAACAAGAACACGAAGTCTC
AGAGAAGGAAAGGAAGTACATTTGAAGAACGCAAGTAGCTTTTTC
TCCTTTATTTATAGGAAGTACATTTGAAGAACGCAAGTAGAGGGA |

| SEQ ID NO | Description | Sequence |
|---|---|---|
| | | GTGCAGGAAACAAGAACTACAGGATGTAGGTCGACCTCGAGTCTA
GAGGGCCCGTTTAAACCCGCTGATCAGCCTCGACTGTGCCTTCTAG
TTGCCAGCCATCTGTTGTTTGCCCCTCCCCCGTGCCTTCCTTGACCC
TGGAAGGTGCCACTCCCACTGTCCTTTCCTAATAAAATGAGGAAAT
TGCATCGCATTGTCTGAGTAGGTGTCATTCTATTCTGGGGGGTGGG
GTGGGGCAGGACAGCAAGGGGGAGGATTGGGAAGACAATAGCAG
GCATGCTGGGGAGTCGAAATTCAGAAGAACTCGTCAAGAAGGCGA
TAGAAGGCGATGCGCTGCGAATCGGGAGCGGCGATACCGTAAAGC
ACGAGGAAGCGGTCAGCCCATTCGCCGCCAAGCTCTTCAGCAATA
TCACGGGTAGCCAACGCTATGTCCTGATAGCGGTCCGCCACACCC
AGCCGGCCACAGTCGATGAATCCAGAAAAGCGGCCATTTTCCACC
ATGATATTCGGCAAGCAGGCATCGCCATGGGTCACGACGAGATCC
TCGCCGTCGGGCATGCTCGCCTTGAGCCTGGCGAACAGTTCGGCTG
GCGCGAGCCCCTGATGCTCTTCGTCCAGATCATCCTGATCGACAAG
ACCGGCTTCCATCCGAGTACGTGCTCGCTCGATGCGATGTTTCGCT
TGGTGGTCGAATGGGCAGGTAGCCGGATCAAGCGTATGCAGCCGC
CGCATTGCATCAGCCATGATGGATACTTTCTCGGCAGGAGCAAGG
TGAGATGACAGGAGATCCTGCCCCGGCACTTCGCCCAATAGCAGC
CAGTCCCTTCCCGCTTCAGTGACAACGTCGAGCACAGCTGCGCAA
GGAACGCCCGTCGTGGCCAGCCACGATAGCCGCGCTGCCTCGTCT
TGCAGTTCATTCAGGGCACCGGACAGGTCGGTCTTGACAAAAAGA
ACCGGGCGCCCCTGCGCTGACAGCCGGAACACGGCGGCATCAGAG
CAGCCGATTGTCTGTTGTGCCCAGTCATAGCCGAATAGCCTCTCCA
CCCAAGCGGCCGGAGAACCTGCGTGCAATCCATCTTGTTCAATCAT
GCGAAACGATCCTCATCCTGTCTCTTGATCAGATCTTGATCCCCTG
CGCCATCAGATCCTTGGCGGCAAGAAAGCCATCCAGTTTACTTTGC
AGGGCTTCCCAACCTTACCAGAGGGCGCCCCAGCTGGCAATTCCG
GTTCGCTTGCTGCGTCAGACCCCGTAGAAAAGATCAAAGGATCTT
CTTGAGATCCTTTTTTTCTGCGCGTAATCTGCTGCTTGCAAACAAA
AAAACCACCGCTACCAGCGGTGGTTTGTTTGCCGGATCAAGAGCT
ACCAACTCTTTTTCCGAAGGTAACTGGCTTCAGCAGAGCGCAGAT
ACCAAATACTGTTCTTCTAGTGTAGCCGTAGTTAGGCCACCACTTC
AAGAACTCTGTAGCACCGCCTACATACCTCGCTCTGCTAATCCTGT
TACCAGTGGCTGCTGCCAGTGGCGATAAGTCGTGTCTTACCGGGTT
GGACTCAAGACGATAGTTACCGGATAAGGCGCAGCGGTCGGGCTG
AACGGGGGGTTCGTGCACACAGCCCAGCTTGGAGCGAACGACCTA
CACCGAACTGAGATACCTACAGCGTGAGCTATGAGAAAGCGCCAC
GCTTCCCGAAGGGAGAAAGGCGGACAGGTATCCGGTAAGCGGCA
GGGTCGGAACAGGAGAGCGCACGAGGGAGCTTCCAGGGGGAAAC
GCCTGGTATCTTTATAGTCCTGTCGGGTTTCGCCACCTCTGACTTG
AGCGTCGATTTTTGTGATGCTCGTCAGGGGGCGGAGCCTATGGA
AAAACGCCAGCAACGCGGCCTTTTTACGGTTCCTGGCCTTTTGCTG
GCCTTTTGCTCACATG |

What is claimed is:

1. An IGF-1 encoding DNA construct, comprising:
a first polynucleotide that has the sequence of (SEQ ID NO: 1) or a degenerate thereof;
a second polynucleotide that is the sequence of SEQ ID NO: 6 or SEQ ID NO: 7;
a third polynucleotide that has the sequence of (SEQ ID NO: 3) or a degenerate thereof;
a fourth polynucleotide that has the sequence of (SEQ ID NO: 4) or a fragment thereof; and
a fifth polynucleotide that has the sequence of (SEQ ID NO: 5) or a degenerate thereof,
wherein the first polynucleotide, the second polynucleotide, the third polynucleotide, the fourth polynucleotide and the fifth polynucleotide are linked in sequential 5' to 3' order.

2. The IGF-1 encoding DNA construct of claim 1, wherein the fourth polynucleotide is a polynucleotide of SEQ ID NO: 8.

3. The IGF-1 encoding DNA construct of claim 1, further comprising a plasmid vector.

4. The IGF-1 encoding DNA construct of claim 3, wherein the plasmid vector is pCK.

5. The IGF-1 encoding DNA construct of claim 4, wherein the construct is pCK-IGF-1X6 or pCK-IGF-1X10.

6. The IGF-1 encoding DNA construct of claim 3, wherein the plasmid vector is pTx.

7. The IGF-1 encoding DNA construct of claim 6, wherein the construct is pTx-IGF-1X10.

8. The IGF-1 encoding DNA construct of claim 6, wherein the construct is pTx plasmid containing IGF-1X6 having the sequence of SEQ ID NO: 9.

9. A pharmaceutical composition comprising the IGF-encoding DNA construct of claim 8.

10. A pharmaceutical composition comprising the IGF-1 encoding DNA construct of claim 1.

11. The pharmaceutical composition of claim 10, wherein the IGF-1 encoding DNA construct is pCK-IGF-1X6, pCK-IGF-1X10 or pTx-IGF-1X10.

12. An IGF-1 encoding DNA construct, comprising:
a first polynucleotide that has the sequence of SEQ ID NO: 1 or a degenerate thereof;
a second polynucleotide that has the sequence of SEQ ID NO: 2 or a fragment thereof;
a third polynucleotide that has the sequence of SEQ ID NO: 3 or a degenerate thereof;
a fourth polynucleotide that is the sequence of SEQ ID NO: 8; and
a fifth polynucleotide that has the sequence of SEQ ID NO: 5 or a degenerate thereof,
wherein the first polynucleotide, the second polynucleotide, the third polynucleotide, the fourth polynucleotide and the fifth polynucleotide are linked in sequential 5' to 3' order.

13. The IGF-1 encoding DNA construct of claim 12, wherein the second polynucleotide has the sequence of SEQ ID NO: 6 or SEQ ID NO: 7.

14. The IGF-1 encoding DNA construct of claim 12, further comprising a plasmid vector.

15. A pharmaceutical composition comprising the IGF-1 encoding DNA construct of claim 12.

* * * * *

UNITED STATES PATENT AND TRADEMARK OFFICE
CERTIFICATE OF CORRECTION

PATENT NO.         : 11,510,999 B2
APPLICATION NO.    : 16/513564
DATED              : November 29, 2022
INVENTOR(S)        : Junghun Lee, Nayeon Lee and Kyeong Ryang Ko It is certified that error appears in the above-identified patent and that said Letters Patent is hereby corrected as shown below:

In the Claims

In Column 81, Claim 1, Line 18, delete "(SEQ" and insert -- SEQ --, therefor.

In Column 81, Claim 1, Line 19, delete "1)" and insert -- 1 --, therefor.

In Column 81, Claim 1, Line 22, delete "(SEQ" and insert -- SEQ --, therefor.

In Column 81, Claim 1, Line 23, delete "3)" and insert -- 3 --, therefor.

In Column 81, Claim 1, Line 24, delete "(SEQ" and insert -- SEQ --, therefor.

In Column 81, Claim 1, Line 25, delete "4)" and insert -- 4 --, therefor.

In Column 81, Claim 1, Line 26, delete "(SEQ" and insert -- SEQ --, therefor.

In Column 81, Claim 1, Line 27, delete "5)" and insert -- 5 --, therefor.

In Column 82, Claim 9, Lines 17-18, delete "IGF-encoding" and insert -- IGF-1 encoding --, therefor.

Signed and Sealed this
Twenty-eighth Day of March, 2023

Katherine Kelly Vidal
*Director of the United States Patent and Trademark Office*

SEQUENCE LISTING

<160> NUMBER OF SEQ ID NOS: 29

<210> SEQ ID NO 1
<211> LENGTH: 402
<212> TYPE: DNA
<213> ORGANISM: Homo sapiens

<400> SEQUENCE: 1

```
atgggaaaaa tcagcagtct tccaacccaa ttatttaagt gctgcttttg tgatttcttg      60
aaggtgaaga tgcacaccat gtcctcctcg catctcttct acctggcgct gtgcctgctc     120
accttcacca gctctgccac ggctggaccg gagacgctct gcggggctga gctggtggat     180
gctcttcagt tcgtgtgtgg agacaggggc ttttatttca acaagcccac agggtatggc     240
tccagcagtc ggagggcgcc tcagacaggc atcgtggatg agtgctgctt ccggagctgt     300
gatctaagga ggctggagat gtattgcgca cccctcaagc ctgccaagtc agctcgctct     360
gtccgtgccc agcgccacac cgacatgccc aagacccaga ag                        402
```

```
<210> SEQ ID NO 2
<211> LENGTH: 1505
<212> TYPE: DNA
<213> ORGANISM: Homo sapiens

<400> SEQUENCE: 2
gtaagcccac ctgggtggga tccagccatc ctcaagtggt ctctctcttg tgcatgtggg      60
tgggccaagc agaaatcctg ccccatagtc tcctggctta caagtcagaa aagctccttt     120
gcaccaaagg gatggattac atccccatct ctttggtcac tctgcattgc aaatttcccc     180
tcccaccgct atggacgatg tgatgattgg aagatgttac aaaacagtgg ctaaacaaac     240
atgggctttg gtgtcagaca aaagtgaagt cctggctttc tcacacacca gcttagagcc     300
cttggcaaat aatgtgatgt acccaagcct cagtttcatc agtaacattg ggataataat     360
aatatctacc acatcagttt gttgtcaaaa ttaagtagct catgcatata ctttgagatg     420
cttttcacat gcctgcataa agtaattgtt ggaccatcgt taatgtctgc cataattgca     480
cttaataaca aagcttgtaa cctttcaagt tctgagattc tacaatcttc caagaaaat      540
aaaaggctaa tgggaactat tcaaaattca tattcagtag caagcataat taaacatgaa     600
acattaaaaa tagaaatttc tgtttggcta taagaatgcc tagacatttg taatgatcaa     660
aatctgcagg catcattttc taagagctag actgtaaaca aacctcagag gtaccaacta     720
tgccatcagt agtacataaa acatctgatg cacatttagt cacttgatcg atttctcttg     780
aatgagtgaa cgaatgaaca atgaatata agagattaaa attttagcca ttaagtagaa     840
agaataagaa ctaaagagaa ggtaaaggag gaaaagaga aggcaaggaa gttgagtaag     900
ggaagaaata gctctcgttt aagtattttg gggactctgt tgaaaaaga aatgccaaca     960
tgtggtttta atctttggag ctagaactaa taatattgtg caaaagcaca agatgagaga    1020
tcaagaagtt caccatgaca ccttcgctgc ttcctggtct taaacctcag ctgaggctgg    1080
aagaggacca tggtggctta ttggagatgt gaccccaggg agccctctg aaggatggaa    1140
ggggactggg caagacccaa cacacacaga acacagtagc cactggccag gcaggaagca    1200
aggatctcag aaaagacttt taggtgaatg tggcaggaaa gcgtgcttgc tgggcaaag    1260
gcagattcat tctttctctt cccaggtgac ccagcgcctc ttggtttcta actggggagg    1320
gggtaggtgt caagagatga gtcccaaagt tctggaatgg tgggtcttgt gactgaggtc    1380
tagacccctc tccagcatga gtgctgtctc ctgcatcata tggagcctgg gcattctgag    1440
ctcattcaaa gggacaccat gggaaccact tgttctcaat gcaattattt ttgtgatgtt    1500
tacag                                                                 1505

<210> SEQ ID NO 3
<211> LENGTH: 75
<212> TYPE: DNA
<213> ORGANISM: Homo sapiens

<400> SEQUENCE: 3
tatcagcccc catctaccaa caagaacacg aagtctcaga gaaggaaagg aagtacattt      60
gaagaacgca agtag                                                       75

<210> SEQ ID NO 4
<211> LENGTH: 15250
<212> TYPE: DNA
<213> ORGANISM: Homo sapiens

<400> SEQUENCE: 4
```

```
aggacaggag gattaaacag acagaggcaa ggatgatgag agaggagcag acagcaagaa    60
tgaaaagcag aaaatacaat agaggaaatg aagaaaagta ggcctgctgg agctagatga   120
tgatgtgatg gaaatagaag taacctttta gagaatctcg ctaagaaaca tggagaaaac   180
ggaaaagaaa aatgtaatgc cctagaaagc gcaaagaaag acagtggcaa aaatgaaaaa   240
aaaaaataaa aattataaaa gaggcaaaaa aagacacact attctctgcc tctaaaacac   300
aattaaataa aagaatttaa ataaaaatta aggcttctat atgcattttt aaattttgta   360
tgaatctgtt atggaagaat tgcctatgtc aatatatgtt cagagttaaa tattagcccc   420
aaatgctcag caagactgaa ttgtgtcata gaagttccca gattcccttt tcccgcaatg   480
tcattggagg ctgcatttct tagtcaagtc cagggtttag gccaagggc atccggtatt   540 gcctaaaacc ctgtgaggtc tgtgaggtaa cttttgagaa gaggtcactg cactcttcat   600
cttttttgca ctttggaatc agatataaaa gatgtataag tttgctaggg ctgccataac   660
aaagtatcat aggctaggta gtttaaacca cagaaattga ttttttcata gttctgggag   720
ttgaaagtcc aaaatcaaag tatcagccct tgcaagggcc ttagagaagg ctctgtcatg   780
ggctcctccc ctcggcttgt aggtggcctc cttcttctcc ccctgtgtct tcacttcatc   840
ttccctccat acatatctct gtgtctaaac atcctctgtg tgaaacaaca ccagccaggt   900
tggatttggg cccaccccac tgacctcatt ttaacttaat tatctctgta aagactctgt   960
ctccaaatac agtcatattt tgacgtactg ggagttaggg cttcaacaca tgaatttgga  1020
cacaattcag ccagtgacag aagacttctg atctctgatg ataaccactg cattttgatt  1080
acagctccta gaaaacactc ccctccacca ccccaccaca gatctatttt tatatctgaa  1140
accctgagtt tctgctccat gagaaccccca ggaacatact atgttagatc tggaagaagc  1200
ctcagaaatc cccttatttt gaagactagg acactgagat ccagaagtgg gtaaagatgt  1260
gcttgggttc taagctgctc ttcttttggc caggagacaa cagcacataa tcaaagtggg  1320
tcaactaaga aagaattcca gaaggaaaag agagggcaga aatgaaggga gagaatgaga  1380
gcaaaagtgc tggatttccc tgagggtgaa gaaaagttaa atagaatcac agaattcaga  1440
ttttagagat cttctccttc agatcccttg gtttaatcag taggattggg gtcttcatag  1500
ataataaagc aaaaactctc gccatcctcc aagttgtgaa ttagaagagc tgagaaaggg  1560 tacaagacgaa agttctcta ccaaacaaat ggtgacattt tggggtaaga atatgactaa  1620
cccagaagtg aagcatttca tccaagtagt ctattttgaa gatgtcatgg tataaaggaa  1680
cctcctttct gcctggtcct ccatgcctct gccatgcttt ttactccagg atcacccttt  1740
ctagtggttc actgaaaacc caggattact taaatatgat ggacatgttc acggctcaat  1800
ccaggaggaa aaggtcgaac tgaaagcatg ccaaagcccc acatgggagc caagccactg  1860
ctgctgtggt tgcaaagtgg atcctggctt atcagagcag agagaagcca ggctcgtgcc  1920
ttagcccaag tggccagtca ccttattcag gagatactaa gttctccagc taagacatcc  1980
atgctttggg accagctgca gacagaagcc aattcctact acaaccatca ccttagagta  2040
gcatatagac acagatggct cttcaaagga ccacagttcc atggaataac taagaattca  2100
tgtcctgtgg aaaggtttga ataaactata attatatccca atcataaatt tcattcaaga  2160
agaactaaag caaaggcaaa gacagagaga agaaggaagg aaggagggag ggagggaggg  2220
aaggaaggaa ggaaggaagg aaggaaggaa ggaaggaagg aaggaaggaa ggaaaggaa  2280 ggaagaacaa aaagacttc tagttaaaga atgcttaact agcaaactat gtactataag  2340
acagttcttt tcggaatgag ttttatcaac tctaaagcaa ttatcttgaa tgcctacatg  2400
```

```
tgattactga ataatatgaa ccaagaaaac agaaagaatc tatattatct ttccatttcc    2460
ttctttccag tatcaatacc caagcctcta gtgatacatg gcatataatg ttggatggat    2520
ggatggatgg atggatggat ggatggatgg atggatggat gaatggatgg ttggatggac    2580
aaatgagtaa cataggctga tgaatagtgg tagaaagaca caccataaaa acaagtggca    2640
cttctgagat gaaatgattc ctattctcct acacaagaca gtgaggcaag tacagagtaa    2700
aaaaggaaag gcataggagc tatgcttata caagtattgt atgtttggaa tttccttcgc    2760
tggccaaatt gaaattgttc aaggacctat tgctacaggt ggcaactggc taagaatttc    2820
atagtgaata ttatacacct attactcccc ttaatgtttc tttgaagtaa gcagaatatt    2880
aataatcatt taaaattcca gtgtttcaac ttcaattgtt tcctagggca aattgataat    2940
tgtgtgtaaa actaattgga atatgtatgg aataatcatc ctgaaataaa attggtgaaa    3000
agtatttgtt attgggcatc tacaatgtgc aaacctctgt actaggcatg aacaagagtt    3060
ataagcattg gagaggctaa aatatagtcc ttaaggctgg gcacagtggc tcatgcctgt    3120
aatcctagca ctttgggagg ccaaggcggg cagattgcct gagctcagga gttcaagacc    3180
agcctgggca acatagcgaa accccatctc tactaaaaat acaaaaaaat tacctgggca    3240
tggtggcacg cacctgtaat cccagctact caggaggctg aggcatgaga attccttgaa    3300
cctgggaggc agaggttgca gcgagccgag atcctgccgc tgcatcccag cttgggtgac    3360
agagtgagac tctgtctcaa aaaaaaatta ataataaat aaatagtaaa atacagtcat    3420
taagagtaca aaatgtagat tcagactacc tgggttcaaa tcttggctct tacttgcatt    3480
gtggctttgg gcagatcatg taacttatgt gtgcctcagt ttcctcatct gttaaatagg    3540
ggcaacaact gaatctacct tattcagttg ttgtgagggt ttattgagat tgtgtgtgtg    3600
tatgtgtgtg agtgtagtgt gtgcatgtgt gtgtctgtgc aaggagtggg aggtgtatat    3660
tcagagacac atattacagc acttaaaatg gtatctagca cttagtaagc attattcaag    3720
ttttagttaa cattatttta cttacctctg aaaattggag ctatgtgaaa aagaagttgg    3780
tctcctgaag tagaagccag tcttgtgtca ccaaaaactt caagcccaag cttgccaacg    3840
cttttccatg atgtggtagt agagtttcaa gcatgtggta ggataagaga actcaatgac    3900
ctaagaacca ttccaaccca gagaacccct ggttctatga ataattccaa cttaaatagg    3960
tagcttggct ctcccaagtg agagccattg cttctgtttc cgggtcatat aatgaacttt    4020
cagaaaacca ccattttttct caaccagtta aaattaagtg taatacgtgc tttcatttca    4080
tggtgcctgg ggaaaattta attgtagtat gaactccagt tattggtagt cttaagtaaa    4140
attgccaaaa taaatagaaa tgcaggatat ttctgggctc acacagcttc cgggacactt    4200
tagtttcttg ggctgccaat ccagtgcctt tcacaagcat ttgatctttt ttcaaacatc    4260
tcttgaaaac aaacaaaacc tcacacagct tctaatgtgt gcactgttcg aatgtaaggg    4320
tggaaaagga ggcaaagaaa tgagctccca aagagcaatt ccccttctct cgcctccatc    4380
ccttgacgac ctccctccca ctaaagggaa acattgtttt cttaggtaat aaattctgca    4440
atttctcaag tccattaaca tccactgggc aagatgagat ctattctttt tatttgccca    4500
taggaaaaga atagtgcttt tttgcaatat tcactagata acacagagtt gacttttaat    4560
ccaagggcaa cattgatagt ctctagttaa aggggaagcc ttcaggagca atgaaaagat    4620
taatagtttt agatgaagca gaatccaaat ccctttttat gagttttgaa atatccagtt    4680
tgtatgctca cctcaatact taaagcccag ttactgattc ctttggccta agcaagacag    4740
```

```
gtcaatttttt aaagagggag tagctgaggt tagcaaaaat tctccaggtc cacaaaactt    4800
ccagacctgc aaggtgaaaa tcagcttttc tgtcatccct aaaggcctaa ctggaatcag    4860
aactttcccc tgatgcccac atatttggag gtccttttt aatgggactc cttaatgcct    4920
ttagtgccat cccatttca tccagtgtcc aaaagaaatg atttaaaaat ataaacgtat    4980
gtttaaattc cagaagagag aaatggagat tgagaacaat agggaaatga tgagagctat    5040
gggaaaagag gtttatgagt ccatgtctga ttcttccaga gagcccctaa gaaagttctt    5100
atcataccag gaactcaatt ataactttca ttgcctattg ttagatgagt aacaggagct    5160
agaaaacatt ttggaaattc ccatctttat tttttaact aatatgatta tagttttaag    5220
aaccattggt caagaagcta acttttaaaa aagtggaagt atgatggtta gaaataagaa    5280
tgctaaaggt gcatcaagct gattttaatt ctaaatgtcc ttggcagcaa tttagaatct    5340
gtaataaact acaccaaaca gttttgaggg gaaggggatt agtttctccc cttccttcgt    5400
gtgtgtgtgt gcgcgtgtgt gtgtgtgcac ctttgtgttc tagcattgtt gcacccatta    5460
cagagctggg gggaactatt ttccaaaatt ataggtgaga acagtttctt ggattgtctt    5520
tcagtgaagg taaattcctc tgtaaaaact aaccatcatt cagtaaaaac tgcaggattc    5580 cttttgtcttc tcaaaagcct gttctcatc ctaaattaaa aattattcag gaaatagaga    5640
ggacattatt ggagggggtgg aaataagttg gttttctttt tattgtatct tttgaggatc    5700
cagggacttc taccatttcc catctaacat acagagaagg attctctagg tccctgtcta    5760
tagactgcag taactttcct atagaaccaa tttgcaattt tagaaatttc taggtctaat    5820
tattgaccca ttacaaccaa aggtcaatgc atccagccaa tcttccttct atcatcccct    5880
gcccttactt ctattaggga ctgggattac aggcaaaacc catcaaatgc ctcttctacc    5940
actttcccat ttcttaacca ttagcctcta acttcctcta ttcagtttct catatgcttt    6000
catgcccatt gggtcagata aaggaacatt catttatttg agtaggcatc tgttatgatc    6060
actccggaaa aaagatgaca atgggttacc ttgtcctcct gggcttctct aactgacatg    6120
gtcaaaatgc ccatatgaag ataagatgtt aagagcaaga tttatgaaaa gctgagtatg    6180
atggcagctc ttgtctcata aaataactcg aaagttccca gtgaaagacc aagaaatttt    6240
acatcaaacc caaaccggcc aaatggtcca agcttccaag ctgggatcca tggctaaagt    6300
ttctacaaaa ttctgggtac aatgtataaa cattcacttg gggctttctg tctagccagc    6360
accaagaggt caagtaatca aggaccaact agccctgcca tctgtgaaaa tatgtgctat    6420
tttcacggct ttagttcaca attatggcaa gacaaaagtt ccaaataatt aggagcaaga    6480
ccatggcagg ttgacggttg agtaaggttc tcaatcagcc gacaattgta gagttgggga    6540
tgtgcaatgt ttatgtcatg gtgtaagtat gtggcatgct tgactagctt gtgaggcact    6600
ggaagactag aaggaatgaa aaatatgaat gaatcaataa atgcatagta taattactgt    6660
tattttgtca gtattgtttt acctaggtca ctattgaatg ctctgatttg tctctttata    6720
aataataata tgttttcttc ttcaaaagaa cactaggatg aaggtagagg tgcttttggc    6780
acaatgccac aattctgatt tttttaaaac tgtatgcatg cataaaatgt tcttgagcca    6840
ttctctgcct tggaatagca ctggctggca ttctgcatgt ttacttttat atgctgaagg    6900
cccccatcaa cctcaaacag aggcaaatca atttaacttc tcatagtgtt attttgttca    6960
tcctaaaagt tcaagagagc cttccaaact tccaaaattt ctctcaattc agtgaggagg    7020
aaaattcaga acacagcatt tgaatgttct gcccagattt gtcacacaca caaggaatga    7080
gtgaaagagg gcaacaccct ttcctcctaa ccctgtgaac tcatcactat tgcattgaaa    7140
```

```
tgacaccaaa aggtaaaaac cctaggcctc acatctccca agaacactgc aataggagtt    7200
actgcataca ccagtttaag taactctagc ataaattgta tgtcagatga aacaatggca    7260
ttttggaggc ttaagagaaa aagaataatc aaatccagtt tttaggtact aatgtgctga    7320
atctttagca catagcagca aaattgctag aatctggtgt ttcactttt aaaataccac     7380 atttgaacct ttcagcaatt ccaaaatcaa ctccctctgc gaaagataat aagcttaaac    7440
attttttaaa tttaaaaatg taacacaaac aaacagctaa gcaaacaagc tgcccataaa    7500
atcaacagtc tggggagccc tgatcctgaa gtattttaca acatccttca tgactattaa    7560
aggcaacata aacacctctt gtcagcaagg gaaactaccc ttggcatttt tttttctttg    7620
ttccccaggc ttttaaacca ttttgataga gattttttac atcacaggca gaaatatttg    7680
aaatagagtc aggtggtagt ctttaaaaga gtaagaaagt tgctaagtca agataatctt    7740
ggaataaagt cctctgattc ctggggattc ctagggatgc cccagtcact agaaaacaga    7800
gctgtaagtc cactctccca gcactcaacg gagctccgga aaccaaggag ctagctactg    7860
tttccccaca ttcagccaga gaaagggcag cactctagca tgcaaactgc tttgacaata    7920
gtaacaatta aaagtaaat taaaagaat cataatagct gatattgatt aggtacttgc      7980
cctgtggcaa gagctatagg gaatcacctc atttaatctt cacatgaagc ttgcagagtg    8040
agtaccacaa ttatcactat tgtatagaca ggaaaactca ggctgagtat ggctaagtgt    8100
cttgccaacg tcttgggcta acaagcggtc aagcagaatc caaacccgag atagatagac    8160
cacagtgtgc taatcaagca ctgcactctc tcctgcattt cttagttgat atttaccata    8220
tacaatctgt cacttgtatg agatggcagg gggttctgtg ctatttgtcc ttgtagagaa    8280
taccacagga agaaagtaag cagccatgca atatttgctg ttgacctgaa ctccattcca    8340
tcattcctgc aggaaattcg catccattaa atgagcattt cctggtttgc cactttgctc    8400
aaacactttg cttggatctg gagaggatat agaagtgaag gaaatatgct acctgctctc    8460
aaggaactta tgttttagtg gagagacaaa catgcagaat ttactctaca gaacatcaat    8520
gcttgagcaa atgtagaccc agagagggct cttacagcac acaagccaga acagactgat    8580
ggtgctaaca attaggttca aggttttct aaacagtaga ctctcctgca tacaactata    8640
ccgcatgcca ggtaaatgac tgagggttat tacatccaat tataacacca ctgtgatgta    8700
ggtgctctta ccccacactt tcattttaca gaagaggaaa ttgaggacag cacaatgtag    8760
tgattatcaa aggtcacacg actactgtgt gggagagcta ggatttaaac cagatgcata    8820
agatgaggtc ctccaagaaa cagaagatga gaaggtgtta aatgagcagg ggttttatta    8880
gggggaatta atgtgtgaac agaaataggg gaggataggc aaagccatca gattgcaagg    8940
caagcctaac cccaagggaa ggagagagag agagtagatt ggttggaaac atttttggtg    9000
ggtctatggt ctaaggaaag ttcagcaaag tcatcatgga gttttgagc caaagttggg     9060 caatacagtt gcccaacaaa tttctgtgtt tctcagaaat aggtctgcct caatgtcccc    9120
accatacttg gtcactggct cttgggaggg gcctgccctg ttccaatcca ctagagccaa    9180
agaagagccg ttgtactggc aggggtggg ggaattccta caaccacata aaaagtgggg    9240
tgaggtttcc agaaaaaaac gtgatgctgg gctaaccaaa actgtgtcca gtaagtacat    9300
atccctcact ctgttaaaga agcagccaca taaacaagga gtacacgttt ctcaaaatgt    9360
gcaccttgtt ctttggtttt gaagtcacat cccaaagtgc tgagtagatc gcatgaccct    9420
cgctttgcct ggctgccaga gaggaaaggc tgatccaact ctcctggaat ttgaacttgt    9480
```

```
gattccctga agtaaagaga tatcaaagtt gatactgaga catctaaatc atcctccacc    9540
atttcacatg tccccaggcc aagccagcaa aattgctata gcacatccct ttcaacaggt    9600
aaagggctga tatctgagcc ctcttccaa tcatccactg ctcttttctt ctcatttgc      9660
ccttttggg  agcaggtcaa tgctgagtta gtactttatg ctgtacaata agctgctgat    9720
attccatgct ggacagaatt tcccagtat  tttttataga gtgccaggct tttcctagac    9780
ttcatgtcat acaatactta acttgtttgg agtgggtgga gatggaaaca tagtctattg    9840
aaaacatcac tgcttcctcc ctgaagttta aagagcctat ttttatcctt ttagattcta    9900
tctctcaggc aaaatctcat aaagataagt ggggaggaaa aaaggggggt tataataccct   9960
agggagtttg cttttgctaa ttgaatactg tgctcctaga cttctataaa taccattaca   10020
aatgggtccc agcttgtggt aatactcacc ctcctcattg agtcttctgt cccatggcac   10080
agcctttccc tccaaactag catctacccc catctggaag catgggcagc tcatgatatt   10140
atcaactatt gctattggaa agtgatttgg acttgaaagc actagatatt ttttacctct   10200
tgggaggca  gtttagcaga gtggttaact ggtgagctcc agaatcagaa ggaataggtc    10260
caaattccaa ccactattac atctccatca taagaaatta ggcaagttgt ttatcctaag   10320
tttcagattc cttaaagata aaacagtcaa gacagtagta cttatccctg agagaagtat   10380
aggaaacaag aaaatatatg caatttacat acatactaca atccccagca catgacaaat   10440
gttcaagtaa tgggaactgt tattatttta gcccttgtc  tatcagtttg ttcctctgtg   10500
acctcaagca cattactaaa tgttagcgag cttcagcttg tacgtgggac tgacaggaat   10560
aacaccgcat cacctcatgt ggtgattgta aggattcagt gatattattt tgtaaactgt   10620
aaagcctttg caaatgttaa gcaagattat tattattgcc gttgttatta gtcctcagtg   10680
atctttttt  tttttttttt tttttttttt tttttttttt ttggagacag agttttactc    10740
tgtcgccaag gctggaatgc agtggcacaa tctcagctca ctgcaacctc cgcctcctgg   10800
gttcaagcaa ttttcctgcc tcagcctcct gagtagctga aactacaggc acacgccacc   10860
acaccaggct aatttttgt  attttagta gagacggggt ttcaccatgt tggccaggct   10920
ggtctccagc tcctgacctc aagtgatctg cccacctcgg cctcccaaag tgctgggatt   10980
acaggtgtga gccaccacac ctggcacagt aatcttaatt gaaaagtctg tggatagctt   11040
tccaaaggaa agcttggagc ttggataaga accaagagat aatgggagaa ggtgaatggc   11100
ctcttcaggg cctttttctag caccctaaat atgcgtgtct gtccataatg ggtaatcata   11160
tatatcacaa atcaaaccct ccacaaactt atttcctaat gtgtttgtta acctttcctt   11220
ctaaagggta aacttcttta accaaccccca gtgagctgga ggatcaatgt tttcttaata   11280
gtcttacctt cgttggtgtc aataggaaac agtatttact cactactgtt ttcctttaa    11340
aaatctgtct agttgcatac tagaaacagt ttcagctggt ttgtttgtat tggacaagct   11400
gctgaagtga aaagttttg  cttgactgaa tgtgagacag tttcataact cttcaagaag   11460
tgcaccaaag gtgggtgcca gctctgatga cggctgcttc taacatgcct ccacttgccg   11520
cccattgtca agggtggctg gcgtaattaa gttaagacaa tgagcaaagc aacagatgca   11580
actgagacct agtccctgag tgcttttgtt ttgtcactgt cattgtctgc aacaaagaag   11640
tcacatgtga cagcctggga agagagccaa atgcaaacca gacgatatcc cagctggttt   11700
gaatggcctc caccgtgcac gtgtgtgcat gggaatcatg ctacttggta cagcatctgc   11760
ttcactcaag tgagtttcag cccatggctt tgctgtgatg ctgagacaga cccagaagaa   11820
acagaccagg gaatccctcc gctcagactt tacactttat accttgtgct ttgagagaaa   11880
```

```
agaaaaagaa tctctctatt ggagacaaaa aataggatgt atgtggttgg tcaatctaac    11940
ctcaattctt tttgctatag ccccccgcta atttaaagag tgaagcatag atggtatctt    12000
aatgttttct tgtagaaatt tgggattaat ttggcttgag aggaagaatg gagattaaac    12060
gctttatgag gctttctttt aatttgttcc catttcattc ctgaatattt tcttagtttg    12120
ggcattgcag atgtttaaag aacttcttat tttgagctgg tatgcctctt aaacagaaaa    12180
acaaaaggta aaattcaaat tagtgtgttt ctccgcctgt taattaattt ggttagtagt    12240
taggcagaga gatggcatcc ttaataatat ctattttgcg ggtttgatca gctacagacc    12300
atcaacagtg ttgattgaga attgaacaaa aacatttcaa ggagtttggg aacattaggg    12360
atgctattct gtggccccat gtgtccttct ctcattttc tagagaactc ctataagaaa    12420
gcagaacacg gccaggcatg atggctcatg cctgtaatcc cagcacttca ggaggctgag    12480
gcaggcagat cacctgaggt caggagttca agaccagcct ggccaacatg gtgaaaccct    12540
atctctatta aaaatacaaa aaattagctg gcatgatgg cgcgtgcctg taatcccagc    12600
tacttgggag gctgaggcag gagaatcact tgaactggga ggcaaaggtt gcagtgagcc    12660
tagatcacac cactgcactc cagcctgggt gacagagtga gactccaact caaaaaaaag    12720
aaagaaagaa agaaagaaag cagaacccaa tggaagatta agaacacaca tttagcttac    12780
gcctgtaata ccagcacttt gggaggccaa ggcgggtgga tcacaaggtc agaagttcga    12840
gaccaacctg gccaatatgg tgaaacccca tctctactaa aaagtacaaa aattagccat    12900
gcatggtggc aggcgtctgt aatcccagct actacagagg ctgaggcagg agaatcactt    12960
gaacccggga ggcagaggtt gcagtgagct gagaacgcgc cactgcactc cagcctgggt    13020
gacagagcga gactccatct caaaaaaaaa aaacaacaaa aaaaaacaaa acacaagttt    13080
actgggaact tagcagtaga tgctttgcac cacaacaaat gtatcttaag tggtcttttg    13140
tgatatttga gggaaagtgc cagaatttaa aacaaatggc atttcaagtt attctataca    13200
aatgcccagt ttcttctac catctttttt tccttttgc agtggtcact gagctatttt    13260
agtgaatgtt tttacacaat gatgccatct tccttctact cagtcagtac aagatgttga    13320
ccatcgactc ataaaacact agctaccttt catgaaggac ttggtgataa ctctcatgtt    13380
ccaagtagaa ccggaaaaca tgtgtaagaa aacctgccga tccctatggg ccttggccaa    13440
taggtattat tcccaagggg tggcagttta tcttttccc cagccttcat attaaaacct    13500
ctcaccttct ccaggtctca ggtctgtgta atctcaaatg tgctttagct cctcacaata    13560
ttgtaactgt gtgggtgttc attaccttag ccagaagaca gtttacagat tccaggtctc    13620
atggagagaa cttttgtttt tggttatgaa cctcactgta taccaataat tatccattac    13680
atccttctgt agagggctct ctggctagag ataaaaccaa aaaaagaagt acctcaggtt    13740
tatgcatata aatgccagtt cctccttgat tttatttcaa aactcctgtc tacatacttt    13800
gcaatttaaa tacattcaag gataaagtaa taactgtagg aaaagtatta taatataatg    13860
acttagttct gcacatcaca aggggtccc tcatactcat tcattcattt cactcatttt    13920
acagatattt attgagcacc tgcaataacc tgcacactgc tctagacact gggactataa    13980
cagtaaacag acagatacat ctctggtctc acagggcttc tattctaagc aaaactcaat    14040
atccaggccg ggtgcagtgg ctcatgcctg gaatgccagc actttgggag accaaggcca    14100
ggcagatcac ctgagcccac tagttgaaga ccagcctggg caatatagca aaacccgtc    14160 tctacaaaaa aaaaaaaaaa aaaaaaaaa aaattgtcaa ggcatggtgg catgcgcctg    14220
```

| | |
|---|---|
| tggtcccagc tacttaggag gctgaggcag gaggattgtg taagcctggg aggcagaggt | 14280 |
| tgcagtgacc tgagatggca ccaccacact ccagcctggg caacagagtg agaccctgtc | 14340 |
| caaaaaaaaa aaaccctcac tatccttaag ataacatcat tgcttgttga tgagtgaatg | 14400 |
| ttaacaccaa attaggaacc caggactttt agtcttggca tggttacttt ccaataaaga | 14460 |
| tgacaatact aagaagagaa aaatgattta ataatgataa tagtggctaa tacttatgta | 14520 |
| gtgcttacca tgtgccaggt ctattgtaag tactttata tatattaatt atttaatctt | 14580 |
| tgatcctata aggtagatat tattgttacc ctagtttata gatgaagaaa cggaaacaca | 14640 |
| agagattgcc actcatacaa gtttacacag ccagaaaata gaaaagctac gagttgagct | 14700 |
| cagcccagta tgtctatgat tttacagact caaaattaat tataagattt cctaatcttc | 14760 |
| gatttctgaa actctgcctt gctctagagg aaaacaagaa aaacaatgaa aaataaatgt | 14820 |
| ctcttttta caaaaattaa aacagaacaa actgcaataa aacaacagag gatgaatcca | 14880 |
| gaatgtgatt gatttttttt cttactagga aaggatctag aggccagaag gctggatttt | 14940 |
| tcaggatctc ctttcaatca atgaatctgt gatagaagca gatgaatcaa atctcatctt | 15000 |
| tgtgtgatta taaagctgtc tgtggtattc acgccaccag gggtacatag aagatgcctg | 15060 |
| agtgaggttt ggcaaaagta ctaagggcct gtccacctat acatgccctt ctcaggaaaa | 15120 |
| ccaaggttca agctctctat tagctcaact ggtaaggcgt aagacatgga aggttgaggc | 15180 |
| ccaatgttag aaatagatgg atacataaaa cttcatcaag ttaatgtcac tttttctcct | 15240 |
| ttatttatag | 15250 |

<210> SEQ ID NO 5
<211> LENGTH: 60
<212> TYPE: DNA
<213> ORGANISM: Homo sapiens

<400> SEQUENCE: 5

| | |
|---|---|
| gaagtacatt tgaagaacgc aagtagaggg agtgcaggaa acaagaacta caggatgtag | 60 |

<210> SEQ ID NO 6
<211> LENGTH: 375
<212> TYPE: DNA
<213> ORGANISM: Homo sapiens

<400> SEQUENCE: 6

| | |
|---|---|
| gtaagcccac ctgggtggga tccagccatc ctcaagtggt ctctctcttg tgcatgtggg | 60 |
| tgggccaagc agaaatcctg ccccatagtc tcctggctta caagtcagaa aagctccttt | 120 |
| gcaccaaagg gatggattac atccccatct ctttggtcac tctgcattgc aaatttcccc | 180 |
| tcccaccgct atggacgatg tgatgattgg aagatgttac aaaacagtgg ctaaacaaac | 240 |
| atgggctttg gtgtcagaca aaagtgaagt cctggctttc tcacacacca gcttagagag | 300 |
| aaaagacttt taggtgaatg tggcaggaaa gcgtgcttgc tggggcaaag gcagattcat | 360 |
| tctttctctt cccag | 375 |

<210> SEQ ID NO 7
<211> LENGTH: 300
<212> TYPE: DNA
<213> ORGANISM: Homo sapiens

<400> SEQUENCE: 7

| | |
|---|---|
| gtaagcccac ctgggtggga tccagccatc ctcaagtggt ctctctcttg tgcatgtggg | 60 |
| tgggccaagc agaaatcctg ccccatagtc tcctggctta caagtcagaa aagctccttt | 120 |

| | |
|---|---|
| gcaccaaagg gatggattac atccccatct ctttgctaaa caaacatggg ctttggtgtc | 180 |
| agacaaaagt gaagtcctgg ctttctcaca caccagctta gagagaaaag acttttaggt | 240 |
| gaatgtggca ggaaagcgtg cttgctgggg caaaggcaga ttcattcttt ctcttcccag | 300 |

<210> SEQ ID NO 8
<211> LENGTH: 21
<212> TYPE: DNA
<213> ORGANISM: Homo sapiens

<400> SEQUENCE: 8

| | |
|---|---|
| cttttctcc tttatttata g | 21 |

<210> SEQ ID NO 9
<211> LENGTH: 933
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9

| | |
|---|---|
| atgggaaaaa tcagcagtct tccaacccaa ttatttaagt gctgcttttg tgatttcttg | 60 |
| aaggtgaaga tgcacaccat gtcctcctcg catctcttct acctggcgct gtgcctgctc | 120 |
| accttcacca gctctgccac ggctggaccg gagacgctct gcggggctga gctggtggat | 180 |
| gctcttcagt tcgtgtgtgg agacaggggc ttttatttca acaagcccac agggtatggc | 240 |
| tccagcagtc ggagggcgcc tcagacaggc atcgtggatg agtgctgctt ccggagctgt | 300 |
| gatctaagga ggctggagat gtattgcgca cccctcaagc ctgccaagtc agctcgctct | 360 |
| gtccgtgccc agcgccacac cgacatgccc aagacccaga aggtaagccc acctgggtgg | 420 |
| gatccagcca tcctcaagtg gtctctctct tgtgcatgtg ggtgggccaa gcagaaatcc | 480 |
| tgccccatag tctcctggct tacaagtcag aaaagctcct ttgcaccaaa gggatggatt | 540 |
| acatccccat ctctttggtc actctgcatt gcaaatttcc cctcccaccg ctatggacga | 600 |
| tgtgatgatt ggaagatgtt acaaaacagt ggctaaacaa acatgggctt tggtgtcaga | 660 |
| caaaagtgaa gtcctggctt tctcacacac cagcttagag agaaaagact tttaggtgaa | 720 |
| tgtggcagga aagcgtgctt gctggggcaa aggcagattc attctttctc ttcccagtat | 780 |
| cagcccccat ctaccaacaa gaacacgaag tctcagagaa ggaaaggaag tacatttgaa | 840 |
| gaacgcaagt agcttttcct cctttatta taggaagtac atttgaagaa cgcaagtaga | 900 |
| gggagtgcag gaaacaagaa ctacaggatg tag | 933 |

<210> SEQ ID NO 10
<211> LENGTH: 858
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

| | |
|---|---|
| atgggaaaaa tcagcagtct tccaacccaa ttatttaagt gctgcttttg tgatttcttg | 60 |
| aaggtgaaga tgcacaccat gtcctcctcg catctcttct acctggcgct gtgcctgctc | 120 |
| accttcacca gctctgccac ggctggaccg gagacgctct gcggggctga gctggtggat | 180 |
| gctcttcagt tcgtgtgtgg agacaggggc ttttatttca acaagcccac agggtatggc | 240 |

-continued

| | |
|---|---|
| tccagcagtc ggagggcgcc tcagacaggc atcgtggatg agtgctgctt ccggagctgt | 300 |
| gatctaagga ggctggagat gtattgcgca cccctcaagc ctgccaagtc agctcgctct | 360 |
| gtccgtgccc agcgccacac cgacatgccc aagacccaga aggtaagccc acctgggtgg | 420 |
| gatccagcca tcctcaagtg gtctctctct tgtgcatgtg ggtgggccaa gcagaaatcc | 480 |
| tgccccatag tctcctggct tacaagtcag aaaagctcct ttgcaccaaa gggatggatt | 540 |
| acatccccat ctctttgcta acaaacatg gctttggtg tcagacaaaa gtgaagtcct | 600 |
| ggctttctca cacaccagct tagagagaaa agactttag gtgaatgtgg caggaaagcg | 660 |
| tgcttgctgg ggcaaaggca gattcattct ttctcttccc agtatcagcc cccatctacc | 720 |
| aacaagaaca cgaagtctca gagaaggaaa ggaagtacat ttgaagaacg caagtagctt | 780 |
| tttctccttt atttatagga agtacatttg aagaacgcaa gtagagggag tgcaggaaac | 840 |
| aagaactaca ggatgtag | 858 |

<210> SEQ ID NO 11

<400> SEQUENCE: 11

000

<210> SEQ ID NO 12

<400> SEQUENCE: 12

000

<210> SEQ ID NO 13

<400> SEQUENCE: 13

000

<210> SEQ ID NO 14
<211> LENGTH: 153
<212> TYPE: PRT
<213> ORGANISM: Homo sapiens

<400> SEQUENCE: 14

```
Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser His Leu
            20                  25                  30

Phe Tyr Leu Ala Leu Cys Leu Leu Thr Phe Thr Ser Ser Ala Thr Ala
        35                  40                  45

Gly Pro Glu Thr Leu Cys Gly Ala Glu Leu Val Asp Ala Leu Gln Phe
    50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Glu Val His Leu Lys Asn Ala Ser Arg Gly
    130                 135                 140

Ser Ala Gly Asn Lys Asn Tyr Arg Met
```

<210> SEQ ID NO 15
<211> LENGTH: 462
<212> TYPE: DNA
<213> ORGANISM: Homo sapiens

<400> SEQUENCE: 15

```
atgggaaaaa tcagcagtct tccaacccaa ttatttaagt gctgcttttg tgatttcttg      60
aaggtgaaga tgcacaccat gtcctcctcg catctcttct acctggcgct gtgcctgctc     120
accttcacca gctctgccac ggctggaccg gagacgctct gcggggctga gctggtggat     180
gctcttcagt tcgtgtgtgg agacaggggc ttttatttca acaagcccac agggtatggc     240
tccagcagtc ggagggcgcc tcagacaggc atcgtggatg agtgctgctt ccggagctgt     300
gatctaagga ggctggagat gtattgcgca cccctcaagc ctgccaagtc agctcgctct     360
gtccgtgccc agcgccacac cgacatgccc aagacccaga aggaagtaca tttgaagaac     420
gcaagtagag ggagtgcagg aaacaagaac tacaggatgt ag                        462
```

<210> SEQ ID NO 16
<211> LENGTH: 158
<212> TYPE: PRT
<213> ORGANISM: Homo sapiens

<400> SEQUENCE: 16

```
Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
        35                  40                  45

Gly Pro Glu Thr Leu Cys Gly Ala Glu Leu Val Asp Ala Leu Gln Phe
    50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Tyr Gln Pro Pro Ser Thr Asn Lys Asn Thr
    130                 135                 140

Lys Ser Gln Arg Arg Lys Gly Ser Thr Phe Glu Glu Arg Lys
145                 150                 155
```

<210> SEQ ID NO 17
<211> LENGTH: 477
<212> TYPE: DNA
<213> ORGANISM: Homo sapiens

<400> SEQUENCE: 17

```
atgggaaaaa tcagcagtct tccaacccaa ttatttaagt gctgcttttg tgatttcttg      60
aaggtgaaga tgcacaccat gtcctcctcg catctcttct acctggcgct gtgcctgctc     120
accttcacca gctctgccac ggctggaccg gagacgctct gcggggctga gctggtggat     180
gctcttcagt tcgtgtgtgg agacaggggc ttttatttca acaagcccac agggtatggc     240
```

```
tccagcagtc ggagggcgcc tcagacaggc atcgtggatg agtgctgctt ccggagctgt    300
gatctaagga ggctggagat gtattgcgca cccctcaagc ctgccaagtc agctcgctct    360
gtccgtgccc agcgccacac cgacatgccc aagacccaga agtatcagcc cccatctacc    420
aacaagaaca cgaagtctca gagaaggaaa ggaagtacat ttgaagaacg caagtag       477
```

<210> SEQ ID NO 18
<211> LENGTH: 137
<212> TYPE: PRT
<213> ORGANISM: Homo sapiens

<400> SEQUENCE: 18

```
Met Ile Thr Pro Thr Val Lys Met His Thr Met Ser Ser Ser His Leu
1               5                   10                  15

Phe Tyr Leu Ala Leu Cys Leu Leu Thr Phe Thr Ser Ser Ala Thr Ala
            20                  25                  30

Gly Pro Glu Thr Leu Cys Gly Ala Glu Leu Val Asp Ala Leu Gln Phe
        35                  40                  45

Val Cys Gly Asp Arg Gly Phe Tyr Phe Asn Lys Pro Thr Gly Tyr Gly
    50                  55                  60

Ser Ser Ser Arg Arg Ala Pro Gln Thr Gly Ile Val Asp Glu Cys Cys
65                  70                  75                  80

Phe Arg Ser Cys Asp Leu Arg Arg Leu Glu Met Tyr Cys Ala Pro Leu
                85                  90                  95

Lys Pro Ala Lys Ser Ala Arg Ser Val Arg Ala Gln Arg His Thr Asp
            100                 105                 110

Met Pro Lys Thr Gln Lys Glu Val His Leu Lys Asn Ala Ser Arg Gly
        115                 120                 125

Ser Ala Gly Asn Lys Asn Tyr Arg Met
    130                 135
```

<210> SEQ ID NO 19
<211> LENGTH: 414
<212> TYPE: DNA
<213> ORGANISM: Homo sapiens

<400> SEQUENCE: 19

```
atgattacac ctacagtgaa gatgcacacc atgtcctcct cgcatctctt ctacctggcg    60
ctgtgcctgc tcaccttcac cagctctgcc acggctggac cggagacgct ctgcggggct    120
gagctggtgg atgctcttca gttcgtgtgt ggagacaggg gcttttattt caacaagccc    180
acagggtatg gctccagcag tcggagggcg cctcagacag gcatcgtgga tgagtgctgc    240
ttccggagct gtgatctaag gaggctggag atgtattgcg cacccctcaa gcctgccaag    300
tcagctcgct ctgtccgtgc ccagcgccac accgacatgc ccaagaccca gaaggaagta    360
catttgaaga acgcaagtag agggagtgca ggaaacaaga actacaggat gtag          414
```

<210> SEQ ID NO 20
<211> LENGTH: 195
<212> TYPE: PRT
<213> ORGANISM: Homo sapiens

<400> SEQUENCE: 20

```
Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30
```

Phe Tyr Leu Ala Leu Cys Leu Leu Thr Phe Thr Ser Ser Ala Thr Ala
         35                  40                  45

Gly Pro Glu Thr Leu Cys Gly Ala Glu Leu Val Asp Ala Leu Gln Phe
     50                  55                  60

Val Cys Gly Asp Arg Gly Phe Tyr Phe Asn Lys Pro Thr Gly Tyr Gly
 65                  70                  75                  80

Ser Ser Ser Arg Arg Ala Pro Gln Thr Gly Ile Val Asp Glu Cys Cys
                 85                  90                  95

Phe Arg Ser Cys Asp Leu Arg Arg Leu Glu Met Tyr Cys Ala Pro Leu
             100                 105                 110

Lys Pro Ala Lys Ser Ala Arg Ser Val Arg Ala Gln His Thr Asp
         115                 120                 125

Met Pro Lys Thr Gln Lys Tyr Gln Pro Pro Ser Thr Asn Lys Asn Thr
     130                 135                 140

Lys Ser Gln Arg Arg Lys Gly Trp Pro Lys Thr His Pro Gly Gly Glu
145                 150                 155                 160

Gln Lys Glu Gly Thr Glu Ala Ser Leu Gln Ile Arg Gly Lys Lys
                 165                 170                 175

Glu Gln Arg Arg Glu Ile Gly Ser Arg Asn Ala Glu Cys Arg Gly Lys
             180                 185                 190

Lys Gly Lys
        195

<210> SEQ ID NO 21
<211> LENGTH: 588
<212> TYPE: DNA
<213> ORGANISM: Homo sapiens

<400> SEQUENCE: 21
atgggaaaaa tcagcagtct tccaacccaa ttatttaagt gctgcttttg tgatttcttg     60
aaggtgaaga tgcacaccat gtcctcctcg catctcttct acctggcgct gtgcctgctc    120
accttcacca gctctgccac ggctggaccg agacgctct gcggggctga gctggtggat    180
gctcttcagt tcgtgtgtgg agacaggggc ttttatttca acaagcccac agggtatggc    240
tccagcagtc ggagggcgcc tcagacaggc atcgtggatg agtgctgctt ccggagctgt    300
gatctaagga ggctggagat gtattgcgca cccctcaagc ctgccaagtc agctcgctct    360
gtccgtgccc agcgccacac cgacatgccc aagacccaga gtatcagcc ccatctacc    420 aacaagaaca cgaagtctca gagaaggaaa ggttggccaa agacacatcc aggaggggaa    480
cagaaggagg ggacagaagc aagtctgcag atcagaggaa agaagaaaga gcagaggagg    540
gagattggaa gtagaaatgc tgaatgcaga ggcaaaaaag gaaaatga                 588

<210> SEQ ID NO 22
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
agctggcaat tccggttcgc ttgctgcgtc agaccccgta                            40

<210> SEQ ID NO 23
<211> LENGTH: 40
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 23
tacggggtct gacgcagcaa gcgaaccgga attgccagct                            40

<210> SEQ ID NO 24
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ctaatccata acatggctct agacttaagg cagcggcaga                            40

<210> SEQ ID NO 25
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tctgccgctg ccttaagtct agagccatgt tatggattag                            40

<210> SEQ ID NO 26
<211> LENGTH: 3250
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
cagggtcgga acaggagagc gcacgaggga gcttccaggg ggaaacgcct ggtatcttta      60
tagtcctgtc gggtttcgcc acctctgact tgagcgtcga ttttgtgat gctcgtcagg      120 ggggcggagc ctatggaaaa acgccagcaa cgcggccttt ttacggttcc tggccttttg     180
ctggcctttt gctcacatgc gcgttgacat tgattattga ctagttatta atagtaatca     240
attacggggt cattagttca tagcccatat atggagttcc gcgttacata acttacggta     300
aatggcccgc ctggctgacc gcccaacgac ccccgcccat tgacgtcaat aatgacgtat     360
gttcccatag taacgccaat agggactttc cattgacgtc aatgggtgga gtatttacgg     420
taaactgccc acttggcagt acatcaagtg tatcatatgc caagtccgcc cctattgac     480 gtcaatgacg gtaaatggcc cgcctggcat tatgcccagt acatgacctt acgggacttt     540
cctacttggc agtacatcta cgtattagtc atcgctatta ccatggtgat gcggttttgg     600
cagtacacca atgggcgtgg atagcggttt gactcacggg gatttccaag tctccacccc     660
attgacgtca atgggagttt gttttggcac caaaatcaac gggactttcc aaaatgtcgt     720
aataaccccg ccccgttgac gcaaatgggc ggtaggcgtg tacggtggga ggtctatata     780
agcagagctc gtttagtgaa ccgtcagatc gcctggagac gccatccacg ctgttttgac     840
ctccatagaa gacaccggga ccgatccagc ctccgcggcc gggaacggtg cattggaacg     900
cggattcccc gtgccaagag tgacgtaagt accgcctata gactctatag gcacacccct     960
ttggctctta tgcatgctat actgttttg gcttggggcc tatacacccc gcttccctta     1020
```

```
tgctataggt gatggtatag cttagcctat aggtgtgggt tattgaccat tattgaccac    1080 tccctattg gtgacgatac tttccattac taatccataa catggctcta gacttaaggc     1140
agcggcagaa gaagatgtag gcagctgagt tgttgtattc tgataagagt cagaggtaac    1200
tcccgttgcg gtgctgttaa cggtggaggg cagtgtagtc tgagcagtac tcgttgctgc    1260
cgcgcgcgcc accagacata atagctgaca gactaacaga ctgttccttt ccatgggtct    1320
tttctgcagt caccgtcctt gacacgaagc ttatcgatgt cgacctcgag tctagagggc    1380
ccgtttaaac ccgctgatca gcctcgactg tgccttctag ttgccagcca tctgttgttt    1440
gcccctcccc cgtgccttcc ttgaccctgg aaggtgccac tcccactgtc ctttcctaat    1500
aaaatgagga aattgcatcg cattgtctga gtaggtgtca ttctattctg gggggtgggg    1560
tggggcagga cagcaagggg gaggattggg aagacaatag caggcatgct ggggagtcga    1620
aattcagaag aactcgtcaa gaaggcgata aaggcgatg cgctgcgaat cgggagcggc     1680
gataccgtaa agcacgagga agcggtcagc ccattcgccg ccaagctctt cagcaatatc    1740
acgggtagcc aacgctatgt cctgatagcg gtccgccaca cccagccggc cacagtcgat    1800
gaatccagaa aagcggccat tttccaccat gatattcggc aagcaggcat cgccatgggt    1860
cacgacgaga tcctcgccgt cgggcatgct cgccttgagc ctggcgaaca gttcggctgg    1920
cgcgagcccc tgatgctctt cgtccagatc atcctgatcg acaagaccgg cttccatccg    1980
agtacgtgct cgctcgatgc gatgtttcgc ttggtggtcg aatgggcagg tagccggatc    2040
aagcgtatgc agccgccgca ttgcatcagc catgatggat actttctcgg caggagcaag    2100
gtgagatgac aggagatcct gccccggcac ttcgcccaat agcagccagt cccttcccgc    2160
ttcagtgaca acgtcgagca cagctgcgca aggaacgccc gtcgtggcca gccacgatag    2220
ccgcgctgcc tcgtcttgca gttcattcag ggcaccggac aggtcggtct tgacaaaaag    2280
aaccgggcgc ccctgcgctg acagccggaa cacggcggca tcagagcagc cgattgtctg    2340
ttgtgcccag tcatagccga atagcctctc cacccaagcg gccggagaac ctgcgtgcaa    2400
tccatcttgt tcaatcatgc gaaacgatcc tcatcctgtc tcttgatcag atcttgatcc    2460
cctgcgccat cagatccttg gcggcaagaa agccatccag tttactttgc agggcttccc    2520
aaccttacca gagggcgccc cagctggcaa ttccggttcg cttgctgcgt cagacccgt    2580 agaaaagatc aaaggatctt cttgagatcc tttttttctg cgcgtaatct gctgcttgca    2640
aacaaaaaaa ccaccgctac cagcggtggt ttgtttgccg gatcaagagc taccaactct    2700
ttttccgaag gtaactggct tcagcagagc gcagatacca aatactgttc ttctagtgta    2760
gccgtagtta ggccaccact tcaagaactc tgtagcaccg cctacatacc tcgctctgct    2820
aatcctgtta ccagtggctg ctgccagtgg cgataagtcg tgtcttaccg ggttggactc    2880
aagacgatag ttaccggata aggcgcagcg gtcgggctga acggggggtt cgtgcacaca    2940
gcccagcttg gagcgaacga cctacaccga actgagatac ctacagcgtg agctatgaga    3000
aagcgccacg cttcccgaag ggagaaaggc ggacaggtat ccggtaagcg gcagggtcgg    3060
aacaggagag cgcacgaggg agcttccagg gggaaacgcc tggtatcttt atagtcctgt    3120
cgggtttcgc cacctctgac ttgagcgtcg attttttgtga tgctcgtcag ggggggcgag   3180
cctatggaaa aacgccagca acgcggcctt tttacggttc ctggccttt gctggccttt     3240 tgctcacatg                                                            3250
```

<210> SEQ ID NO 27

<211> LENGTH: 4108
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 27

| | | | | | |
|---|---|---|---|---|---|
| cagggtcgga | acaggagagc | gcacgaggga | gcttccaggg | ggaaacgcct | ggtatcttta | 60 |
| tagtcctgtc | gggtttcgcc | acctctgact | tgagcgtcga | ttttttgtgat | gctcgtcagg | 120 |
| ggggcggagc | ctatggaaaa | acgccagcaa | cgcggccttt | ttacggttcc | tggccttttg | 180 |
| ctggcctttt | gctcacatgc | gcgttgacat | tgattattga | ctagttatta | atagtaatca | 240 |
| attacggggt | cattagttca | tagcccatat | atggagttcc | gcgttacata | acttacggta | 300 |
| aatggcccgc | ctggctgacc | gcccaacgac | ccccgcccat | tgacgtcaat | aatgacgtat | 360 |
| gttcccatag | taacgccaat | agggactttc | cattgacgtc | aatgggtgga | gtatttacgg | 420 |
| taaactgccc | acttggcagt | acatcaagtg | tatcatatgc | caagtccgcc | cctattgac | 480 |
| gtcaatgacg | gtaaatggcc | cgcctggcat | tatgcccagt | acatgacctt | acgggacttt | 540 |
| cctacttggc | agtacatcta | cgtattagtc | atcgctatta | ccatggtgat | gcggttttgg | 600 |
| cagtacacca | atgggcgtgg | atagcggttt | gactcacggg | gatttccaag | tctccacccc | 660 |
| attgacgtca | atgggagttt | gttttggcac | caaaatcaac | gggactttcc | aaaatgtcgt | 720 |
| aataaccccg | ccccgttgac | gcaaatgggc | ggtaggcgtg | tacggtggga | ggtctatata | 780 |
| agcagagctc | gtttagtgaa | ccgtcagatc | gcctggagac | gccatccacg | ctgttttgac | 840 |
| ctccatagaa | gacaccggga | ccgatccagc | ctccgcggcc | gggaacggtg | cattggaacg | 900 |
| cggattcccc | gtgccaagag | tgacgtaagt | accgcctata | gactctatag | cacacccct | 960 |
| ttggctctta | tgcatgctat | actgtttttg | gcttggggcc | tatacacccc | cgcttcctta | 1020 |
| tgctataggt | gatggtatag | cttagcctat | aggtgtgggt | tattgaccat | tattgaccac | 1080 |
| tccccctattg | gtgacgatac | tttccattac | taatccataa | catggctcta | gacttaaggc | 1140 |
| agcggcagaa | gaagatgtag | gcagctgagt | tgttgtattc | tgataagagt | cagaggtaac | 1200 |
| tcccgttgcg | gtgctgttaa | cggtggaggg | cagtgtagtc | tgagcagtac | tcgttgctgc | 1260 |
| cgcgcgcgcc | accagacata | atagctgaca | gactaacaga | ctgttccttt | ccatgggtct | 1320 |
| tttctgcagt | caccgtcctt | gacacgaagc | ttatcgatat | gggaaaaatc | agcagtcttc | 1380 |
| caacccaatt | atttaagtgc | tgcttttgtg | atttcttgaa | ggtgaagatg | cacaccatgt | 1440 |
| cctcctcgca | tctcttctac | ctggcgctgt | gcctgctcac | cttcaccagc | tctgccacgg | 1500 |
| ctggaccgga | gacgctctgc | ggggctgagc | tggtggatgc | tcttcagttc | gtgtgtggag | 1560 |
| acaggggctt | ttatttcaac | aagcccacag | ggtatggctc | cagcagtcgg | agggcgcctc | 1620 |
| agacaggcat | cgtggatgag | tgctgcttcc | ggagctgtga | tctaaggagg | ctggagatgt | 1680 |
| attgcgcacc | cctcaagcct | gccaagtcag | ctcgctctgt | ccgtgcccag | cgccacaccg | 1740 |
| acatgcccaa | gacccagaag | gtaagcccac | ctgggtggga | tccagccatc | ctcaagtggt | 1800 |
| ctctctcttg | tgcatgtggg | tgggccaagc | agaaatcctg | ccccatagtc | tcctggctta | 1860 |
| caagtcagaa | aagctccttt | gcaccaaagg | gatggattac | atccccatct | ctttgctaaa | 1920 |
| caaacatggg | ctttggtgtc | agacaaaagt | gaagtcctgg | cttctcaca | caccagctta | 1980 |
| gagagaaaag | acttttaggt | gaatgtggca | ggaaagcgtg | cttgctgggg | caaaggcaga | 2040 |
| ttcattcttt | ctcttcccag | tatcagcccc | catctaccaa | caagaacacg | aagtctcaga | 2100 |

```
gaaggaaagg aagtacattt gaagaacgca agtagctttt tctcctttat ttataggaag    2160
tacatttgaa gaacgcaagt agagggagtg caggaaacaa gaactacagg atgtaggtcg    2220
acctcgagtc tagagggccc gtttaaaccc gctgatcagc ctcgactgtg ccttctagtt    2280
gccagccatc tgttgtttgc ccctcccccg tgccttcctt gaccctggaa ggtgccactc    2340
ccactgtcct ttcctaataa aatgaggaaa ttgcatcgca ttgtctgagt aggtgtcatt    2400
ctattctggg gggtggggtg gggcaggaca gcaaggggga ggattgggaa gacaatagca    2460
ggcatgctgg ggagtcgaaa ttcagaagaa ctcgtcaaga aggcgataga aggcgatgcg    2520
ctgcgaatcg ggagcggcga taccgtaaag cacgaggaag cggtcagccc attcgccgcc    2580
aagctcttca gcaatatcac gggtagccaa cgctatgtcc tgatagcggt ccgccacacc    2640
cagccggcca cagtcgatga atccagaaaa gcggccattt tccaccatga tattcggcaa    2700
gcaggcatcg ccatgggtca cgacgagatc ctcgccgtcg gcatgctcg ccttgagcct    2760 ggcgaacagt tcggctggcg cgagcccctg atgctcttcg tccagatcat cctgatcgac    2820
aagaccggct tccatccgag tacgtgctcg ctcgatgcga tgtttcgctt ggtggtcgaa    2880
tgggcaggta gccggatcaa gcgtatgcag ccgccgcatt gcatcagcca tgatggatac    2940
tttctcggca ggagcaaggt gagatgacag gagatcctgc cccggcactt cgcccaatag    3000
cagccagtcc cttcccgctt cagtgacaac gtcgagcaca gctgcgcaag aacgcccgt    3060 cgtggccagc cacgatagcc gcgctgcctc gtcttgcagt tcattcaggg caccggacag    3120
gtcggtcttg acaaaaagaa ccgggcgccc ctgcgctgac agccggaaca cggcggcatc    3180
agagcagccg attgtctgtt gtgcccagtc atagccgaat agcctctcca cccaagcggc    3240
cggagaacct gcgtgcaatc catcttgttc aatcatgcga aacgatcctc atcctgtctc    3300
ttgatcagat cttgatcccc tgcgccatca gatccttggc ggcaagaaag ccatccagtt    3360
tactttgcag ggcttcccaa ccttaccaga gggcgcccca gctggcaatt ccggttcgct    3420
tgctgcgtca gaccccgtag aaaagatcaa aggatcttct tgagatcctt ttttctgcg    3480 cgtaatctgc tgcttgcaaa caaaaaaacc accgctacca gcggtggttt gtttgccgga    3540
tcaagagcta ccaactcttt ttccgaaggt aactggcttc agcagagcgc agataccaaa    3600
tactgttctt ctagtgtagc cgtagttagg ccaccacttc aagaactctg tagcaccgcc    3660
tacatacctc gctctgctaa tcctgttacc agtggctgct gccagtggcg ataagtcgtg    3720
tcttaccggg ttggactcaa gacgatagtt accggataag gcgcagcggt cgggctgaac    3780
ggggggttcg tgcacacagc ccagcttgga gcgaacgacc tacaccgaac tgagatacct    3840
acagcgtgag ctatgagaaa gcgccacgct tcccgaaggg agaaaggcgg acaggtatcc    3900
ggtaagcggc agggtcggaa caggagagcg cacgagggag cttccagggg gaaacgcctg    3960
gtatctttat agtcctgtcg ggtttcgcca cctctgactt gagcgtcgat ttttgtgatg    4020
ctcgtcaggg gggcggagcc tatggaaaaa cgccagcaac gcggccttt tacggttcct    4080 ggccttttgc tggccttttg ctcacatg                                      4108
```

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28

```
tgatctaagg aggctgga                                              18
```

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29

```
ctacttgcgt tcttcaaatg                                            20
```